(12) United States Patent
Agnew et al.

(10) Patent No.: US 8,906,830 B2
(45) Date of Patent: *Dec. 9, 2014

(54) CAPTURE AGENTS AND RELATED COMPOSITIONS, METHODS AND SYSTEMS

(75) Inventors: Heather Agnew, Pasadena, CA (US);
Rosemary Rohde, Pasadena, CA (US);
Steven Millward, Monrovia, CA (US);
Arundhati Nag, Pasadena, CA (US);
James R. Heath, South Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/035,718

(22) Filed: Feb. 25, 2011

(65) Prior Publication Data

US 2011/0263515 A1 Oct. 27, 2011

Related U.S. Application Data

(63) Continuation of application No. 12/487,333, filed on Jun. 18, 2009.

(60) Provisional application No. 61/132,416, filed on Jun. 18, 2008, provisional application No. 61/155,890, filed on Feb. 26, 2009.

(51) Int. Cl.
| | |
|---|---|
| *C40B 30/04* | (2006.01) |
| *G01N 33/53* | (2006.01) |
| *G01N 33/531* | (2006.01) |
| *G01N 33/543* | (2006.01) |
| *C07D 249/04* | (2006.01) |

(52) U.S. Cl.
CPC .... *G01N 33/54306* (2013.01); *C12Q 2523/109* (2013.01); *C07D 249/04* (2013.01); *C40B 30/04* (2013.01); *G01N 33/531* (2013.01)
USPC .............................................. 506/9; 548/255

(58) Field of Classification Search
USPC .............................................. 506/9; 548/255
See application file for complete search history.

(56) References Cited

U.S. PATENT DOCUMENTS

| | | |
|---|---|---|
| 2007/0053934 A1 | 3/2007 | Kallenbach |
| 2009/0192048 A1 | 7/2009 | Reeeve |

FOREIGN PATENT DOCUMENTS

| | | |
|---|---|---|
| GB | 2433506 | 6/2007 |
| WO | WO 2004/003019 | 1/2004 |
| WO | WO 2006/116736 | 11/2006 |
| WO | 2007072976 A1 | 6/2007 |

OTHER PUBLICATIONS

Nissen et al., Science, 2000, 289:920-930.*
Dedola et al., Org. Biomol. Chem., 2007, 5:1006-1017.*
Montagnat et al. (Tetrahedron Letters, 2006, 47:6971-6974).*

(Continued)

*Primary Examiner* — Christopher M Babic
*Assistant Examiner* — Jeremy C Flinders
(74) *Attorney, Agent, or Firm* — Lathrop & Gage LLP

(57) ABSTRACT

The present disclosure relates to capture agents for the detection and/or separation of one or more targets in a sample. Described herein are multi-ligand capture agents comprising two or more ligands, and related compositions, methods and systems. In certain embodiments, the capture agents disclosed herein can be used for performing assays, including but not limited to assays for the detection and/or separation of targets.

10 Claims, 32 Drawing Sheets

(56) References Cited

OTHER PUBLICATIONS

Mammen et al. (Angew. Chem. Int. Ed., 1998, 37:2754-2794).*
Alluri, P. G., M. M. Reddy, K. Bachhawat-Sikder, H. J. Olivos, T. Kodadek, J. Am. Chem. Soc. 2003, 125, 13995.
Atherton, E. and R. C. Sheppard, in Solid Phase Peptide Synthesis—A Practical Approach, Oxford University Press, USA, 1989, p. 136.
Baldwin, J. J., J. J. Burbaum, I. Henderson, and M. H. J. Ohlmeyer(1995). "Synthesis of a Small Molecule Combinatorial Library Encoded with Molecular Tags." J. Am. Chem. Soc. 117(20): 5588-5589.
Blow, N., Nature 2007,447,741.
Bock, S.B. et al. Detection of S0phase cell cycle progression using 5-ethynyl-2'-deoxyuridine antibodies. Biotechniques, vol. 44, No. 7, pp. 927-929, Jun. 1, 2008.
Bock, V. D., H. Hiemstra, and J. H. van Maarseveen, (2006). "Cu—Catalyzed Azide-Alkyne "Click" Cycloadditions from a Mechanistic and Synthetic Perspective." Eur. J. Org. Chem.: 51-68.
Borrebaeck, C. A. K., Immunol. Today 2000,21:379.
Bourne, Y., H. C. Kolb, Z. Radic, K. B. Sharpless, P. Taylor, and P. Marchot (2004). "Freeze-frame inhibitor captures acetylcholinesterase in a unique conformation." Proc. Natl. Acad. Sci. USA 101 (6):1449-1454.
Brown, S. (1997). "Metal-recognition by repeating polypeptides." Nat. Biotechnol. 15: 269-272.
Burmeister, P.E., S. D. Lewis, R. F. Silva, J. R. Preiss, L. R. Horwitz, P. S. Pendergrast, T. G. McCauley, J. C. Kurz, D. M. Epstein, C. Wilson, A. D. Keefe, Chem. Bioi. 2005, 12:25.
Cao, P., K. Xu, and J. R. Heath (2008). "Azidation of Silicon(111) Surfaces." J. Am. Chem. Soc. 130(45): 14910-14911.
Carpino, L. A., A. El-Faham, C. A. Minor, and F. Albericio (1994). "Advantageous applications of azabenzotriazole (triazolopyridine)-based coupling reagents to solid-phase peptide synthesis." J, Chem. Soc., Chem. Commun. 2: 201-203.
Chenault, H. K., J. Dahmer, and G. M. Whitesides (1989). "Kinetic resolution of unnatural and rarely occurring amino acids: Enantioselective hydrolysis of N-acyl amino acids catalyzed by acylase I." J, Am. Chem. Soc. 111 (16): 6354-6364.
Coin, I., M. Beyermann, and M. Bienert (2007). "Solid-phase peptide synthesis: From standard procedures to the synthesis of difficult sequences." Nat. Protocols 2(12): 3247-3256.
Cox, J.C., A. Hayhurst, J. R. Hesselberth, T. S. Bayer, G. Georgiou, A. D. Ellington, Nucleic Acids Res. 2002, 30, e108.
Dixon, S. M.; P. Li, R. Liu, H. Wolosker, K. S. Lam, M. J. Kurth, and M. D. Toney (2006). "Slowbinding human serine racemase inhibitors from high-throughput screening of combinatorial libraries." J. Med. Chem. 49(8): 2388-2397.
Eteshola, E., L. J. Brillson, and S. C. Lee (2005). "Selection and characteristics of peptides that bind thermally grown silicon dioxide films." Biomol. Eng. 22: 201-204.
European Patent Office, Combined International Search Report and Written Opinion dated Nov. 9, 2009 for PCT/US2009/047799.
Fan, R., O. Vermesh, A. Srivastava, B. K. H. Yen, L. Qin, H. Ahmad, G. A. Kwong, C.-C. Liu, J. Gould, L. Hood, and J. R. Heath (2008). "Integrated barcode chips for rapid, multiplexed analysis of proteins in microliter quantities of blood." Nat. Biotechnol. 26: 1373-1378.
Furka, A., F. Sebestyen, M. Asgedom, and G. Dibo, (1991). "General method for rapid synthesis of multicomponent peptide mixtures." Int. J. Pept. Protein Res. 37: 487-493.
Garcia-Martin, F., N. Bay6-Puxan, L. J. Cruz, J. C. Bohling, and F. Albericio (2007). "Chlorotrityl Chloride (CTC) Resin as a Reusable Carboxyl Protecting Group." QSAR Comb. Sci. 26(10), 1027-1035.
Geysen, H. M. and T. J. Mason (1993). "Screening chemicalily synthesized peptide libraries for biologically-relevant molecules." Bioorg. Med. Chem. Lett. 3(3): 397-404.
Gramlich, P. M. E., C. T. Wirges, J. Gierlich, and T. Carell (2008). "Synthesis of Modified DNA by PCR with Alkyne-Bearing Purines Followed by a Click Reaction." Org. Lett. 10(2): 249-251.
Gold, L., B. Polisky, O. Uhlenbeck, M. Varus, Annu. Rev. Biochern. 1995, 64, 1094.

Halpin, D. R., J. A. Lee, S. J. Wrenn, and P. B. Harbury (2004). "DNA Display III. Solid-Phase Organic Synthesis on Unprotected DNA." PLoS Biology 2(7): 1031-1038.
Hardinan, G. Microarray platforms—comparisons and contrasts. Pharmacogenomics, vol. 5, No. 5, pp. 487-502, Jan. 1, 2004.
Hochgurtel, M., H. Kroth, D. Piecha, M. W. Hofmann, C. Nicolau, S. Krause, O. Schaaf, G. Sonnenmoser, and A. V. Eliseev (2002). "Target-induced formation of neuraminidase inhibitors from in vitro virtual combinatorial libraries." Proc. Natl. Acad. Sci. USA 99(6): 3382-3387.
Hu, X., J. Sun, H.-G. Wang, and R. Manetsch (2008). "Bcl-XL-Templated Assembly of Its Own Protein-Protein Interaction Modulator from Fragments Decorated with Thio Acids and Sulfonyl Azides." J. Am. Chem. Soc. 130(42): 13820-13821.
Jain, A., S. G. Huang, et al. (1994). "Lack of Effect of the Length of Oligoglycine-Derived and Oligo(Ethylene-Glycol)-Derived Para-Substituents on the Affinity of Benzenesulfonamides for Carbonic-Anhydrase-II in Solution." J. Am. Chem. Soc. 116(12): 5057-5062.
Kehoe, J. W., D. J. Maly, et al. (2002). "Tyrosylprotein sulfotransferase inhibitors generated by combinatorial target-guided liqand assembly." Bioorganic & Medicinal Chem. Lett. 12(3): 329-332.
Kodadek, T., M. M. Reddy, H. J. Olivos, K. Bachhawat-Sikder, P. G. Alluri, Acc. Chem. Res. 2004, 37, 711.
Kolb, H. C. and K. B. Sharpless (2003). "The growing impact of click chemistry on drug discovery." Drug Disc. Today 8(24): 1128-1137.
Krasinski, A., Z. Radic, R. Manetsch, J. Raushel, P. Taylor, K. B. Sharpless, and H. C. Kolb (2005). "In situ selection of lead compounds by click chemistry: Target-guided optimization of acetylcholinesterase inhibitors." J. Am. Chem. Soc. 127(18): 6686-6692.
Lam, K. S., M. Lebl, and V. KrchMk (1997). "The 'one-bead-one-compound' combinatorial library method." Chem. Rev. 97(2): 411-448.
Landon, L. A., J. Zou, and S. L. Deutscher (2004). "Effective combinatorial strategy carbohydrate to increase affinity of carbohydrate binding by peptides." Mol. Diversity 8: 35-50.
Laursen, R. A. (1971). "Solid-phase Edman degradation: An automatic peptide sequencer." Eur. J. Biochem. 20: 89-102.
Lee, J.F., J. R. Hesselberth, L. A. Meyers, A. D. Ellington, Nucleic Acids Res. 2004, 32, 095.
Lee, H.-S., J.-S. Park, B. M. Kim, and S. H. Gellman (2003). "Efficient synthesis of enantiomerically pure ~2-amino acids via chiral isoxazolidinones." J. Org. Chem. 68(4): 1575-1578.
Lehman, A., S. Gholami, M. Hahn, and K. S. Lam (2006). "Image subtraction approach to screening one-bead-one-compound combinatorial libraries with complex protein mixtures." J. Comb. Chem. 8(4): 562-570.
Lewis, J. K., J. Wei, and G. Siuzdak (2000). "Matrix-assisted laser desorption/ionization mass spectrometry in peptide and protein analysis." In Encyclopedia of Analytical Chemistry, R. A. Meyers (ed.),5880-5894.
Lewis, W.G. et al. Click chemistry in situ: acetylcholinesterase as a reaction vessel for the selective assembly of a femtomolar inhibitor from an array of building blocks. Angewandte Chemie, Int'l Edition, vol. 41, No. 6, pp. 1053-1057, Jan. 1, 2002.
Li, S., D. Bowerman, N. Marthandan, S. Klyza, K. J. Luebke, H. R. Garner, and T. Kodadek (2004). "Photolithographic Synthesis of Peptoids." J. Am. Chem. Soc. 126(13): 4088-4089.
Li, S., N. Marthandan, D. Bowerman, H. R. Garner, and T. Kodadek (2005). "Photolithographic synthesis of cyclic peptide arrays using a differential deprotection strategy." Chem. Commun. 581-583.
Liu, G. and K. S. Lam, in Combinatorial Chemistry—A Practical Approach, Ed. H. Fenniri, Oxford University Press, USA, 2000, pp. 43-44.
Lusvarghi, S., J. M. Kim, Y. Creeger, and B. A. Armitage (2009). "Refined multivalent display of bacterial spore-binding peptides." Org. Biomol. Chem. 7: 1815-1820.
Mammen, M., S. K. Choi, et al. (1998). "Polyvalent interactions in biological systems: Implications for design and use of multivalent ligands and inhibitors." Angewandte Chemie—International Edition 37(20): 2755-2794.

(56) References Cited

OTHER PUBLICATIONS

Manetsch, R., A. Krasinski, Z. Radic, J. Raushel, P. Taylor, K. B. Sharpless, and H. C. Kolb (2004). "In situ click chemistry: Enzyme inhibitors made to their own specifications." J. Am. Chem. Soc. 126(40): 12809-12818.

Marks, K. M., M. Rosinov, and G. P. Nolan (2004). "In Vivo Targeting of Organic Calcium Sensors via Genetically Selected Peptides." Chem. Biol. 11: 347-356.

McAlpine, M. C., H. D. Agnew, R. D. Rohde, M. Blanco, H. Ahmad, A. D. Stuparu, W. A. Goddard, and J. R. Heath (2008). "Peptide-Nanowire Hybrid Materials for Selective Sensing of Small Molecules." J. Am. Chem. Soc. 130(29): 9583-9589.

McCauley, T.G., N. Hamaguchi, Anal. Biochern. 2003, 319,244.

Mocharla V. P., B. Colasson, L. V. Lee, S. Roper, K. B. Sharpless, C.-H. Wong, and H. C. Kolb (2005). "In Situ Click Chemistry: Enzyme-Generated Inhibitors of Carbonic Anhydrase II." Angew. Chem. 117(1): 118-122; Angew. Chem. Int. Ed. 44(1): 116-120.

O'Donnell, M. J., C. Zhou, et al. (1996). "Solid-phase unnatural peptide synthesis." J. Am. Chem. Soc. 118(25): 6070-6071.

Panicker, R. C., X. Huang, and S. Q. Yao (2004). "Recent Advances in Peptide-Based Microarray Technologies." Comb. Chem. High Throughput Screen. 7(6): 547-556.

Papalia, G. A., S. Leavitt, M. A. Bynum, P. S. Katsamba, R. Wilton, H. Qiu, M. Steukers, S. Wang, L. Bindu, S. Phogat, A. M. Giannetti, T. E. Ryan, V. A. Pudlak, K. Matusiewicz, K. M. Michelson, A. Nowakowski, A. Pham-Baginski, J. Brooks, B. C. Tieman, B. D. Bruce, M. Vaughn, M. Baksh, Y. H. Cho, M. De Wit, A. Smets, J. Vandersmissen, L. Michiels, and D. G. Myszka (2006). "Comparative analysis of 10 small molecules binding to carbonic anhydrase II by different investigators using Biacore technology." Anal. Biochem. 359: 94-105.

Pocker, Y. and J. T. Stone (1967). "The Catalytic Versatility of Erythrocyte Carbonic Anhydrase. III. Kinetic Studies of the Enzyme-Catalyzed Hydrolysis of p-Nitrophenyl Acetate." Biochemistry 6(3):668-678.

Poulin-Kerstien, A. T. and P. B. Dervan (2003). "DNA-Templated Dimerization of Hairpin Polyamides." J. Am. Chem. Soc. 125(51): 15811-15821.

Proske, D., M. Blank, R. Buhmann, A. Resch, Appl. Microbial. Biotechnol. 2005, 69,367.

Ramstrom, O. and J. M. Lehn (2002). "Drug discovery by dynamic combinatorial libraries." Nature Rev. Drug Discov. 1 (1): 26-36.

Reddy, M.M., K. Bachhawat-Sikder, T. Kodadek, Chem. Biol. 2004, 11, 1127.

Rohde, R. D., H. D. Agnew, W.-S. Yeo, R. C. Bailey, and J. R. Heath (2006). "A Non-Oxidative Approach toward Chemically and Electrochemically Functionalizing Si(111)." J. Am. Chem. Soc. 128(29): 9518-9525.

Roice, M., I. Johannsen, and M. Meldal (2004). "High Capacity Poly(ethylene glycol) Based Amino Polymers for Peptide and Organic Synthesis." QSAR Comb. Sci. 23(8): 662-673.

Rostovtsev V. V., L. G. Green, V. V. Fokin, and K. B. Sharpless (2002). "A Stepwise Huisgen Cycloaddition Process: Copper(I)-Catalyzed Regioselective "Ligation" of Azides and Terminal Alkynes." Angew. Chem. 114(14): 2708-2711; Angew. Chem. Int. Ed. 41 (14): 2596-2599.

Sanghvi, A. B., K. P-H Miller, A. M. Belcher, and C. E. Schmidt (2005). "Biomaterials functionalization using a novel peptide that selectively binds to a conducting polymer." Nat. Mater. 4: 496-502.

Sano, T. and C. R. Cantor (1990). "Expression of a Cloned Streptavidin Gene in *Escherichia coli*." Proc. Natl. Acad. Sci. USA 87(1): 142-146.

Saxon, E. and Bertozzi, C. R. (2000). "Cell Surface Engineering by a Modified Staudinger Reaction." Science 287(5460): 2007-2010.

Schweitzer, B., et al., Microarrays to characterize protein interactions on a whole-proteome scale. Proteomics, vol. 3, No. 11, pp. 2190-2199, Nov. 1, 2003.

Smith, G. P. and V. A. Petrenko (1997). "Phage display." Chem. Rev. 97(2): 391-410.

Svedhem, S., K. Enander, M. Karlsson, H. Sjobom, B. Liedberg, S. Lofas, L.-G. Martensson, S. E. Sjostrand, S. Svensson, U. Carlsson, and I. Lundstrom (2001). "Subtle Differences in Dissociation Rates of Interactions between Destabilized Human Carbonic Anhydrase II Mutants and Immobilized Benzenesulfonamide Inhibitors Probed by a Surface Plasmon Resonance Biosensor." Anal. Biochem. 296(2): 188-196.

Tornoe and Meldal, "Peptidotriazoles: Copper(I)-Catalyzed 1,3-Dipolar Cycloadditions on Solid-Phase" in Peptides: The Wave of the Future (Lebel and Houghten, eds., 2001), p. 263.

Tornoe et al., J. Org. Chem. 67(9):3057-3064 (2002); Rostovtsev, V. V. et al., 2002].

Tse, W. C. and D. L. Boger (2004). "Sequence-Selective DNA Recognition: Natural Products and Nature's Lessons." Chem. Biol. 11: 1607-1617.

van Hest, J. C. M., K. L. Kiick, and D. A. Tirrell (2000). "Efficient incorporation of unsaturated methionine analogues into proteins in vivo." J. Am. Chem. Soc. 122(7): 1282-1288.

Wang, X., L. Peng, R. Liu, S. S. Gill, and Kit S. Lam (2005). "Partial Alloc-deprotection approach for ladder synthesis of 'one-bead one-compound' combinatorial libraries." J. Comb. Chem. 7(2): 197-209.

Weterings, J. J., S. Khan, G. J. van der Heden, J. W. Drijfhout, C. J. M. Melief, H. S. Overkleeft, S. H. van der Burg, F. Ossendorp, G. A. van der Marel, and D. V. Filippov (2006). "Synthesis of 2-alkoxy-8-hydroxyadenylpeptides: Towards synthetic epitope-based vaccines." Bioorg. Med. Chem. Lett. 16(12): 3258-3261.

Whaley, S. R., D. S. English, E. L. Hu, P. F. Barbara, and A. M. Belcher (2000). "Selection of peptides with semiconductor binding specificity for directed nanocrystal assembly." Nature 405: 665-668.

Whiting M., J. Muldoon, Y.-C. Lin, S. M. Silverman, W. Lindstrom, A. J. Olson, H. C. Kolb, M. G. Finn, K. B. Sharpless, J. H. Elder, and V. V. Fokin (2006). "Inhibitors of HIV-1 Protease by Using in Situ Click Chemistry." Angew. Chem. 118(9): 1463-1467; Angew. Chem. Int. Ed. 45(9): 1435-1439.

Williams, K. P., X.-H. Liu, T. N. M. Schumacher, H. Y. Lin, D. A. Ausiello, P. S. Kim, and D. P. Bartel (1997). "Bioactive and nuclease-resistant L-DNA ligand of vasopressin." Proc. Natl. Acad. Sci. USA 94: 11285-11290.

Yang, X., S. E. Bassett, X. Li, B. A. Luxon, N. K. Herzog, R. E. Shope, J. Aronson, T. W. Prow, J. F. Leary, R. Kirby, A. D. Ellington, and D. G. Gorenstein (2002). "Construction and selection of beadbound combinatorial oligonucleoside phosphorothioate and phosphorodithioate aptamer libraries designed for rapid PCR-based sequencing." Nucleic Acids Res. 30(23): e132.

Yin, H., R. I. Litvinov, G. Vilaire, H. Zhu, W. Li, G. A. Caputo, D. T. Moore, J. D. Lear, J. W. Weisel, W. F. DeGrado, J. S. Bennett (2006). "Activation of platelet allb133 by an exogenous peptide corresponding to the transmembrane domain of allb." J. Biol. Chem. 281 (48): 36732-36741.

Zhang, Z. and E. Fan (2006). "Solid phase synthesis of peptidotriazoles with multiple cycles of triazole formation." Tetrahedron Lett. 47(5): 665-669.

Ginalski: Practical lessons from protein structure prediction, Nuc. Ac. Res., 2005, 33: 1874.

Rees, David C. et al., "Fragment-Based Lead Discovery", Nature, 3:660-672 (2004).

Diamandis et al. 'The biotin-(strept) avidin system: principles and applications in biotechnology.' Clinical Chemistry. 1991, vol. 37, No. 5, pp. 625-636.

Franke et al. 'Peptide ligation through click chemistry for the generation of assembled and scaffolded peptides.' Tetrahedron Letters. 2005, vol. 46, No. 26, pp. 4479-4482.

Tjernberg et al. 'Controlling amyloid β-peptide fibril formation with protease-stable ligands.' Journal of Biological Chemistry. 1997, vol. 272, No. 19, pp. 12601-12605.

Office Action in related U.S. Appl. No. 12/487,333, filed Jun. 18, 2009, mailed Sep. 16 2014.

* cited by examiner

Azide + Triarylphosphine

Azide + Acetylene

US 8,906,830 B2

CAPTURE AGENTS AND RELATED COMPOSITIONS, METHODS AND SYSTEMS

CROSS REFERENCE TO RELATED APPLICATIONS

This application is a continuation of U.S. application Ser. No. 12/487,333, filed Jun. 18, 2009, which claims priority to U.S. Provisional Application Ser. No. 61/132,416, filed on Jun. 18, 2008, and to U.S. Provisional Application Ser. No. 61/155,890, filed on Feb. 26, 2009, the disclosures of all of which are incorporated herein by reference in their entirety.

STATEMENT OF GOVERNMENT GRANT

"The U.S. Government has certain rights in this invention pursuant to Grant No. CA119347 awarded by the National Institutes of Health."

TECHNICAL FIELD

The present disclosure relates to capture agents for detecting and/or separating one or more targets in a sample.

BACKGROUND

High sensitivity detection of targets and in particular of biomarkers has been a challenge in the field of biological molecule analysis, in particular when aimed at detection of a plurality of targets and/or at detection of a target of a certain dimension or present in the sample at a low concentration. Whether for pathological examination or for fundamental biology studies, several methods are commonly used for the detection of various classes of biomaterials and biomolecules.

Some of the techniques most commonly used in the laboratory for detection of single biological targets include gel electrophoresis, polyacrylamide gel electrophoresis (PAGE), western blots, fluorescent in situ hybridization (FISH), fluorescence activated cell sorting (FACS), polymerase chain reaction (PCR), and enzyme-linked immunosorbent assay (ELISA). These methods have provided the ability to detect one or more biomarkers in biological samples such as serum and tissues and are also suitable for diagnostic purposes.

Subsequent polynucleotide encoding approaches provided improvements over previous techniques, and in particular, allowed performance of a highly sensitive and selective multiplexed detection of targets.

SUMMARY

Provided herein, are capture agents that in several embodiments can be used to detect and/or separate efficiently one or more targets with high affinity and specificity.

According to a first aspect, a multi-ligand capture agent for a target is described. The multi-ligand capture agent comprises two or more ligands covalently linked to each other, wherein each of the two or more ligands specifically binds the target and is bindingly distinguishable from the other, and wherein the two or more ligands are arranged in the multi-ligand capture agent so that upon binding of the multi-ligand capture agent to the target, each of the two or more ligands specifically binds the target.

According to a second aspect, a composition is described. The composition comprises: a multi-ligand capture agent herein described and a compatible vehicle.

According to a third aspect, a method to detect a target is described, the method comprises contacting the target with a multi-ligand capture agent herein described for a time and under condition to allow binding of the multi-ligand capture agent with the target to form a multi-ligand capture agent target complex; and detecting the multi-ligand capture agent target complex.

According to a fourth aspect, a method for separating a target from another analyte in a mixture is described. The method comprises: adding a multi-ligand capture agent here described in the mixture for a time and under condition to allow specific binding of the multi-ligand capture agent with the target to form a multi-ligand capture agent target complex; and separating the multi-ligand capture agent target complex from the mixture.

According to a fifth aspect, a system for detecting a target is described. The system comprises a multi-ligand capture agent herein described and at least one of reagents necessary to perform detection of a multi-ligand capture agent target complex.

According to a sixth aspect, a system for separating a target from another analyte in a mixture is described. The system comprises a multi-ligand capture agent herein described and at least one of reagents necessary to perform separation of a multi-ligand capture agent target complex from the mixture.

According to a seventh aspect, a method to provide two or more ligands of a multi-ligand capture agent, in a multi-ligand is described. The method comprises providing the target; providing a plurality of candidate ligands; and selecting the candidate ligands capable of specifically binding the target at corresponding binding sites, where the binding sites are so arranged to allow covalent linkage between each ligand bound on each site with another.

In several embodiments, multi-ligand capture agents and related compositions methods and systems herein described allow production of a capture agent specific for a predetermined target without necessary prior knowledge of affinity agents against the target.

In several embodiments, multi-ligand capture agents and related compositions methods and systems herein described allow detection of a target with a sensitivity and selectivity at least comparable with antibodies' sensitivity and selectivity, while having an increased stability towards thermal shock, dehydration, pH variation, many chemical processes, as well as degradation by certain naturally occurring enzymes.

Additionally, in several embodiments, multi-ligand capture agents and related compositions methods and systems herein described allow rapid and/or cost-effective development of capture agents when compared to certain antibody-based solutions of the art.

Furthermore, in several embodiments, multi-ligand capture agents and related composition methods and systems herein described allow formation of capture agents with ligands of a diverse chemical nature.

Also in several embodiments, multi-ligand capture agents and related composition methods and systems herein described allow site specific targeting within a predetermined target molecule.

In several embodiments, multi-ligand capture agents and related composition methods and systems herein described allow highly oriented attachment of the multi-ligand capture agent to a substrate or surface in a monoparameter or multi-parameter assay.

BRIEF DESCRIPTION OF THE DRAWINGS

The accompanying drawings, which are incorporated into and constitute a part of this specification, illustrate one or more embodiments of the present disclosure and, together with the detailed description and the examples, serve to explain the principles and implementations of the disclosure.

DETAILED DESCRIPTION

Figure 1:
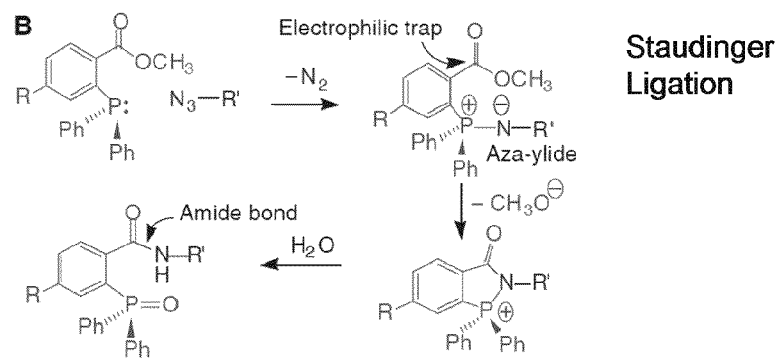
FIG. 1 shows a schematic representation of a covalent linkage according to some embodiments herein described.

Provided herein, are capture agents that in several embodiments can be used to detect and/or separate efficiently one or more targets with high affinity and specificity.

In several embodiments, multi-ligand capture agents herein described can be used in place of other capture agents for performing several assays, including but not limited to assays for the detection and/or separation of targets, which are identifiable by a skilled person upon reading of the present disclosure.

The term "capture agent" as used herein indicates a compound that can specifically bind to a target. For example, disclosed capture agents can be configured to specifically bind to a target. The disclosed capture agents can include but are not limited to organic molecules, such as polypeptides, polynucleotides and other non polymeric molecules that are identifiable to a skilled person. The multi-ligand capture agents herein described are examples of capture agents.

The wording "specific" "specifically" or "specificity" as used herein with reference to the binding of a first molecule to second molecule refers to the recognition, contact and formation of a stable complex between the first molecule and the second molecule, together with substantially less to no recognition, contact and formation of a stable complex between each of the first molecule and the second molecule with other molecules that may be present. Exemplary specific bindings are antibody-antigen interaction, cellular receptor-ligand interactions, polynucleotide hybridization, enzyme substrate interactions etc. The term "specific" as used herein with reference to a molecular component of a complex, refers to the unique association of that component to the specific complex which the component is part of. The term "specific" as used herein with reference to a sequence of a polynucleotide refers to the unique association of the sequence with a single polynucleotide which is the complementary sequence. By "stable complex" is meant a complex that is detectable and does not require any arbitrary level of stability, although greater stability is generally preferred.

The term "target" as used herein indicates an analyte of interest. The term "analyte" refers to a substance, compound, moiety, or component whose presence or absence in a sample is to be detected. Analytes include but are not limited to biomolecules and in particular biomarkers. The term "biomolecule" as used herein indicates a substance, compound or component associated with a biological environment including but not limited to sugars, amino acids, peptides, proteins, oligonucleotides, polynucleotides, polypeptides, organic molecules, haptens, epitopes, biological cells, parts of biological cells, vitamins, hormones and the like. The term "biomarker" indicates a biomolecule that is associated with a specific state of a biological environment including but not limited to a phase of cellular cycle, health and disease state. The presence, absence, reduction, upregulation of the biomarker is associated with and is indicative of a particular state. The "biological environment" refers to any biological setting, including, for example, ecosystems, orders, families, genera, species, subspecies, organisms, tissues, cells, viruses, organelles, cellular substructures, prions, and samples of biological origin.

Exemplary capture agents already known in the art include antibodies, polynucleotides and aptamers.

The term "antibody" as used herein refers to a protein of the kind that is produced by activated B cells after stimulation by an antigen and can bind specifically to the antigen promoting an immune response in biological systems. Full antibodies typically consist of four subunits including two heavy chains and two light chains. The term antibody includes natural and synthetic antibodies, including but not limited to monoclonal antibodies, polyclonal antibodies or fragments thereof. Exemplary antibodies include IgA, IgD, IgG1, IgG2, IgG3, IgM and the like. Exemplary fragments include Fab Fv, Fab' F(ab')2 and the like. A monoclonal antibody is an antibody that specifically binds to and is thereby defined as complementary to a single particular spatial and polar organization of another biomolecule which is termed an "epitope". In some forms, monoclonal antibodies can also have the same structure. A polyclonal antibody refers to a mixture of different monoclonal antibodies. In some forms, polyclonal antibodies can be a mixture of monoclonal antibodies where at least two of the monoclonal antibodies binding to a different antigenic epitope. The different antigenic epitopes can be on the same target, different targets, or a combination. Antibodies can be prepared by techniques that are well known in the art, such as immunization of a host and collection of sera (polyclonal) or by preparing continuous hybridoma cell lines and collecting the secreted protein (monoclonal).

The term "polynucleotide" as used herein indicates an organic polymer composed of two or more monomers including nucleotides, nucleosides or analogs thereof. The term "nucleotide" refers to any of several compounds that consist of a ribose or deoxyribose sugar joined to a purine or pyrimidine base and to a phosphate group and that is the basic structural unit of nucleic acids. The term "nucleoside" refers to a compound (such as guanosine or adenosine) that consists of a purine or pyrimidine base combined with deoxyribose or ribose and is found especially in nucleic acids. The term "nucleotide analog" or "nucleoside analog" refers respectively to a nucleotide or nucleoside in which one or more individual atoms have been replaced with a different atom or a with a different functional group. Accordingly, the term "polynucleotide" includes nucleic acids of any length, and in particular DNA, RNA, analogs and fragments thereof. A polynucleotide of three or more nucleotides is also called "nucleotidic oligomer" or "oligonucleotide."

The term "aptamers" as used here indicates oligonucleic acid or peptide molecules that bind a specific target. In particular, nucleic acid aptamers can comprise, for example, nucleic acid species that have been engineered through repeated rounds of in vitro selection or equivalently, SELEX (systematic evolution of ligands by exponential enrichment) to bind to various molecular targets such as small molecules, proteins, nucleic acids, and even cells, tissues and organisms. Aptamers are useful in biotechnological and therapeutic applications as they offer molecular recognition properties that rival that of the antibodies. Peptide aptamers are peptides that are designed to specifically bind to and interfere with protein-protein interactions inside cells. In particular, peptide aptamers can be derived, for example, according to a selection strategy that is derived from the yeast two-hybrid (Y2H) system. In particular, according to this strategy, a variable peptide aptamer loop attached to a transcription factor binding domain is screened against the target protein attached to a transcription factor activating domain. In vivo binding of the peptide aptamer to its target via this selection strategy is detected as expression of a downstream yeast marker gene.

The term "multi-ligand capture agent" used herein indicates an agent that can specifically bind to a target through the specific binding of multiple ligands comprised in the agent. For example, a multi-ligand capture agent can be a capture agent that is configured to specifically bind to a target through the specific binding of multiple ligands comprised in the capture agents. Multi-ligand capture agents can include molecules of various chemical natures (e.g. polypeptides polynucleotides and/or small molecules) and comprise both capture agents that are formed by the ligands and capture agents that attach at least one of the ligands.

In particular, multi-ligand capture agents herein described can comprise two or more ligands each capable of binding a target. The term "ligand" as used herein indicates a compound with an affinity to bind to a target. This affinity can take any form. For example, such affinity can be described in terms of non-covalent interactions, such as the type of binding that occurs in enzymes that are specific for certain substrates and is detectable. Typically those interactions include several weak interactions, such as hydrophobic, van der Waals, and hydrogen bonding which typically take place simultaneously. Exemplary ligands include molecules comprised of multiple subunits taken from the group of amino acids, non-natural amino acids, and artificial amino acids, and organic molecules, each having a measurable affinity for a specific target (e.g. a protein target). More particularly, exemplary ligands include polypeptides and peptides, or other molecules which can possibly be modified to include one or more functional groups. The disclosed ligands, for example, can have an affinity for a target, can bind to a target, can specifically bind to a target, and/or can be bindingly distinguishable from one or more other ligands in binding to a target. Generally, the disclosed multi-ligand capture agents will bind specifically to a target. For this it is not necessary that the individual ligands comprised in the multi-ligand capture agent be capable of specifically binding to the target individually, although this is also contemplated.

The term "polypeptide" as used herein indicates an organic linear, circular, or branched polymer composed of two or more amino acid monomers and/or analogs thereof. The term "polypeptide" includes amino acid polymers of any length including full length proteins and peptides, as well as analogs and fragments thereof. A polypeptide of three or more amino acids is also called a protein oligomer, peptide or oligopeptide. In particular, the terms "peptide" and "oligopeptide" usually indicate a polypeptide with less than 50 amino acid monomers. As used herein the term "amino acid", "amino acidic monomer", or "amino acid residue" refers to any of the twenty naturally occurring amino acids, non-natural amino acids, and artificial amino acids and includes both D an L optical isomers. In particular, non-natural amino acids include D-stereoisomers of naturally occurring amino acids (these including useful ligand building blocks because they are not susceptible to enzymatic degradation). The term "artificial amino acids" indicate molecules that can be readily coupled together using standard amino acid coupling chemistry, but with molecular structures that do not resemble the naturally occurring amino acids. The term "amino acid analog" refers to an amino acid in which one or more individual atoms have been replaced, either with a different atom, isotope, or with a different functional group but is otherwise identical to original amino acid from which the analog is derived. All of these amino acids can be synthetically incorporated into a peptide or polypeptide using standard amino acid coupling chemistries (Lam, K. S. et al., 1997). The term "polypeptide" as used herein includes polymers comprising one or more monomer, or building blocks other than an amino acid monomer. The terms monomer, subunit, or building blocks indicate chemical compounds that under appropriate conditions can become chemically bonded to another monomer of the same or different chemical nature to form a polymer. The term "polypeptide" is further intended to comprise a polymer wherein one or more of the building blocks is covalently bound to another by a chemical bond other than amide or peptide bond. In several embodiments, at least one ligand of the two or more ligands comprises one or more amino acid residues and can in particular be formed by a polypeptide. In particular, in several embodiments, at least one of the at least two ligands is a peptide comprising between three and hundred monomers, and in particular, between five and eighty monomers. In some embodiments, the peptide can comprise three to ten monomers, and in particular five to seven monomers. In some embodiments, the multi-ligand capture agent can be comprised of a protein.

The term "protein" as used herein indicates a polypeptide with a particular secondary and tertiary structure that can interact with another analyte and in particular, with other biomolecules including other proteins, DNA, RNA, lipids, metabolites, hormones, chemokines, and small molecules.

In particular, the protein comprised in capture agents herein described can be a non-naturally occurring protein, i.e. a protein that, as such, does not exist in nature and without artificial aid. Non-naturally occurring proteins include proteins that can be derived by modification of a naturally occurring protein.

More particularly, in several embodiments multi-ligand capture agents can be constructed from peptide ligands, each of which is constructed from a unique set of amino acids, some of which are non-naturally occurring, and/or are designed with unique chemical functions for a specific task. In some of those embodiments, the peptides are synthesized using artificial amino acid and/or result in non-naturally occurring peptides similar or dissimilar in structure and/or function to naturally occurring peptides, in accordance with a predetermined experimental design. A multi-ligand capture agent that comprises one or more peptide, polypeptide, or protein ligands can be referred to as a multi-ligand capture agent of a protein nature.

In several embodiments, where a multi-ligand capture agent comprises amino acid ligands, multi-ligand capture agents can be produced in multigram quantities at low cost since amino acid building blocks are readily available, or are not difficult to chemically synthesize in relatively large quantities. Procedure to synthesize amino acids and peptides are known to the skilled person and exemplified in the procedures illustrated in Example 1.

In other embodiments, a multi-ligand capture agent comprises ligands that have a chemical nature other than amino acidic. In particular, in some exemplary embodiments multi-ligand capture agents can be formed by polynucleotides (and in particular oligonucleotides), small molecules, and various other ligands possibly having a biological activity.

The term "small molecule" as used herein indicates an organic compound that is of synthetic or biological origin and that, although might include monomers and/or primary metabolites, is not a polymer. In particular, small molecules can comprise molecules that are not protein or nucleic acids, which play a biological role that is endogenous (e.g. inhibition or activation of a target) or exogenous (e.g. cell signalling), which are used as a tool in molecular biology, or which are suitable as drugs in medicine. Small molecules can also have no relationship to natural biological molecules. Typically, small molecules have a molar mass lower than 1 kg·mol$^{-1}$. Exemplary small molecules include secondary metabolites (such as actinomicyn-D), certain antiviral drugs (such as amantadine and rimantadine), teratogens and carcinogens(such as phorbol 12-myristate 13-acetate), natural products (such as penicillin, morphine and paclitaxel) and additional molecules identifiable by a skilled person upon reading of the present disclosure.

Also in embodiments where the ligands are formed by compounds of non-amino acidic nature, ligands can be synthesized using artificial compounds (such as nucleotide or nucleoside analogs) and can result in non-natural ligands that can possibly mimic a corresponding molecule occurring in nature. Procedures to synthesize non-aminoacidic molecule suitable as ligands, are known in the art. For example a procedure to assemble the monomers comprising non-peptidic capture agents involves reactions specific to that particular class of ligand, such as the formation of a phosphodiester bond between two nucleotides of a polynucleotide capture agent, or any of a host of reactions common to organic synthesis (e.g., amide bond formation, C—C bond formation, $S_N1$, $S_N2$, E1, E2) for a small molecule capture agent. Additional procedures suitable to synthesize the molecule are identifiable by a skilled person and will not be described in further detail.

In some embodiments a multi-ligand capture agent can be formed by ligands of a same chemical nature. In other embodiments, a multi-ligand capture agent can be formed by ligands of a different chemical nature as will be appreciated by a skilled person upon reading of the present disclosure.

In particular, in several embodiments one or more ligands of a multi-ligand capture agent may differ in chemical nature from any of the other ligands comprised in the same capture agent. The resulting multi-ligand capture agent can include at least two compounds having different chemical natures and is herein also identified as a chimeric capture agent or chimeric multi-ligand capture agent. Exemplary chimeric multi-ligand capture agents include but are not limited to small-molecule/peptide, small-molecule/polynucleotide, and polynucleotide/peptide. A skilled person will appreciate that the chemical nature of the ligands comprising the multi-ligand capture agent is not limiting, because the sequential addition of ligands is achieved not by the composition of the ligands themselves but by the functional groups that the ligands append as further illustrated in the present disclosure.

In some embodiments, one or more ligands of a multiligand capture agent are unrelated to at least one other ligand comprised in a same multiligand capture agent and/or is unrelated to the target. The term "unrelated" as used herein between two items indicates a lack of connection or association by reason of a previously established relation and in particular by common ancestry.

In the multi-ligand capture agents herein described, each of the two or more comprised ligands can specifically bind the target for the multi-ligand capture agent, and can be bindingly distinguishable from the other.

The wording "bindingly distinguishable" as used herein with reference to molecules and in particular ligands, indicates molecules that are distinguishable based on their ability to bind to a specific molecule or a portion thereof. Accordingly, for example, a first molecule is bindingly distinguishable from a second molecule if the first molecule specifically binds to, a third molecule and the second molecule specifically binds to a fourth molecule, with the fourth molecule distinct from the third molecule. If the first and second molecule specifically binds a same third molecule, the first molecule is bindingly distinguishable from the second molecule if the first molecule specifically binds to a first portion of the third molecule and the second molecule specifically binds to a second portion of the third molecule, with the first portion of the third molecule distinct from the second portion of the third molecule. Accordingly, for example, a first ligand and a second ligand which bind the same target are bindingly distinguishable if the first ligand specifically binds to a first portion or moiety of the target (e.g. a first binding site of a target protein) and the second ligand specifically binds to a second portion or moiety of the target (e.g. a second binding site of a target protein), with the first portion or moiety of the target distinct from the second portion or moiety of the target. As another example, a first ligand and a second ligand which bind the same target are bindingly distinguishable if the first ligand binds to a first portion or moiety of the target (e.g. a first binding site of a target protein), the second ligand binds to a second portion or moiety of the target (e.g. a second binding site of a target protein)—with the first portion or moiety of the target distinct from the second portion or moiety of the target—and the first ligand does not bind to the second portion or moiety, the second ligand does not bind the first portion or moiety, or both.

In particular, for example, the two or more ligands can be arranged in the multi-ligand capture agent so that upon binding of the capture agent with the target each of the two or more ligands binds the target, such as by specifically binding the target. In particular, for example, the two or more ligands can bind adjacent binding sites on the target. In those embodiments, the two or more ligands are bound to each other by a covalent bond.

The term "covalent bond" or "covalent link" or "covalent linkage" indicates a form of chemical bonding that is characterized by the sharing of pairs of electrons between atoms, or between atoms and other covalent bonds. Exemplary covalent linkages linking the at least two ligands include but are not limited to amide or peptide bond, the modified Staudinger ligation between an azide and triarylphosphine (see FIG. 1 and E. Saxon et al. in *Science* (2000), Vol. 287, 2007-2010, incorporated herein by reference in its entirety), a 1,2,3-triazole covalently linking an azide and acetylene (see FIG. 2 and V. D. Bock et al. in *Eur. J. Org. Chem.* (2006), 51-68, incorporated herein by reference in its entirety), an acylsulfonamide covalently linking a sulfonyl azide and thio acid (see FIG. 3 and X. Hu et al. in *J. Am. Chem. Soc.* (2008), Vol. 130, 13820-13821 incorporated herein by reference in its entirety) and the coupling of aldehyde and primary amine to form a transient hemiaminal or imine which is reduced to yield a secondary or tertiary amine (see FIG. 4 and M. Hochgürtel et al. in *Proc. Natl. Acad. Sci. USA* (2002), Vol. 99, 3382-3387,130, 13820-13821 incorporated herein by reference in its entirety).

In some embodiments, the multi-ligand capture agent comprises a plurality of ligands and in particular can include two to five ligands, or even more ligands depending on the experimental design according to criteria identifiable by a skilled person upon reading of the present disclosure. Properties of multi-ligand capture agents of increased length (e.g., three or more ligands) can include enhanced enthalpic stabilization upon binding to target (leading to enhanced affinity) and increased specificity in this binding interaction. For example, the long polypeptide chains comprising a peptide-based multi-ligand capture agent can adopt 3D folded structures thereby increasing the number of possible tertiary interactions with the target. Properties of multi-ligand capture agents of reduced length (e.g., three or fewer ligands) can include a reduced entropic cost for binding to target and a reduced synthetic burden.

In embodiments where a multi-ligand capture agent comprises a plurality of ligands, the exact number of ligands used can be dependent upon both the nature of the target, the Chemical nature of the ligands, and the ultimate binding affinity with the target that is desired.

The term "binding affinity" or "affinity" as used herein indicates affinity associated with binding of a first molecule to a second molecule. In particular, for example, binding affinity can refer to a measure of the strength of the binding. For example, association constants, dissociation constants, on-rates, off-rates, and other kinetic and binding measures can be measures and/or components of binding affinity. Binding affinities are influenced by non-covalent intermolecular interactions between the two molecules such as hydrogen bonding, electrostatic interactions, hydrophobic interactions, and van der Waals forces. Association and dissociation constants are typically expressed in terms of concentration of the ligand (that is, the molecule considered to be binding to the other molecule). Unless otherwise indicated by the context, quantitative and relative references to affinities and binding affinities are expressed as dissociation constants for the binding of the first molecule with the second molecule. The smaller the dissociation constant, the more tightly bound is the ligand, or the better the binding affinity between the two molecules.

In several embodiments, for ligands such as a 6- or A 7-mer peptide, a dissociation constant for binding of the ligand to the target of $10^{-4}$-$10^{-6}$ M are typically achievable. Dissociation constants of $10^{-6}$-$10^{-7}$ M and $10^{-7}$-$10^{-8}$ M and $10^{-8}$-$10^{-9}$ M are typically achievable, respectively, for biligand capture agents such as a 14-mer peptide (see FIG. 5) and triligand capture agents such as a 22-mer peptide (see FIG. 6) In one exemplary case, two small-molecule ligands have been shown to specifically contact the target and covalently react with each other to form an inhibitor having a dissociation constant of $10^{-15}$ M (Lewis, W. G. et al., 2002; Manetsch, R. et al., 2004; Bourne, Y. et al., 2004; Krasiński, A. et al., 2005).

Multi-ligand capture agents comprised of ligands of a diverse chemical nature herein described do not display limitations on length and achievable affinity. A single requirement is that the chemical nature of each ligand of the multi-ligand capture agent permits presentation of one of several functional groups (e.g., azide or acetylene, sulfonyl azide or thio acid, triarylphosphine or azide, or aldehyde or amine), which accordingly permit the sequential assembly of n-ligands comprising multi-ligand capture agents as exemplified in FIGS. 7-11) and further described in the present disclosure.

In several embodiments, multi-ligand capture agents are linear capture agents, i.e. capture agents wherein two or more ligands are linked to each other in a chain like structure. Exemplary linear multi-ligand capture agents of the present disclosure are described in Examples 7-21 and include a biligand capture agent comprised of two 7-mer D-peptide ligands (1° and 2°) (see FIG. 5, FIG. 12, FIG. 13 and FIG. 14) and a triligand capture agent, comprised of three D-peptide ligands (1°, 2°, and 3°) (see FIG. 6 and FIG. 15).

In several embodiments, the multi-ligand capture agents herein described are branched capture agents, i.e. capture agents wherein at least one of the at least two ligands is located or extends from the main portion of the capture agent. In particular, branched capture agents include a branched molecule, such as a branched polypeptide, configured to present at least one of the two or more ligands in the branched portion of the molecule. Exemplary branched multi-ligand capture agents are described in Example 17, and include, a branched biligand capture agent comprised of two 7-mer D-peptide ligands (1° and 2°), where the 1° ligand is connected to the 2° ligand at a non-terminal residue within the 2° ligand which displays a 5-fold affinity enhancement over similarly corresponding linear biligand capture agent (see FIG. 16A in comparison with FIG. 5), and a branched triligand capture agent comprised of three 7-mer D-peptide ligands (1°, 2°, and 3°), where the 3° ligand is connected to a branched biligand anchor at a terminal residue (shown schematically in FIG. 17B) (see FIG. 18 in comparison with FIG. 6).

In several embodiments, the multi-ligand capture agent comprises at least two ligands that are not covalently linked in nature.

In particular in some embodiments, a multi-ligand capture agent comprises at least two ligands that are not portions of a same naturally occurring molecule, and in particular that are not portions of a same substrate of the target.

In some embodiments, a multi-ligand capture agent comprises at least one ligand that is selected, and in particular designed, independently from a compound known to bind the target. In particular, in some embodiments, at least one ligand of the multi-ligand capture agents is not modeled on and/or derived from a compound known to bind the target.

In some embodiments, a multi-ligand capture agent comprises at least one ligand that is capable to bind the target in isolation. In some of these embodiments one or more additional ligands can be comprised in the multi-ligand capture agent, the one or more additional ligand contacting the target upon specific binding of the capture agent to the target.

In several multi-ligand capture agents herein described the structure of the capture agent as well as the number, chemical nature and possible modifications of the ligands can be determined in view of a desired binding affinity and binding specificity for the target of choice. The term "binding specificity" as used herein indicates the fold difference between binding affinity of the multi-ligand capture agent to the target and the binding affinity of the multi-ligand capture agent to a reference molecule.

In some embodiments, the binding specificity of the multi-ligand capture agent relative to the reference molecule is at least 5, at least 10, at least 20, or at least 100. A reference molecule is any molecule for which the binding affinity of a multi-ligand capture agent is to be compared to the binding affinity of a multi-ligand capture agent to the target. In some embodiments, where binding of a ligand or multi-ligand to several different targets is described, a reference molecule can be provided by a molecule that is different from any of the targets. For example, if the target is a serum protein, the reference molecule can be another serum protein, cytoplasmic protein, or protein of a shared ancestry relative to the target. In those embodiments, a reference molecule allows, for example, measurement and monitoring of a difference in binding affinities between a ligand or multi-ligand for the target and for a reference molecule that is not the target. In some embodiments, where a differential binding of several ligands or multi-ligands to a target is described, a reference molecule can be formed by the target. In those embodiments, the relative binding affinities of the ligand or multi-ligands to a single target can be measured and monitored by use of the reference molecule. In those embodiments, a reference molecule allows, for example, measurement and monitoring of an increase in the difference in binding affinities by different forms of ligands or multi-ligands, such as during the disclosed methods of producing and/or identifying multi-ligand capture agents. As noted above, the difference in the binding affinity of a multi-ligand capture agent for the target and for a reference molecule can be referred to as the binding specificity of the multi-ligand capture agent.

In some embodiments, the binding specificity of the multi-ligand capture agent relative to the target can be based on the binding specificity of the multi-ligand capture agent for a reference molecule related to the target. In particular in some of those embodiments, the reference molecule related to target is an allelic version of the target, a homolog of the target and/or a modified form of the target.

In some embodiments, the binding affinity of the multi-ligand capture agent to the target can be, for example, at least $10^6$, at least $10^7$, at least $10^8$, at least $10^9$, at least $10^{10}$, at least $10^{11}$, at least $10^{12}$, or at least $10^{13}$ higher that the binding affinity of the anchor ligand.

In some embodiments, the dissociation constant for the binding of the multi-ligand capture agent to the target is equal to or less than $10^{-6}$ M, $10^{-7}$ M, $10^{-8}$ M, $10^{-9}$ M, $10^{-10}$ M, $10^{-11}$ M, $10^{-12}$ M, $10^{-13}$ M, $10^{-14}$ M, $10^{-15}$ M, or $10^{-16}$ M.

In several embodiments, the multi-ligand capture agents can be synthesized or modified to introduce a desired feature in the capture agents. Exemplary desired features are those enabling or improving a chemical or biological activity in the multi-ligand capture agents. Exemplary chemical or biological activities include solubility, and in particular, water solubility, detectability (including detectability in specific environments), bioavailability (and in particular ability to reach the systemic circulation of an individual to whom the capture agent is administered), immunogenicity, (and in particular the ability of the capture agent to provoke are humoral or cell-mediated immune response in an individual to whom the capture agent is administered), and reactivity (including ability to react or bind with a compound or material and in particular to bind a another compound or molecule of interest and/or a surface). Desired features can be typically introduced by addition of another molecules or functional group during or after the multiligand capture agent synthesis. Exemplary molecule or functional groups enabling or improving a desired chemical or biological activity comprise a hydrophilic or hydrophobic molecule or functional groups (e.g. a polyether or polynucleotide), a carrier (e.g. a vaccine carrier), and a label (e.g. a molecule or functional group allowing detection of the capture agent such an encoding molecule, e.g. an encoding polynucleotide, a fluorescent dye or a gold nanoparticle).

Exemplary modified multi-ligand capture agents include a biligand capture agent comprised of two 7-mer D-peptide ligands and modified at the N-terminus to present an acetylene functional group for binding with a tertiary ligand (see FIG. 12), a capture agent modified with amino acid side residue with chain protecting groups which stabilize the capture agent for organic reactions conducted at neutral and basic pH (see structure of FIG. 13), a capture agent modified at the N- or C-terminus to include a biotin molecule which allows detectability of the capture agent in dot blots, western blots, and ELISA-like assays (see FIGS. 14 and 15), and a capture agent modified at the N-terminus to include a fluorescent dye molecule which provides detectability of the capture agent in biological assays including fluorescence polarization (see Example 6), immunocytochemistry, and immunohistochemistry.

In some embodiments, multi-ligand capture agents, and in particular multi-ligand capture agents comprising peptide ligands, can be synthesized or modified to include one or more protecting groups (e.g. alcohol protecting, amine protecting, carbonyl protecting groups etc) For example in some embodiments, the multi-ligand capture agent can be synthesized on a solid-phase resin and released under conditions that leave standard side chain protecting groups intact. In other exemplary embodiments, side chain protection of one or more residues can be used to allow binding of the multi-ligand capture agent with other compounds, and in particular with other ligands (e.g. CuAAC, see Example 12), in applications where such binding is desired. Examples of those applications include bulk synthesis of the capture agents via fragment condensation. In other embodiments, side chain protection can be used to obtain a multi-ligand cyclization. In particular a multi-ligand capture agent can be functionalized with a first functional group (e.g. —SH) on one end and second functional group (e.g. —SH) on the other end of the capture agent. The first and second functional groups then are permitted to react with each other to produce a single closed loop structure (e.g. disulfide bond). This closed loop structure displays reduced conformational entropy which can further stabilize the binding interaction of the multi-ligand capture agent with the target. In other embodiments side chain protection can be used to achieve highly oriented covalent attachment of the multi-ligand capture agent to a substrate or surface in a monoparameter or multiparameter assay. In any of those embodiments, once the chemical transformation described by any of these three utilities is completed, the side chain protection can be removed (e.g. through an acid treatment).

In several embodiments, multi-ligand capture agents can be synthesized or modified to add compounds able to provide water solubility to the multiligand capture agent. Exemplary compounds include but are not limited to hydrophilic molecules such as polyethers (e.g. polyethylene glycol (PEG) or oligonucleotides) and other polymers that are nonionic, nontoxic, biocompatible, and highly hydrophilic. For example, PEGylated capture agents can have enhanced therapeutic properties due to their increased water solubility and bioavailability.

In several embodiments, multi-ligand capture agents can be synthesized with or modified to include stable nonradioactive (e.g. $^2$H, $^{15}$N, or $^{13}$C) or radioactive isotopes (e.g. $^3$T, $^{14}$C, $^{35}$S, or $^{32}$P) which permit quantitative assays including characterization of activity of the target in the presence of the capture agent and/or binding affinity of the capture agent for the target.

In several embodiments, multi-ligand capture agents can be modified to be conjugated to a carrier such as keyhole limpet hemocyanin (KLH), BSA, or ovalbumin to raise polyclonal antibodies against the capture agent for biochemical or immunolocalization studies. The conjugation between the multiligand capture agents and the carrier can be achieved by the maleimide method, which couples a cysteine residue of the multi-ligand capture agent to the carrier protein.

In several embodiments, multi-ligand capture agents can be modified to be conjugated to a biotin molecule to allow or enhance detectability. Biotin-labeled multi-ligand capture agents can be further labeled with streptavidin-linked proteins such as alkaline phosphatase or horseradish peroxidase that allow for amplification of the interaction of the capture agent with its target. In another embodiment, a biotin label can be transformed into a fluorophore label via the adaptor proteins such as streptavidin-Cy5.

In several embodiments, multi-ligand capture agents can be modified to be conjugated to gold nanoparticle labels which allow visualization of the capture agent binding to the target in complex samples (e.g. tissue sections) by methods including dark-field and electron microscopies. This conjugation can be achieved by the maleimide method, which couples a free thiol (e.g. —SH) of the multi-ligand capture agent to the gold nanoparticle. This conjugation can also be achieved by the sulfo-N-hydroxysuccinimide ester (sulfo-NHS) method wherein the gold nanoparticles are reacted with a primary amine in the multi-ligand capture agent under mild conditions (pH 7.5 to 8.2). Free thiols and primary amines are examples of functional groups that either are preexisting components of capture agents, or are routinely installed modifications achieved by chemistry identifiable by a skilled person.

In some embodiments, multi-ligand capture agents can be modified by addition of another molecule of interest, such as another peptide, small molecule, or protein, with predetermined affinity for a target other than the target(s) of the multiligand capture agent. In embodiments, wherein the two targets are both proteins, the modified multiligand capture agent can be used to analyze protein-protein interactions.

In several embodiments, multi-ligand capture agents herein described are multi-ligand protein capture agents, i.e. capture agents comprising at least a portion that has a binding affinity for a specific protein. Exemplary multi-ligand protein capture agents include but are not limited to capture agents of any chemical nature that are able to specifically recognize, contact and form a stable complex with a target of a protein nature. In particular, binding of the multi-ligand protein capture agent to a target protein can be performed through specific binding of one or more portions of the protein capture agent to one or more binding sites of the target protein. In embodiments where the multi-ligand capture agent is a multi-ligand protein capture agent, the two or more ligands can be adjacently bound to adjacent binding sites of the target protein.

In some embodiments, multi-ligand capture agents can recognize additional targets that are of a biological but non-protein nature. Exemplary multi-ligand capture agents include but are not limited to capture agents of any chemical nature that are able to specifically recognize, contact and form a stable complex with a biological target of a non-protein nature, including nucleic acid, carbohydrate, peptide, small molecule, and/or bacterial spore targets. In particular, binding of the multi-ligand capture agent to the non-protein target can be performed through binding of one or more portions of the capture agent to one or more adjacent binding sites of the target. In particular, dimerization of polyamides on a DNA target has been demonstrated (Poulin-Kerstien, A. T. and P. B. Dervan, 2003). In some embodiments, multi-ligands comprising two or more natural products can specifically bind to a nucleic acid target (Tse, W. C. and D. L. Boger, 2004). Furthermore, multi-ligands comprising two or more peptides can specifically bind to a carbohydrate (Landon, L. A. et al., 2004), fluorescent dye (Marks, K. M. et al., 2004), or bacterial spore target (Lusvarghi, S. et al., 2009). Furthermore, multi-ligands comprising two or more polynucleotides can specifically bind to a peptide target (Williams, K. P. et al., 1997).

In some embodiments, multi-ligand capture agents also can recognize targets of a non-biological nature. Exemplary multi-ligand capture agents include but are not limited to capture agents of any chemical nature that are able to specifically recognize, contact and form a stable complex with a non-biological target, including metals and metal ions, semiconductors, and conducting polymers. In particular, binding of the multi-ligand capture agent to the non-biological target can be performed through binding, and in particular, specific binding, of one or more portions of the capture agent to one or more sites of the target. In some embodiments, multi-ligands comprising two or more peptides can specifically bind Au or Cr (Brown, S., 1997), gallium arsenide (Whaley, S. R. et al., 2000), silicon oxide (Eteshola, E. et al., 2005), or polypyrrole polymers (Sanghvi, A. B. et al., 2005).

In several embodiments, ligands of a multi-ligand capture agent specific for a target are identified using the same target of the resulting multi-ligand capture agents. In particular, according to some embodiments, identification of ligands of the multi-ligand capture agent can be performed by selecting the ligands that are able to non-covalently attach to the target of choice at corresponding sites on the target, with the sites arranged to allow covalent linkage between each bound ligand and another.

In several embodiments, selecting a ligand can be performed from candidate ligands, for example by contacting candidate ligands with the target for a time and under condition to allow formation of a covalent linkage between the candidate ligands bound to the target, that is catalyzed by the target.

In several embodiments at least one of the candidate ligands is unrelated to at least one other candidate ligands and/or is unrelated to the target. In some embodiments all the candidate ligands provided are unrelated one to the other and/or to the target. In particular, in some embodiments, the candidate ligands comprise compounds initially not known to be able to bind the target.

In some embodiments, the candidate ligands comprise compounds initially known to be able to bind the target or a portion thereof.

In some embodiments, selecting a ligand can be performed based on a candidate ligand's known ability to bind the target and, in some of those embodiments, a specific site of interest on the target (e.g. an antibody binding site and a corresponding epitope). Additional features of the ligand associated with the ligand ability to bind the target (e.g. binding affinity and/or specificity) can also be considered in performing the selection.

In any case in some embodiments, selecting a ligand can be performed by designing ligands and/or the candidate ligands to select or introduce a desired feature on the ligands.

Exemplary desired features are those enabling or improving binding of the ligand with a target of choice and/or with specific sites within the target choice. For example in some embodiments, at least one of the two or more ligands can be modified to obtain binding at a specific site on the target (e.g. based on the ligand affinity and specificity for the site on the target). Also in some embodiments, a ligand can be designed to mimic a molecular structure (such as a nucleotidic sequence) that is specifically recognized by the target and more particularly by a specific site of interest on the target. In some embodiments, a ligand can be modified by insertion of one ore more functional groups on a candidate ligand to obtain the ability to specifically bind the target of interest. In some embodiments, a ligand can be pre-selected among candidate ligands based on the ability to specifically bind the target of interest or a specific site thereon resulting from a pre-screening procedure. In some of all of those embodiments, the ligand selection can also be based on the ability to bind a site of interest on a target with a predetermined affinity or selectivity.

Other exemplary desired features are dependent on the experimental design. For example in some embodiments, the ligand or candidate ligand can be designed to ensure that the resulting multi-ligand capture agent has water solubility. In particular, in some of those embodiments ligands can be designed to include ligand's building block of a hydrophilic nature, such as monomers which contain poly(ethylene) glycol, amine, carboxylic acid, hydroxyl, or azide functional groups. In other exemplary embodiments, ligands or candidate ligands can be designed to exhibit stability against biomolecular enzymes, such as proteases. In some of those embodiments, since biomolecular enzymes are highly selective to stereochemistry, sequence, and functional group, biologically resistant candidate ligands are designed according to such constraints. Non-natural amino acids include any D optical isomer of the naturally occurring amino acids, and are exemplified in the libraries of Example 2. Artificial amino acids indicate molecules that can be readily coupled together using standard amino acid coupling chemistry, but with molecular structures that do not resemble the naturally occurring amino acids. Fmoc-Az4-OH, Fmoc-Az8-OH, and Fmoc-D-Pra-OH of Example 1 are exemplary artificial amino acids.

Additional desired features to be selected or introduced on a ligand or candidate ligand are those enabling or improving a ligand or candidate ligand's ability to link with other ligands in a multi-ligand capture agent.

In particular, in multi-ligand capture agents herein described, covalent linkage among pairs of ligands is performed by functional groups presented on the ligands so that, upon binding of the two individual ligands with the target, those functional groups react to form a covalent bond.

The term "functional group" as used herein indicates specific groups of atoms within a molecular structure that are responsible for the characteristic chemical reactions of that structure. Exemplary functional groups include hydrocarbons, groups containing halogen, groups containing oxygen, groups containing nitrogen and groups containing phosphorus and sulfur all identifiable by a skilled person. In particular, functional groups in the sense of the present disclosure include a carboxylic acid, amine, triarylphosphine, azide, acetylene, sulfonyl azide, thio acid and aldehyde. In particular, for example, the first functional group and the second functional group can be selected to comprise the following binding partners: carboxylic acid group and amine group, azide and acetylene groups, azide and triarylphosphine group, sulfonyl azide and thio acid, and aldehyde and primary amine. Additional functional groups can be identified by a skilled person upon reading of the present disclosure. As used herein, the term "corresponding functional group" refers to a functional group that can react to another functional group. Thus, functional groups that can react with each other can be referred to as corresponding functional groups.

The term "present" as used herein with reference to a compound or functional group indicates attachment performed to maintain the chemical reactivity of the compound or functional group as attached. Accordingly, a functional group presented on a ligand, is able to perform under the appropriate conditions the one or more chemical reactions that chemically characterize the functional group.

Figure 3:
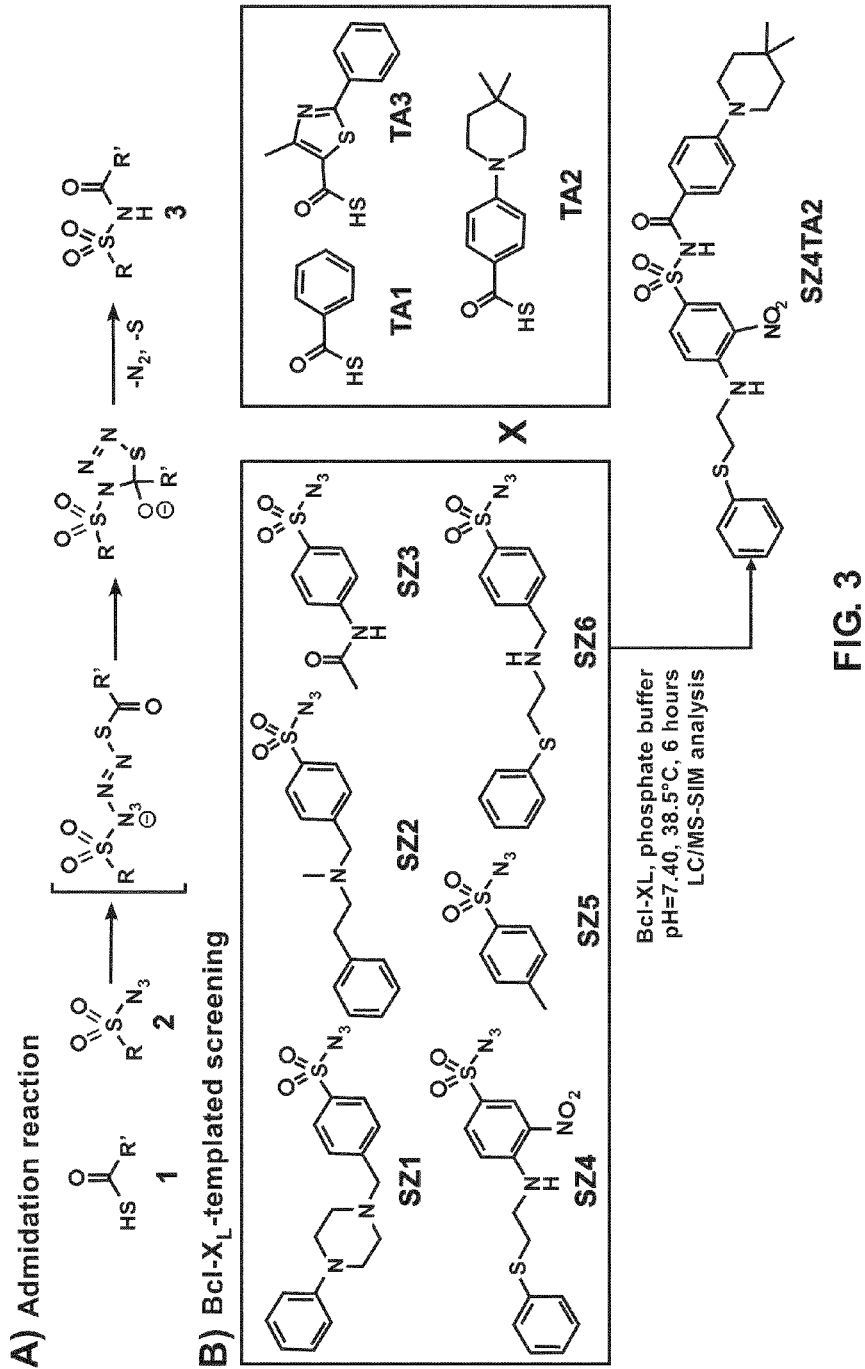
FIG. 3 shows a schematic representation of a covalent linkage according to some embodiments herein described.
Figure 4:
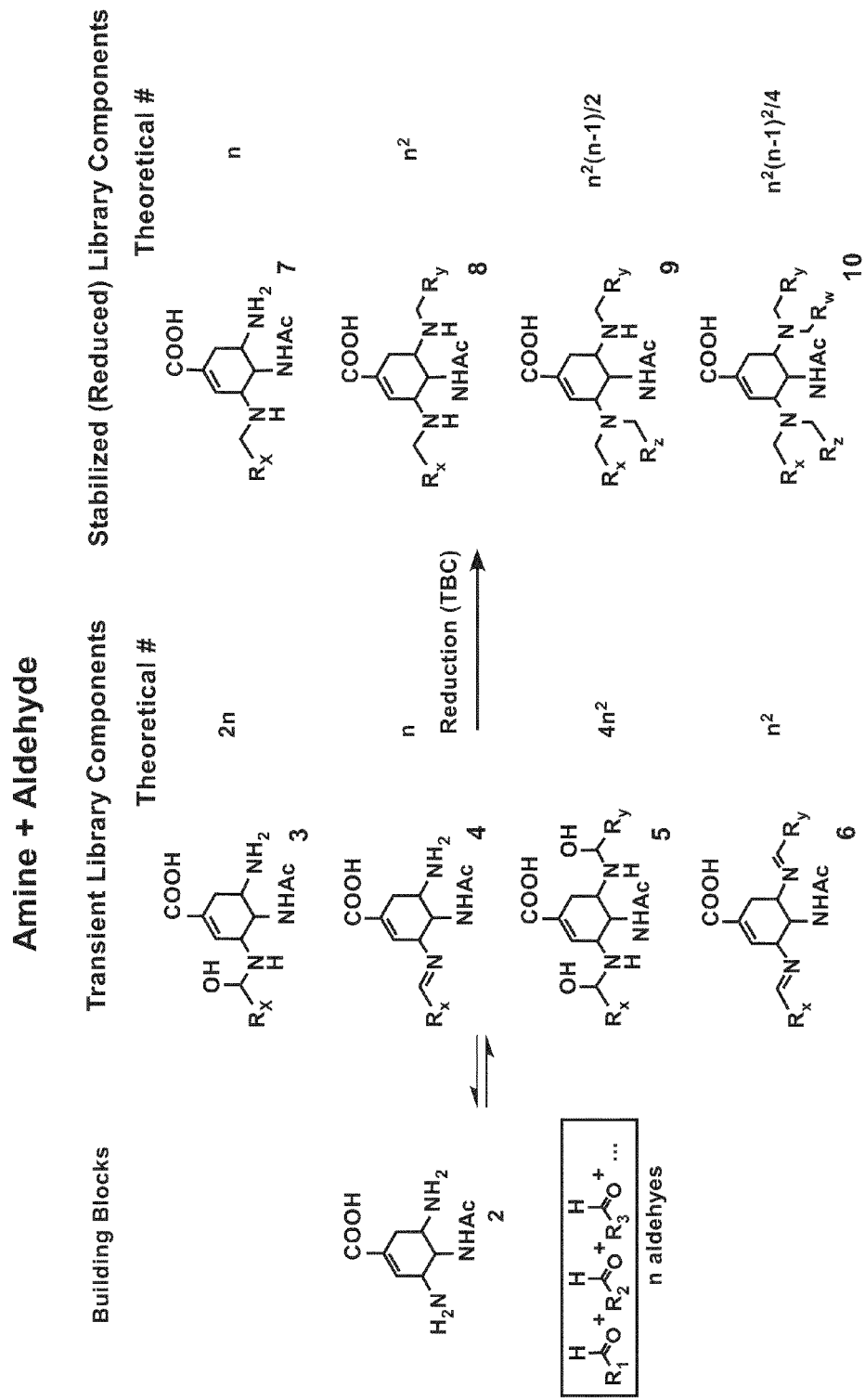
FIG. 4 shows a schematic representation of a covalent linkage according to some embodiments herein described.

In particular, in embodiments where two or more ligands are covalently linked by modified Staudinger ligation the functional groups are formed by azide and triarylphosphine and the reaction is a chemoselective ligation which produces a stable covalent adduct by forming an amide bond between azide and triarylphosphine groups in even aqueous environments (FIG. 1). In embodiments, wherein two or more ligands are covalently linked by a bio-orthogonal amidation reaction, the functional groups are formed by a sulfonyl azide and a thio acid which are reacted to form an acylsulfonamide (FIG. 3). In embodiments, wherein two or more ligands are covalently linked by reduction of transient hemiaminals and imines the functional groups are formed by the interaction between an aldehyde and a primary amine (FIG. 4).

Figure 2:
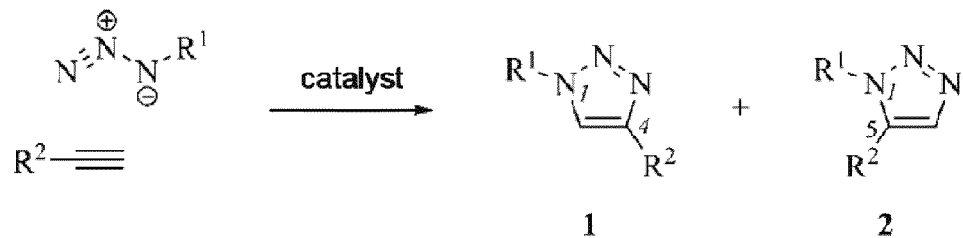
FIG. 2 shows a schematic representation of a covalent linkage according to some embodiments herein described.

In embodiments, wherein two or more ligands are covalently linked by a bio-orthogonal 1,3-dipolar Huisgen cycloaddition reaction, the functional groups are formed by an azide and acetylene which are reacted to form a 1,2,3-triazole group (FIG. 2).

In some embodiments, the functional group is originally presented in the selected ligand or candidate ligand. In some embodiments, presentation of a functional group for linkage of the ligand with another is a desired feature that is introduced in a ligand or candidate ligand. In particular, in some of those embodiments, it is possible to modify a ligand or candidate ligand to introduce a functional group that specifically allows covalent linkage between the candidate ligand and another ligand.

In some embodiments, functional groups presented on ligands and/or candidate ligands for linkage with another ligand are unreactive towards the target of interest and functional groups presented thereon (e.g. azide and triarylphosphine to be linked in a modified Staudinger ligation when the target is a biological target (E. Saxon et al. in *Science* (2000), Vol. 287, 2007-2010, incorporated herein by reference in its entirety).

In several embodiments, the selected ligand comprises at least an anchor or primary ligand and at least one secondary ligand, which can be selected for their affinity for the target using methods herein described.

In particular, a primary ligand can be selected from a plurality of candidate primary ligands by contacting the candidate ligands with the target and by selecting the candidate primary ligands that specifically bind the target to form a candidate ligand target complex.

A secondary ligand can then be selected by contacting a plurality of candidate secondary ligands with a primary ligand target complex for a time and under conditions to allow formation of a secondary ligand primary ligand target complex and selecting the secondary ligand that specifically binds the primary ligand target complex and covalently links with the primary ligand.

In particular, a primary ligand can be optionally modified to introduce a first functional group capable of specifically binding to a corresponding second functional group in a reaction catalyzed by the target. The modified primary ligand can then be contacted with the target to form a modified primary ligand target complex that is used to select the secondary ligand.

Additional ligands can further be selected with similar approaches directed to identify a tertiary ligand, a quaternary ligand and so on for as many ligands as desired according to the experimental design.

In several embodiments, the at least two of the various plurality of candidate ligands (e.g. candidate primary ligands, candidate secondary ligands, candidate tertiary ligands, etc.) can differ between each other. In particular, a plurality of candidate ligands can be selected using information derived from a previous selection of candidate ligands. For example, the plurality of candidate secondary ligands can be selected using information derived from the plurality of first candidate ligands to increase the affinity of the candidate ligands from the plurality of candidate secondary ligands.

In several embodiments, at least one of the plurality of candidate ligands is attached to a substrate. The term "attach" or "attached" as used herein, refers to connecting or uniting by a bond, link, force or tie in order to keep two or more components together, which encompasses either direct or indirect attachment where, for example, a first molecule is directly bound to a second molecule or material, or one or more intermediate molecules are disposed between the first molecule and the second molecule or material. The term "substrate" as used herein indicates an underlying support or substratum. Exemplary substrates include solid substrates, such as glass plates, microtiter well plates, magnetic beads, silicon wafers and additional substrates or surfaces identifiable by a skilled person upon reading of the present disclosure.

In particular, in some embodiments, each plurality of candidate ligands is attached to different substrates or portions of a substrate so that complexes including each candidate ligand can be detected separately from another. In some of those embodiments, the candidate ligands are attached to beads with each of the candidate ligands specifically attached to a single bead in a one-ligand-one-bead arrangement. In another embodiment, the candidate ligands are attached to specific locations on a surface, with each of the candidate ligands specifically attached to a predefined location in a one-ligand-one-location arrangement.

In particular, in several embodiments, selection of ligands for a multi-ligand capture agent, can be performed with the aid of libraries. For examples, primary and secondary candidate ligands can be provided in libraries that are then screened with the target molecule and/or with complex of the target molecule with selected primary ligands.

In embodiments wherein ligands to be included in the multi-ligand capture agent comprise a polypeptide and, in particular peptides, a protein library can be used to identify the ligands, that includes candidate polypeptides, such as 3 to 10 monomers peptides presented for screening. In particular, in some embodiments, candidate ligands can be presented on a One-Bead-One-Compound (OBOC) peptide library using the approaches described for example in Lam, K. S. et al., 1997; Furka, A. et al., 1991; Geysen, H. M. and T. J. Mason, 1993 each incorporated herein by reference in its entirety. Additional library can be used which are identifiable by a skilled person upon reading of the present disclosure. Detection of hits following contact with the target of interest can be performed according to several methods identifiable to a skilled person which include methods further illustrated in the examples section.

Figure 9:
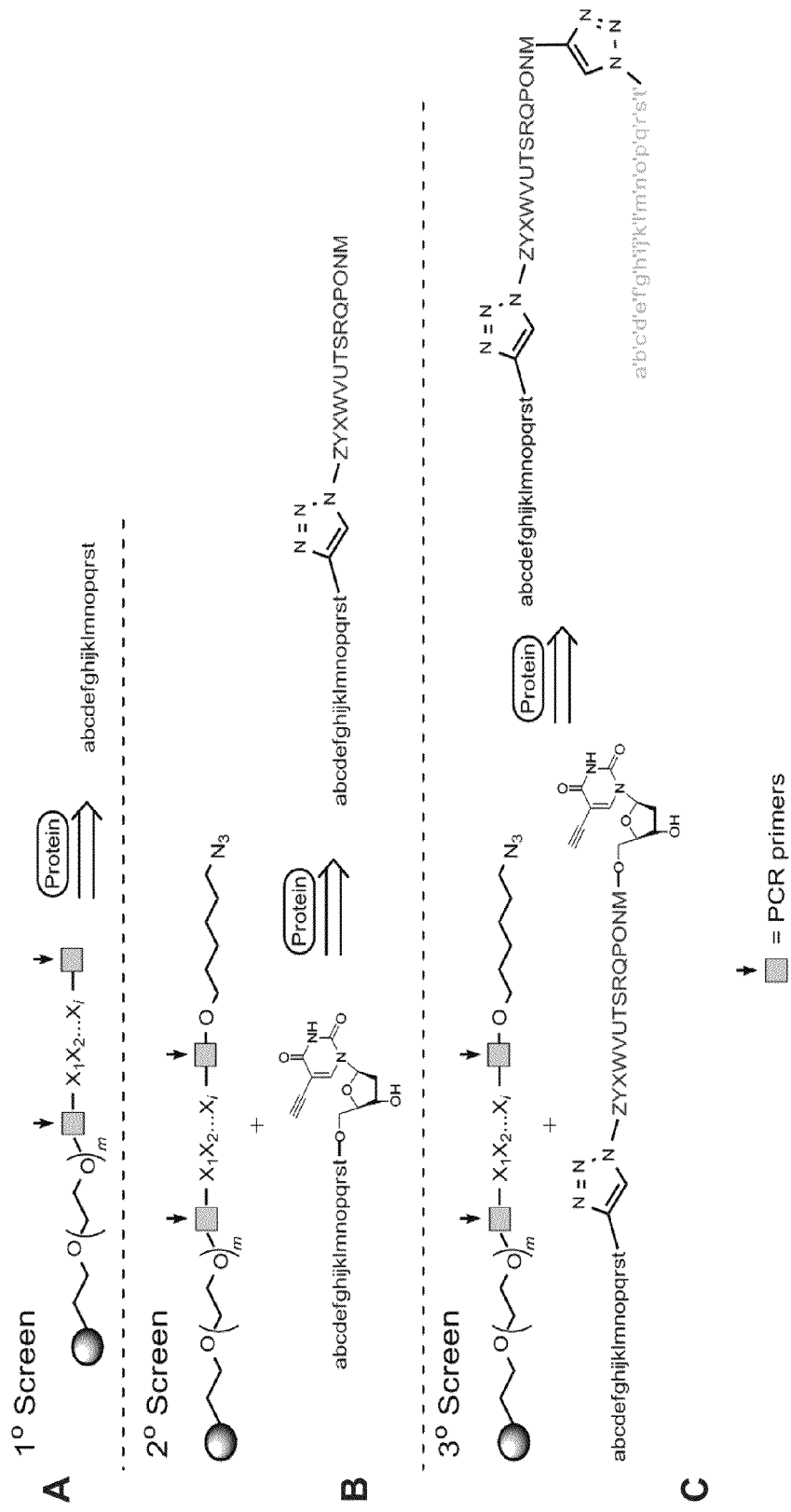
FIG. 9 shows a schematic representation of a method for sequential assembly of a polynucleotide multi-ligand capture agent according to an embodiment herein described. Panel A shows a first step of contacting a plurality of polynucleotides with a labeled target to identify a primary ligand or anchor ligand. Panel B shows a second step of contacting the primary ligand from the first step with the same plurality of polynucleotides now appended with a linker to identify a secondary ligand and obtain a biligand formed by the primary ligand of the first step and the secondary ligand. Panel C shows a third step of repeating by employing the biligand formed from the second step, as the new primary ligand to allow identification of higher order multi-ligands.

In embodiments wherein ligands to be included in the multi-ligand capture agent comprise a polynucleotide, and in particular oligonucleotides (see FIG. 9), libraries of oligonucleotide ligands can be synthesized to identify the ligands, for example using the one-bead one-oligonucleotide ($S$—ODN or $S_2$—ODN) method using standard phosphoramidite and thiophosphoramidite chemistry on polystyrene beads (Yang, X. et al., 2002). In particular, in those embodiments, each ligand of a polynucleotide capture agent can typically comprise 20-30 nucleotides in length. Detection of hits following contact with the target can be performed with sequence that include but are not limited to sequencing of hits made possible by incorporation of 5' and 3' fixed primer sequences, flanking the combinatorial library segment of the oligonucleotide ligand, which allow for downstream PCR amplification prior to sequencing. The diversity elements of the bead-based S—ODN library can be increased from the standard monomers (e.g., A, T, G, C, U) to include non-natural monomers presenting one or more functional groups, which can include acetylene-bearing pyrimidine triphosphates (Gramlich, P. M. E. et al., 2008) and 5'-bromohexyl phosphoramidites (which are rapidly converted to 5'-azidohexyl modified monomers on-bead by treatment with sodium azide). Non-natural modification increases the nuclease stability of these capture agents, and also provides the functional groups for building multi-ligands from individual primary ligands. Secondary ligands are selected by contacting a plurality of candidate ligands (modified with a second functional group) with a primary ligand/target complex to allow specific binding and covalent reaction between the two ligands. These functional groups can be azide and acetylene (as shown in FIG. 9), but can also include functional groups like those shown in FIG. 1 or FIG. 3. Tertiary, quaternary, etc. ligands are identified by similar methods.

Figure 10:
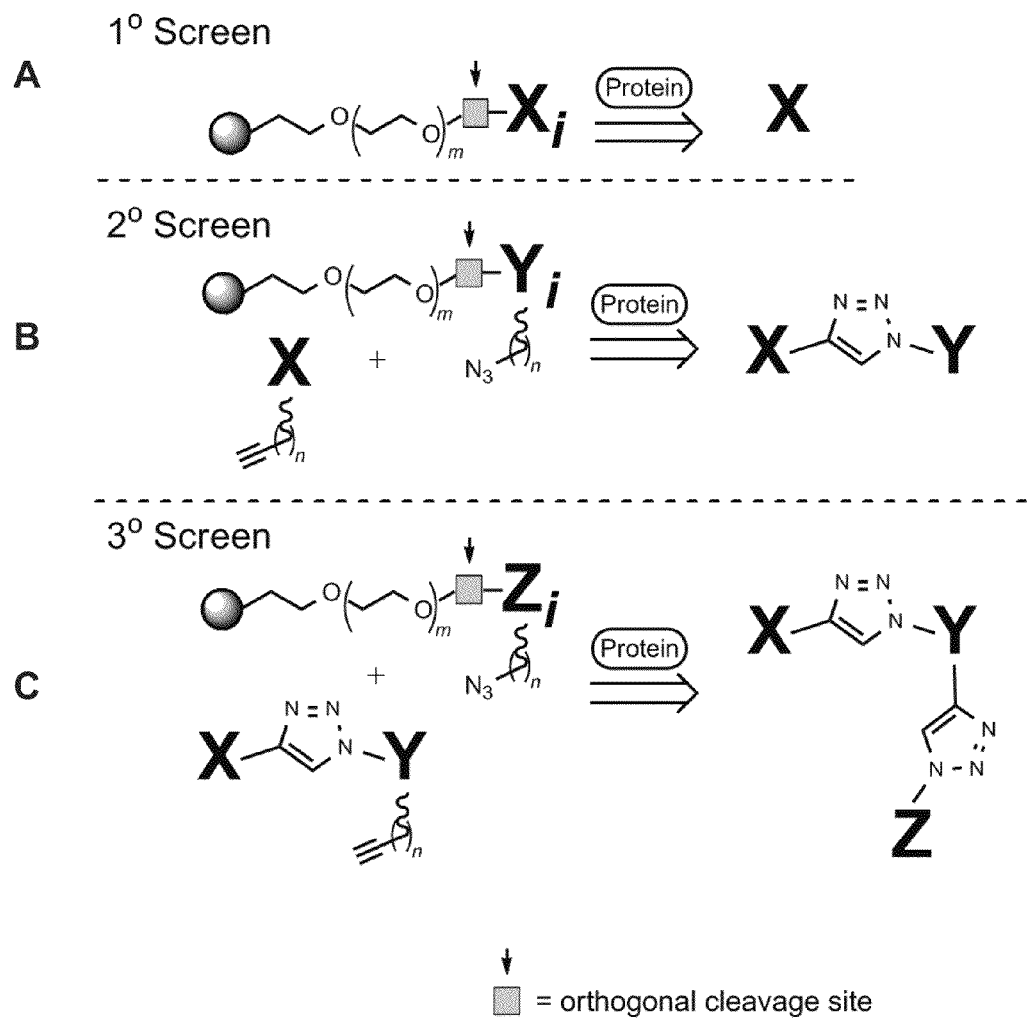
FIG. 10 shows a schematic representation of a method for sequential assembly of a small molecule multi-ligand capture agent according to an embodiment herein described. Panel A shows a first step of contacting a plurality of small molecules with a labeled target to identify a primary ligand or anchor ligand. Panel B shows a second step of contacting a primary ligand from the first step with the same library now appended with a linker to identify a secondary ligand and obtain a biligand formed by the primary ligand of the first step and the secondary ligand. Panel C shows a third step of repeating by employing the biligand formed from the second step, as the new primary ligand to allow identification of higher order multi-ligands.
Figure 11:
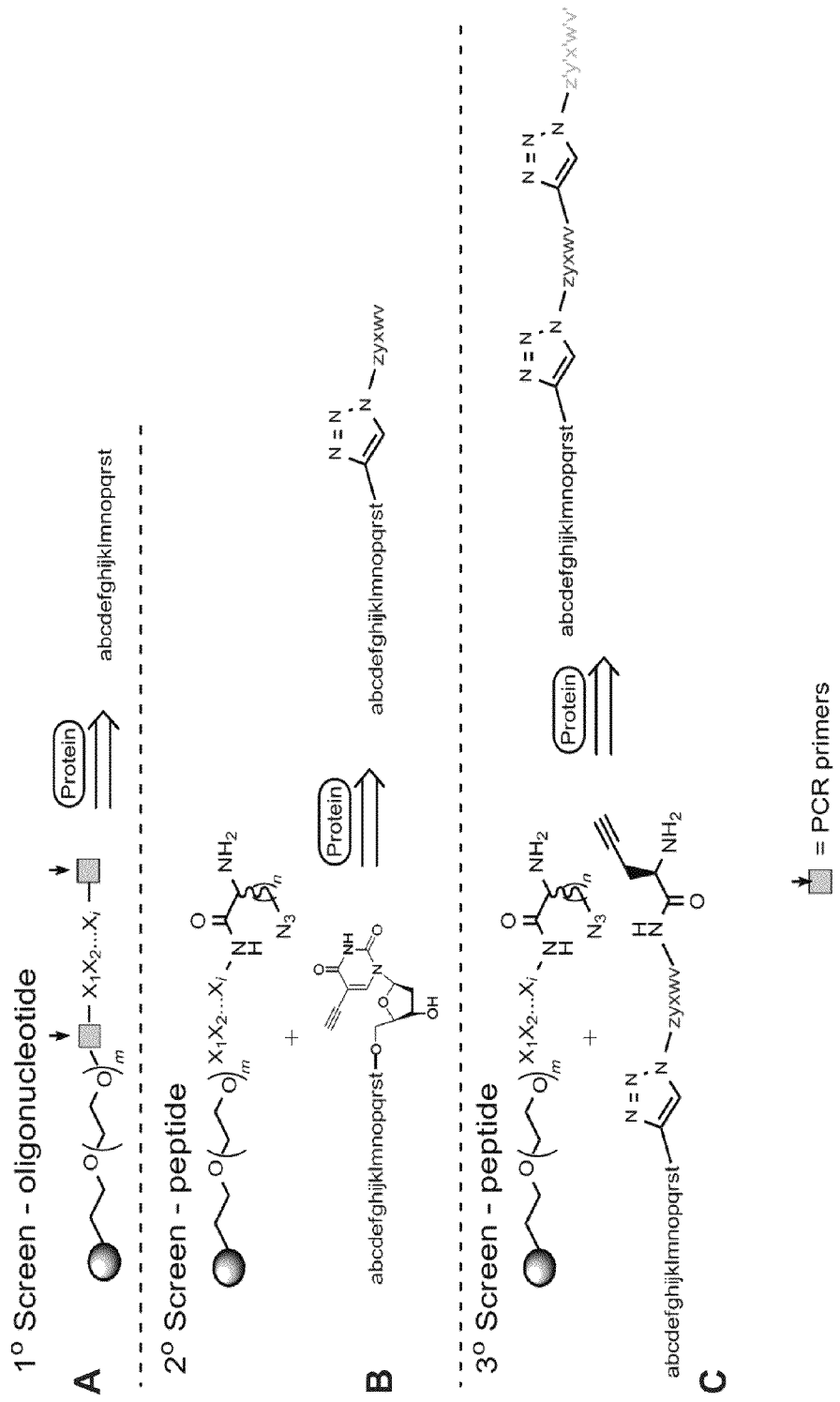
FIG. 11 shows a schematic representation of a method for synthesizing a chimeric multi-ligand capture agent by sequential assembly of ligands of different chemical nature. Panel A shows a first step of contacting of a library of polynucleotides with a labeled target to identify a primary ligand or anchor ligand. Panel B shows a second step of contacting a primary ligand from the first step with a peptide library now appended with a linker to identify a secondary ligand and obtain a biligand formed by the primary ligand of the first step and the secondary ligand. Panel C shows a third step of repeating by employing the biligand formed from the second step, as the new primary ligand to allow identification of higher order multi-ligands by contacting the same or another peptide library of Panel B.
Figure 12:
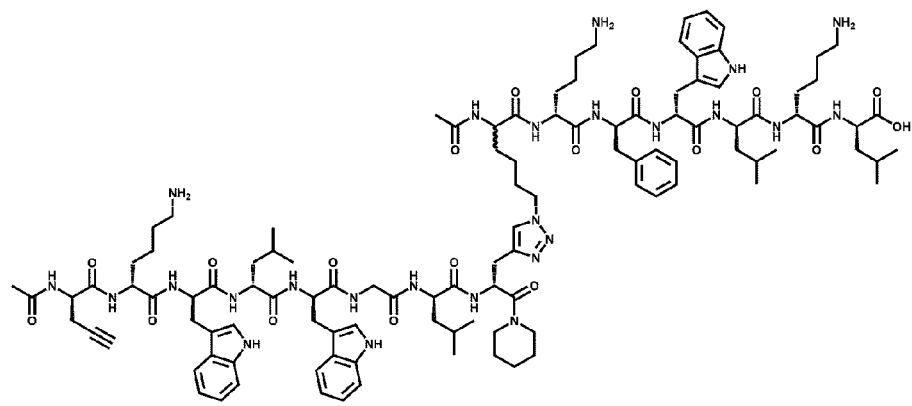
FIG. 12 shows the structural formula of a deprotected biligand anchor according to an embodiment herein described. In particular, a deprotected biligand anchor of FIG. 12 is composed of the original sequence of a biligand capture agent, with one additional functional group to serve as the attachment site for building the triligand capture agent. The deprotected biligand anchor of FIG. 12 also contains 15 non-natural and artificial amino acids, and displays a single parent mass.
Figure 13:
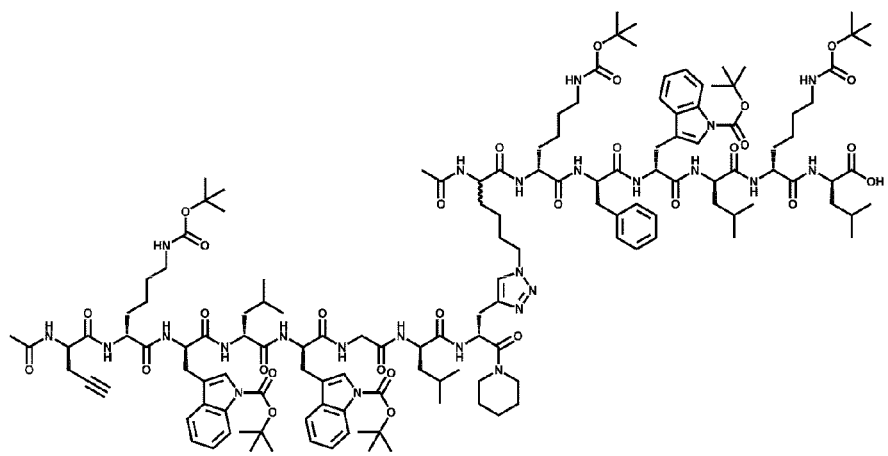
FIG. 13 shows the structural formula of a fully protected biligand anchor according to an embodiment herein described. The fully protected biligand anchor of FIG. 13 maintains protection of amino acid side chains in the biligand anchor and can be used for synthesis of multi-ligand capture agents in bulk quantities. The fully protected biligand anchor of FIG. 13 also can be synthesized with high purity as a 15-mer sequence.

In embodiments wherein ligands to be included in the multi-ligand capture agent comprise a small molecule, libraries of small molecules can be prepared by standard solid-phase organic synthesis (SPOS) and a one-bead one-molecule method. Each ligand of small molecule capture agent can comprise one (as shown in FIG. 10) or more than one molecular building blocks. Libraries typically contain several tens of building blocks resulting in $10^2$ to $10^3$ ligands. Decoding of hits is made possible by releasing the contents of a single bead by a photocleavable (e.g., 2-nitrophenyl) or CNBr-cleavable (e.g., methionine) linker, followed by mass spectrometry. Alternatively, encoding by molecular tags after each combinatorial step allows for hit decoding by indirect means (Baldwin, J. J. et al., 1995). Each primary ligand of a small molecule capture agent is synthesized to present a functional group. Secondary ligands are selected by contacting a plurality of candidate ligands (modified with a second functional group) with a primary ligand/target complex to allow specific binding and covalent reaction between the two ligands. These functional groups can be azide and acetylene (as shown in FIG. 10), but can also include functional groups like those shown in FIG. 1 or FIG. 3 or FIG. 4. Tertiary, quaternary, etc. ligands are identified by similar methods. In some cases, the functional groups can specifically bind to the target and become an integral part of the capture agent. Small molecule capture agents can have efficacy as drugs.

Figure 7:
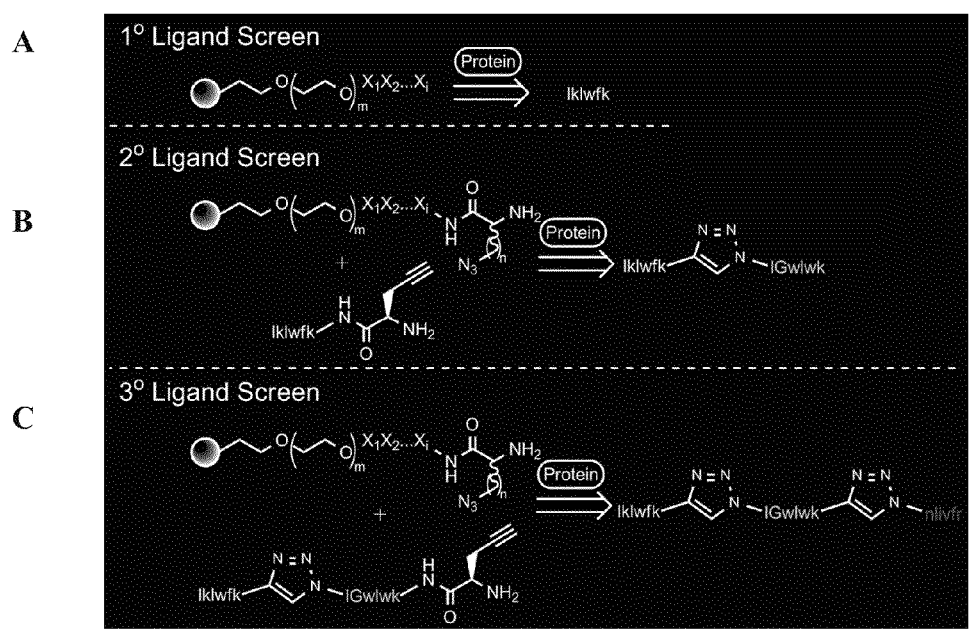
FIG. 7 shows a schematic representation of a method to prepare a multi-ligand capture agent according to several embodiments herein described. Panel A shows a first step of contacting of plurality of candidate molecules in a library with a labeled target to identify a primary ligand or anchor ligand. Panel B shows a second step of contacting a primary ligand from the first step with the same library now appended with a linker to identify a secondary ligand and obtain a biligand formed by the primary ligand of the first step and the secondary ligand. Panel C shows a third step of repeating by employing the biligand formed from the second step, as the new primary ligand to allow identification of higher order multi-ligands.
Figure 8:
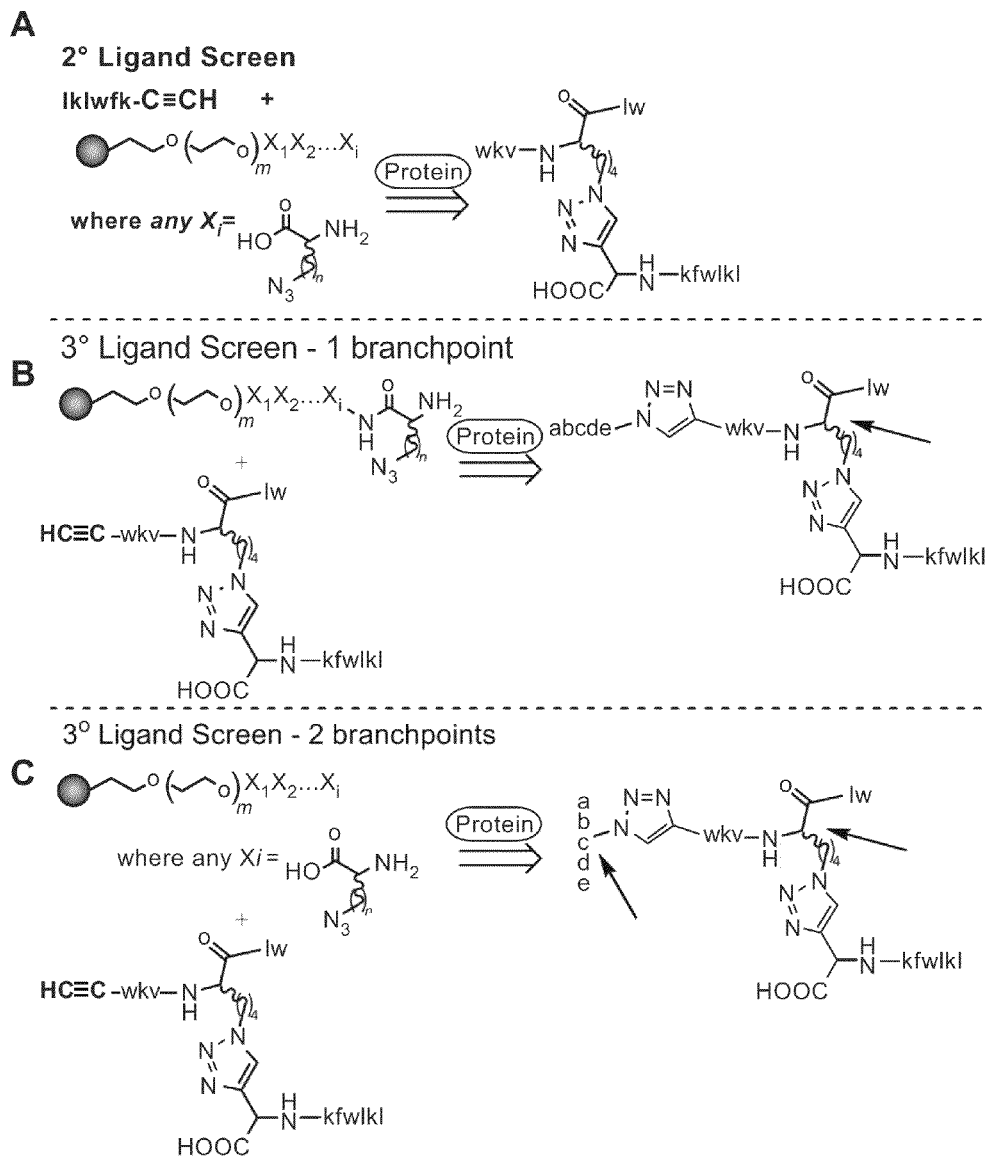
FIG. 8 shows a schematic representation of a method to prepare a branched multi-ligand capture agent according to several embodiments herein described. Panel A shows a first step of contacting of a library with a labeled target and an anchor ligand presenting a first functional group (identified by the method of FIG. 7A) to identify a secondary ligand. This library of secondary ligands contains multiple sites of substitution by a second functional group. The result of such screen is a biligand comprised of a secondary ligand connected by an internal branchpoint. This branched biligand may be further modified with a functional group and utilized as an anchor in a branched triligand screen. Panel B shows a second step of contacting this branched biligand anchor with a comprehensive library now appended with a linker to identify a tertiary ligand in a multi-ligand capture agent with one branchpoint. Panel C shows the same step performed to identify a tertiary ligand in a multi-ligand capture agent with 2 branchpoints. The methods of Panels A, Panel B and/or Panel C may be optionally repeated to obtain multi-ligands comprised of n-branchpoints and n-ligands.

In embodiments wherein multi-ligand capture agents are formed by chimeric capture agents, such as small-molecule/peptide, small-molecule/polynucleotide, and polynucleotide/peptide (see e.g. FIG. 11 for one scheme), the relevant ligands are identified by a method that combines specific steps related to the identification of a ligand of the desired chemical nature such as the ones described above (see also FIG. 9 for polynucleotides, FIG. 10 for small molecules, and FIGS. 7 and 8 for peptides). In those embodiments, the overall method to identify the ligands and possibly produce the capture agent is similar to the one used for other capture agents in that a sequential assembly of multi-ligands occurs via contacting the target with two individual ligands synthesized to display complementary functional groups and facilitating the reaction between them. Efficient peptide coupling to an oligonucleotide has been shown previously (Halpin, D. R. et al., 2004), which demonstrates that synthesis of chimeric multi-ligand capture agents in bulk quantities is feasible. Any of the chimeric multi-ligand capture agents can have a branched composition if a functional group is presented at an internal site of one or more ligands. Chimeric capture agents can efficiently interact with proteins having multiple epitopes of a diverse chemical nature, such as a protein that contains two binding pockets (e.g., one pocket for DNA-binding and a second pocket for binding to other proteins).

In embodiments where multi-ligand capture agents are branched capture agents a branched structure can be obtained by presentation of a functional group at an internal site of one or more ligands composing the capture agent, independently from the chemical nature of the ligand. In embodiments where multi-ligand capture agents are linear capture agents functional groups can instead be presented at one of the ends of the ligand.

In embodiments, where ligands are linked with bio-orthogonal 1,3-dipolar Huisgen cycloaddition reaction between an azide and acetylene, large libraries (such as the one illustrated in FIG. 7) are screened for specific interaction with the target. The best-binding ligands are modified with an acetylene functional group and become "anchor ligands." In a second screen, the acetylene-modified anchor ligand is incubated in the presence of the comprehensive bead library of secondary ligands appended with an azide functional group. The result of this screen is a "biligand" formed by the covalent 1,2,3-triazole linkage between the two ligands contacting the target. That biligand can serve as a new anchor ligand (with acetylene modification), and the same bead library is employed to identify the tertiary ligand of a triligand capture agent, and so forth. Conversely, if the anchor ligands contain azide functional groups, then the secondary, tertiary, etc. ligand candidates can contain acetylene functional groups. As used herein, the term "anchor ligand" refers to a ligand to which a second ligand is coupled. Generally, in the context of the disclosed methods, the second ligand is covalently linked to the anchor ligand in a target-catalyzed reaction.

In embodiments, where ligands are linked with modified Staudinger ligation, libraries to synthesize a multi-ligand capture agent can be constructed according to an approach similar to those exemplified in FIG. 7, with the exception that the anchor ligands of the 1° and 2° screens are functionalized with triarylphosphine and not an acetylene group.

In embodiments, where ligands are linked with amidation reaction, libraries to synthesize a multi-ligand capture agent can be constructed according to an approach similar to those exemplified in FIG. 7, with the exception that the anchor ligands of the 1° and 2° screens are functionalized with a thio acid and not an acetylene group and the bead libraries are modified with sulfonyl azide functional groups. Alternatively, the polarity can be reversed, with the anchor ligands attached to sulfonyl azide functional groups and the bead libraries attached to the thio acid.

In embodiments, where ligands are linked by reductive amination, libraries to synthesize a multi-ligand capture agent can be constructed according to an approach similar to those exemplified in FIG. 7, with the exception that the anchor ligands of the 1° and 2° screens are functionalized with an aldehyde and not an acetylene group and the bead libraries are modified with amine functional groups (e.g. the N-terminus of a peptide ligand). Alternatively, the polarity can be reversed, with the anchor ligands attached to amine functional groups and the bead libraries attached to the aldehyde.

In some embodiments, the two or more ligands of the multi-ligand capture agent for a target can be provided in a multi-ligand using methods herein described that can comprise selecting candidate ligands capable of specifically binding the target at corresponding binding sites, wherein the binding sites are so arranged on the target to allow covalent linkage between each ligand bound on each site with another. In several embodiments at least one of the candidate ligands is unrelated to at least one other candidate ligand and/or is unrelated to the target. As used herein, the term "corresponding binding site" refers to the binding site of a molecule on another molecule. Thus, the site on a target where a given ligand binds can be said to be a corresponding binding site for the ligand.

In particular in some embodiments, the candidate ligands comprise a first plurality of candidate ligands and a second plurality of candidate ligands, each possibly including at least one ligand unrelated to at least one other ligand of the plurality of candidate ligand and/or unrelated to the target. In those embodiments, selecting a ligand can be performed by: contacting the target with the first plurality of candidate ligands to select an anchor ligand that specifically binds the target and presents a first functional group capable of specifically binding a corresponding second functional group in a reaction catalyzed by the target. The anchor ligand thus provided can then be contacted with the target to provide an anchor ligand target complex; that is then contacted to the second plurality of candidate ligands, presenting the second functional group. Candidate ligands of the second plurality of candidate ligands are then selected that specifically bind the anchor ligand target complex and covalently link the anchor ligand, thus providing a multi-ligand. Optionally selecting candidate ligands can be repeated, using the multi-ligand as an anchor ligand to add additional ligands to the multi-ligand.

In particular, in some embodiments selection of an anchor ligand can be performed by selecting candidate ligands which specifically bind the target; and modifying the selected candidate ligands to introduce a first functional group capable of specifically binding a corresponding second functional group in a reaction catalyzed by the target, thus providing an anchor ligand presenting the first functional group.

In some embodiments, selecting candidate ligands can be repeated using the multi-ligand as an anchor two or more, three or more, four or more, five or more, six or more, or seven or more times to add additional ligands to the multi-ligand.

In some embodiments, selecting candidate ligands is repeated using the multi-ligand as an anchor until the binding affinity to the target of the higher order multi-ligand capture agent is at least $10^2$, at least $10^3$, at least $10^4$, at least $10^5$, at least $10^6$, at least $10^7$, at least $10^8$, at least $10^9$, at least $10^{10}$, at least $10^{11}$, at least $10^{12}$, or at least $10^{13}$ higher that the binding affinity of the anchor ligand. As used herein, higher order multi-ligand capture agents refer to multi-ligand capture agents with three or more ligands. In some embodiments of the disclosed methods of identifying and producing multi-ligand capture agents, a third, fourth, fifth, sixth, seventh, etc. ligand can be added to a biligand capture agent. This can be accomplished by, for example, repeating the target-catalyzed addition step using a multi-ligand capture agent as the anchor ligand. The resulting multi-ligand capture agents are higher order multi-ligand capture agents. Multi-ligand capture agents having two, three, four, five, six, and seven ligands can be referred to as biligand, triligand, tetraligand, pentaligand, hexaligand, and heptaligand, respectively.

In some embodiments, selecting candidate ligands are repeated until the dissociation constant for the binding of the multi-ligand capture agent to the target is equal to or less than $10^{-6}$ M, $10^{-7}$ M, $10^{-8}$ M, $10^{-9}$ M, $10^{-10}$ M, $10^{-11}$ M, $10^{-12}$ M, $10^{-13}$ M, $10^{-14}$ M, $10^{-15}$ M, or $10^{-16}$ M.

In some embodiments, the first and second plurality of candidate ligands are the same or different as a whole or in part.

In some embodiments, a same or different plurality of candidate ligands is used as the second plurality of candidate ligands in one or more, and possibly all, of the iterations of selecting candidate ligands wherein selection of an anchor ligand is performed by selecting candidate ligands which specifically bind the target; and modifying the selected candidate ligands to introduce a first functional group.

In some embodiments, a same or different functional group is used as first and/or second functional group in one or more, and possibly all, of the iterations of selecting candidate ligands wherein selection of an anchor ligand is performed by selecting candidate ligands which specifically bind the target; and modifying the selected candidate ligands to introduce a first functional group In some embodiments in which the two or more ligands are formed by a peptide or polypeptide, the multi-ligand capture agent can form a multi-ligand capture agent of a protein nature, and the method above can be used to synthesize the multi-ligand capture agent of a protein nature.

In some embodiments, a procedure can be performed that is exemplified in the examples section with reference to peptide ligands, protein target and triazole linkage. A skilled person will understand that the process can be performed with other ligands, target molecules and covalent linkages mutatis mutandis.

According to the procedure a peptide anchor ligand can be identified using a first large peptide library that can be prepared using peptides synthesized according to procedures known to the skilled person. In particular, using screening methods, the peptide anchor ligand is chosen among the peptides of the first library for having a predetermined affinity against a protein of interest. In particular, the selection procedure for the peptide anchor ligand can include a sequence selection to achieve a desired affinity and/or selectivity of the peptide anchor ligand.

A secondary ligand can then be identified by using a second, large peptide library that can be prepared from the same (or even different) types of amino acid building blocks as the first library. If the peptide anchor ligand has one or more azide-functionalized amino acids, then the peptides from the second library will contain at least one or more acetylene-functionalized artificial amino acids. A second screen is carried out that involves the second peptide library against the same protein, but in the presence an excess amount of the peptide anchor ligand. Only those secondary ligands that can be brought into contact with the protein surface and the peptide anchor ligand in just the correct orientation will react to form the 1,2,3-triazole linkage. Thus, the protein surface provides the catalyst for this process by orienting the anchor ligand and the secondary ligand correctly with respect to each other and with respect to the protein surface.

Figure 19:
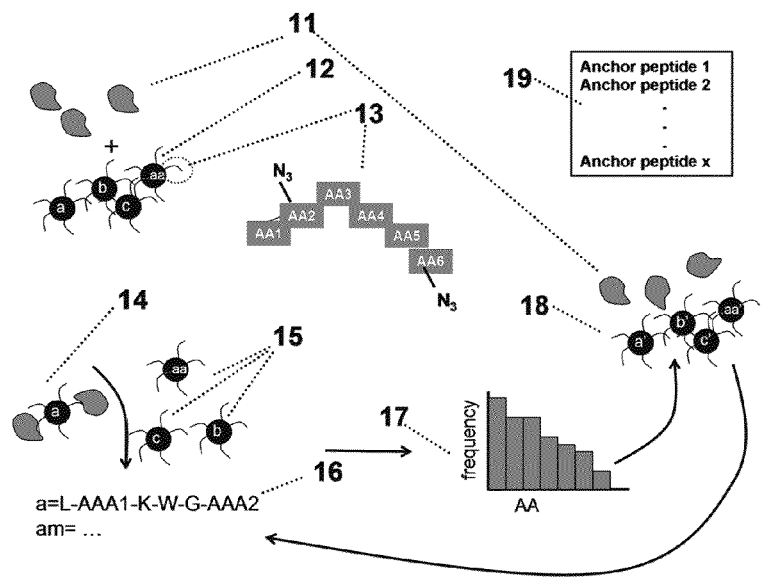
FIG. 19 shows a schematic representation of a method to identify an anchor ligand according to some embodiments herein described.

A method for identifying a peptide anchor ligand according to some embodiments herein described is schematically illustrated in FIG. 19. In particular, in the illustration of FIG. 19 a fluorescently labeled protein of interest (11) is screened against a library of peptides (12).

That library can be constructed on beads, using one-bead one-compound (OBOC) approaches (Lam, K. S. et al., 1997; Furka, A. et al., 1991; Geysen, H. M. and T. J. Mason, 1993). In this way, each bead contains a unique peptide (13), and that peptide is comprised of amino acids that are naturally occurring amino acids, non-natural amino acids (D-stereoisomers), or artificial amino acids (which can contain azide or acetylene functionalities).

The library itself is assembled using standard coupling chemistries (Carpino, L. A. et al., 1994). The protein (11) and the library (12) are incubated for a period of time at a particular protein concentration, and the 'hit' beads (14) are identified by their fluorescence. Typically 0.1% or less of the beads are identified as hit beads, and are separated from the non-hit beads (15). The protein is removed from the beads using standard chemistries, and the peptides on the beads are sequenced using methods such as Edman degradation (Laursen, R. A. 1971) or mass spectrometry (Wang, X. et al., 2005; Lewis, J. K. et al., 2000).

Once the peptide sequences (16) are identified, a histogram (17) that correlates the amino acid frequency versus amino acid identity is prepared. A second, more focused library (18) that uses those most commonly identified amino acids can then be prepared, re-screened against the protein (11), and the hit beads are again identified by their peptide sequence (16). This second library can contain slightly longer peptides, and the screening process can involve a lower concentration of the protein (11). This process can be repeated until one or more peptide anchor ligands (19) of the desired affinity are achieved. Those peptides are then prepared in bulk quantities for the second stage in the screening process, in which a biligand capture agent is identified. Other methods for identifying anchor ligands can be used, each with their own advantages and disadvantages. For example, a peptide can be identified using phage display methods (Smith, G. P. and V. A. Petrenko, 1997), and then that peptide can be modified with azide or acetylene-containing artificial amino acids to produce a focused library, which is then screened against the protein of interest. Other approaches are equally applicable. The affinity of the peptide anchor ligand will depend upon the number of amino acids in the peptide, and upon the protein against which it is screened, among other factors. In several embodiments, for capture agents such as a 6- or 7-mer peptide, affinities in the order of $10^{-4}$-$10^{-6}$ M are typically achievable, which are at least commensurate with certain capture agents of the art.

Figure 20:
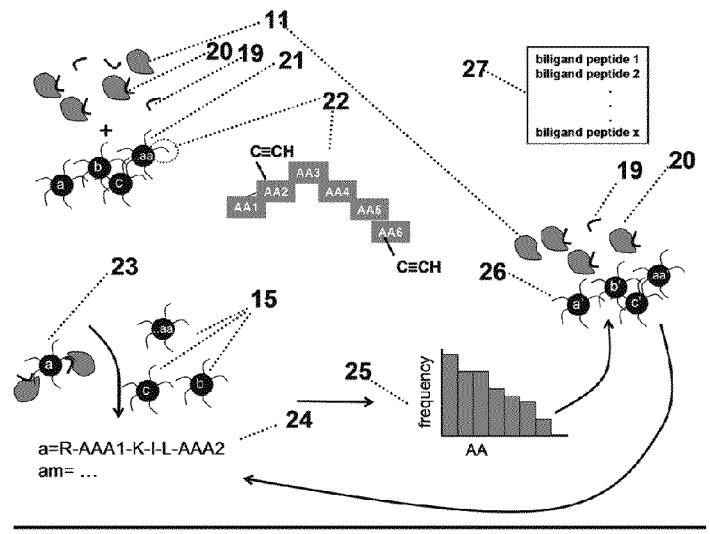
FIG. 20 shows a schematic representation of method to identify a secondary ligand according to some embodiments herein described.

Identification of the secondary ligand and formation of a biligand capture agent can be then performed according to the method schematically illustrated in FIG. 20 which illustrates the approach according to some embodiments herein described. One of the peptide anchor ligands (19) from the above described screening procedure is added to a solution containing the protein of interest (11) at a concentration that depends upon the binding affinity of that peptide anchor molecule. Typically, for a binding affinity of $10^{-6}$ M, a concentration of a few to ten micromolar suffices.

The peptide anchor ligand/protein solution is then screened against the library of candidate secondary ligands (21). This library is constructed similar to the candidate library for peptide anchor ligands (12), with the exception that some of the artificial amino acid components (22) contain acetylene functionalities for the case of an azide-functionalized peptide anchor ligand. Conversely, if the peptide anchor ligand contains acetylene-functionalized amino acid constituents, then the secondary ligand candidates will contain azide-functionalized amino acid components. As with the previously described screens, the hit beads (23) are identified by their fluorescence and separated from the non-hit beads (15). While the hit beads can contain a certain amount of biligand capture agent that is formed by protein-catalyzed coupling of the bead-bound peptide with the peptide anchor ligand, the majority of the peptide on the hit beads (23) will likely be non-reacted secondary ligand. The protein and any non-reacted peptide anchor ligand are removed from the bead using standard chemical procedures, the peptide (24) on the bead is sequenced using standard methods, and a histogram (25) that correlates amino acid frequency versus amino acid identity is prepared. A second, more focused library (26) that uses those most commonly identified amino acids is then prepared, re-screened against the protein (11), and the hit beads are again identified by their peptide sequence (24). This second library of secondary ligands can contain slightly longer peptides, and the screening process can involve a lower concentration of the protein (11).

Determination of formation of a biligand or not from a secondary ligand screen can be performed according to several methods. A possible method is based on detection of information derived from the secondary ligand peptide sequences. Sequence homology, especially with respect to the identity and location of artificial amino acids within the peptide, can provide clues. Another possible method is based on bulk synthesis of secondary ligands, followed by an in situ click experiment together with the peptide anchor ligand and the protein. Furthermore, an additional screen, similar to that described in FIG. 19, but with the entire biligand synthesized on the beads, with perhaps some sequence variation, addition of controls, etc., can be done. Finally, the identified candidate biligand capture agents (27) can be synthesized in bulk quantities, and their measured binding affinity for the protein is compared against that of the peptide anchor ligand (19). An increased binding affinity of between 10 and 100 (i.e. increasing the affinity from $10^{-6}$M to $10^{-7}$M or $10^{-8}$M or less) or more can be obtained for the biligand capture agent versus the peptide anchor ligand.

If a desired affinity and/or selectivity is not achieved and/or if a longer capture agent is desired according to the experimental design, the biligand can itself be utilized as an anchor ligand, and the process described in FIG. 20 can be repeated as needed to prepare triligands.

Reference is made to FIG. 7 where a schematic illustration of the method to provide a triligand is shown. In a primary (1°) screen, a comprehensive OBOC library is incubated together with a labeled target. Hits are identified by either direct or indirect detection of the label, as detailed in Examples 3-5, 7, and 11. Hits from the 1° screen are modified with a first functional group, and then employed as an anchor ligand in a screen against the labeled target and a second OBOC library comprised of secondary (2°) ligands modified with a second functional group. Under certain conditions, the anchor ligand and secondary ligand simultaneously bind to the target and the functional groups covalently link to each other. The resulting capture agent is a biligand, as detailed in Example 7. In a tertiary (3°) screen, the process is repeated but now employing the biligand from the 2° screen (see FIG. 12) as the new anchor unit, allowing the rapid identification of a triligand capture agent (see also Example 11).

Additional ligands can be added by using the n-ligand obtained by covalently linking a selected primary ligand with the selected secondary ligand, and then using this construct as an anchor ligand for selection of further n-order ligands. An exemplary case is shown in Example 11, where a triligand capture agent composed of three ligands was identified. It is noted that this triligand can be further modified with one functional group and screened against an OBOC library comprised of quaternary (4°) ligands modified with a second functional group. The process of modifying the (n–1)-capture agent with one functional group and screening this construct against an OBOC library comprised of n-ligands modified with a second functional group can be repeated as many times until the desired physical, chemical, and/or biological properties are reached. For example, up to ten ligands and in particular up to seven ligands or two to five ligands can be added, but this is not meant to be limiting.

In several embodiments, as the number of ligands comprising the multi-ligand capture agent is increased, the affinity of that capture agent for the target molecule of interest will dramatically increase. In some of these embodiments, this effect is very large to the extent that two ligands that exhibit $10^{-6}$ M affinity for a protein can exhibit $10^{-12}$ M affinity if they are formed as a biligand. In particular, the affinity of the n-ligand can be as high as the product of the affinities of the individual ligand components. In several embodiments, increase of a product affinity by a $10^2$-$10^3$ per additional ligand is achieved (see Examples 10, 14, and 17).

In some embodiments, as the number of ligands comprising the multi-ligand capture agent increases, so does the selectivity of that capture agent for the protein of interest. A possible explanation that is not intended to be limiting and is provided herein for guidance purpose only, is that the ligands comprising the capture agent are sampling larger regions of the protein surface, and that protein surface is a unique fingerprint of the protein. As the number of ligands comprised in the multi-ligand capture agent increases, the number of contacts between such ligands and the target generally increase. These contacts can include van der Waals, hydrogen bonding, electrostatic, and hydrophobic interactions. An increased number of specific contacts generally promote an increased selectivity of the capture agent for the target.

In some embodiments, in which any of the ligand of the multiligand capture agent is linked to another so that so that it branches off of a non-terminal amino acid within the peptide secondary ligand, branched multi-ligand capture agents can be produced. Reference is made to FIG. 8 where a schematic illustration of the method to provide a branched triligand capture agent is shown. The method for selecting a branched biligand (via the 2° screen of FIG. 8) is nearly identical to FIG. 7. As shown in FIG. 8 the same anchor ligand identified by FIG. 7 and presenting a first functional group is used as the anchor ligand in a screen against the labeled target and a second OBOC library comprised of secondary (2°) ligands modified with a second functional group, but it is noted that the artificial amino acid presenting this second functional group is located at a non-terminal position of the library of secondary (2°) ligands. Under certain conditions, the anchor ligand and secondary ligand simultaneously bind to the target and the functional groups covalently link to each other.

Figure 16:
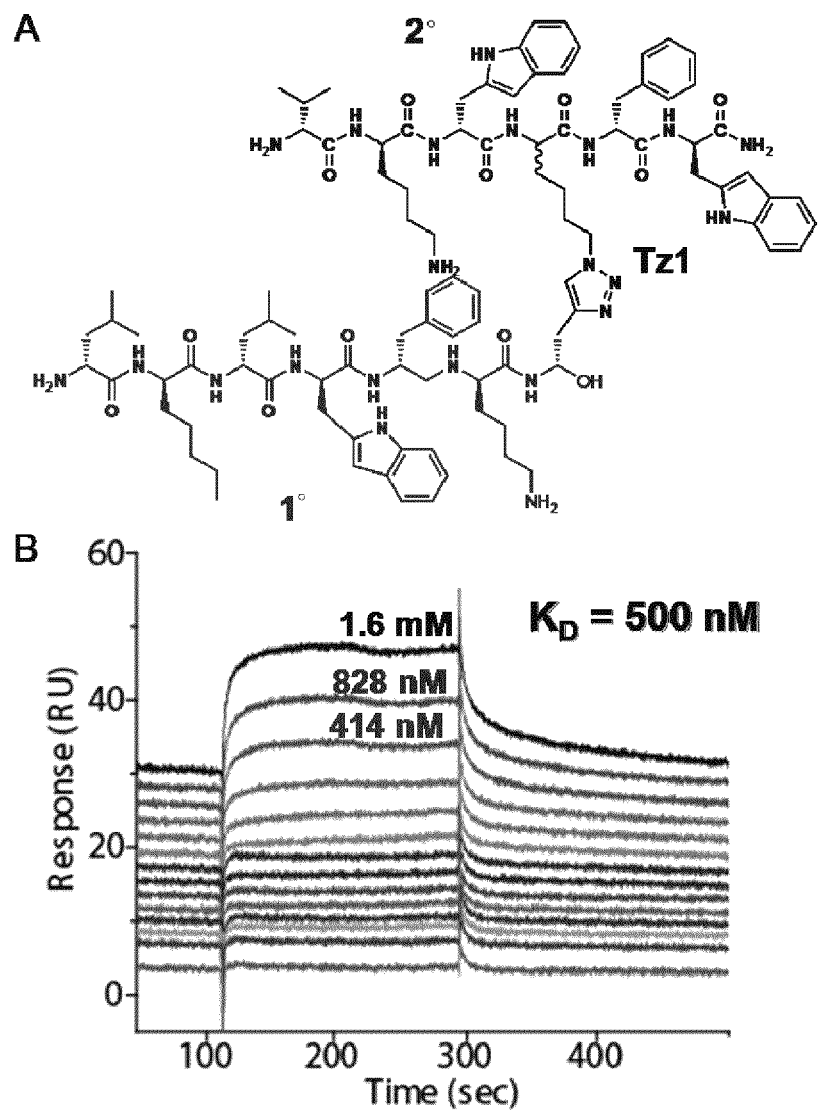
FIG. 16 shows structure and target affinity of a branched multi-ligand capture agent according to an embodiment herein described. Panel A shows the chemical structure of a branched biligand capture agent vkw(Tzl)fw-kfwlkl for b(h)CAII. Panel B shows that SPR response sensorgrams obtained with increasing concentration of the biligand (0 to 1656 nM) demonstrate a 500 nM binding affinity to the bCAII target. When compared to the binding affinity for the similarly developed linear biligand capture agent of FIG. 5, the affinity of this branched structure is improved by a factor of 5.

The resulting capture agent is a branched biligand, as detailed in Example 17 and FIG. 16A. In a tertiary (3°) screen, the process is repeated but now employing the branched biligand from the 2° screen as the new anchor unit, allowing the rapid identification of a triligand capture agent (see FIG. 18). In this 3° screen of FIG. 8 the OBOC library of tertiary (3°) ligands can present functional groups at a terminal position and result in a triligand capture agent with a single branchpoint (see FIG. 18), or at a non-terminal position and result in triligand capture agent with two branchpoints. This process can be repeated until a multi-ligand of n-ligands and n-branchpoints is obtained. This class of multi-ligand capture agents can emulate the effect of the variable region within a folded immunoglobulin (antibody), while maintaining a fairly low-molecular weight. FIG. 17B (one branchpoint) and FIG. 17C (two branchpoints) show representative structures of branched triligand capture agents. The branchpoints in branched multi-ligands can impart different conformational dynamics, as compared with the linear multi-ligand and within classes of branched capture agents. In some embodiments, the restricted rotations of bonds in the branched multi-ligand structures can increase avidity relative to a similarly developed but linear multi-ligand capture agent.

Alternate approaches to synthesizing and screening large libraries of peptides can be identified by a skilled person upon reading of the present disclosure. In particular, an additional approach other than the OBOC approach, can be provided by use of peptide microarrays (see R. C. Panicker et al. in *Combinatorial Chemistry & High Throughput Screening* (2004), Vol. 7, 547-556). In particular, in some embodiments, peptides can be attached on the glass substrate by noncovalent adsorption ("spotting") or covalent immobilization. In noncovalent adsorption methods, peptides are adhered to the surface by electrostatic interactions and are randomly oriented. In covalent immobilization methods, the peptide and substrate are joined by a chemical bond, and this attachment is typically achieved in a site-specific fashion (e.g., the Michael addition between a maleimide-functionalized substrate and a thiolated peptide). Peptide microarrays have the only intrinsic advantage of spatial encoding on the glass slides, and so an individual peptide or peptide composition is identified by its location. The peptide libraries can be made by conventional solid-phase peptide synthesis then affixed to the array (either noncovalently or covalently). In those embodiments, however, a library of peptides is made first (e.g. on beads) and the components are purified before making the array. Peptides also can be synthesized on the substrate itself by in situ methods (such as photolithography, see S. Li et al. in *Chem. Commun.* (2005), 581-583, and S. Li et al. in *J. Am. Chem. Soc.* (2004), Vol. 126, 4088-4089).

In some embodiments, the composition of the multi-ligand capture agents is such that the ability of binding the target is not affected by denaturation, since their affinity and selectivity are not contingent upon a folded structure. One exemplary case is the multi-ligand capture agent of FIG. 15 which is an unstructured linear capture agent comprised of three ligands, and was shown to be efficacious in dot blot (Example 16), native western blot (Example 20), and ELISA-like assays (Example 21). In particular, in several embodiments, multi-ligand capture agents are comprised of ligands of short lengths, and of non-natural and artificial monomers, which typically do not adopt a high degree of folded tertiary structure. Those embodiments differ from certain capture agents of the art such as antibodies, which are approximately 30 times longer in sequence, and are comprised of natural monomers, which promotes a high degree of folded tertiary structure (including disulfide linkages, which can potentially be unstable to denaturation).

In several embodiments, a desired property can be built into the capture agent, prior, during or following to the ligand selection process. Exemplary properties comprise water solubility, or the ability to attach the multi-ligand capture agent to a surface with a specific, desired orientation, and additional properties identifiable by a skilled person. In some embodiments a desired property can be introduced on the multi-ligand capture agent by introducing a related desired feature, such as functional group that can be exploited in a specific reaction associated with the desired property.

For example prior during or following the ligand selection of a multi-ligand capture agent, functional groups and other molecular tags can be built into the capture agent which enable specific, highly oriented attachment of the multi-ligand capture agent to a substrate or surface in a monoparameter or multiparameter assay. In particular, in some of those embodiments, a functional group can be introduced that can bind a second functional group presented on a substrate. Exemplary functional groups that can be used as binding partners include: carboxylic acid group and amine group, azide and acetylene, and aldehyde and amine. For example, aminated surfaces can be prepared by a treatment of glass or silicon with a silanizing agent, and this surface can be further covalently coupled to a capture agent presenting a carboxylic acid (McAlpine, M. C. et al., 2008). In a second example, acetylene (Rohde, R. D. et al., 2006) or azide (Cao, P. et al., 2008) modified silicon surfaces can be prepared and covalently coupled via the copper(I)-catalyzed azide-alkyne cycloaddition (CuAAC) to a capture agent modified with either an azide or acetylene, respectively. The modification of the multi-ligand capture agent to prepare it for orientation-specific immobilization on a surface can also include covalent tags such as short polynucleotide sequences, which allow the capture agent to be immobilized on a nucleic acid array by hybridization to its complementary strand (for example, by the methods of Fan, R. et al., 2008). In all of these examples, orientation-specific immobilization of the surface is readily achieved, which promotes uniformity between assays measuring specific binding of the target to the surface.

Once the two or more ligands are identified, the multi-ligand capture agent can be synthesized using methods identifiable by a skilled person, which depend on the chemical nature of the ligands. In particular, in embodiments wherein the two or more ligands are peptides, once the peptides are identified, a protein multi-ligand capture agent can be synthesized using methods to polymerize amino acid monomers identifiable by a skilled person.

Additional modifications of the synthesized multi-ligand capture agents can be performed. For example, in some embodiments, the multi-ligand capture agent can be modified to introduce a cell-penetrating peptide sequence, which specializes it as a capture agent for in vivo targeting or imaging. The multi-ligand capture agent can also be modified with a lipid molecule, which promotes association with a cellular membrane and then be used as a probe for cell-cell recognition.

In some embodiments multi-ligand capture agents can be provided by a method of making multi-ligand capture agents, the method comprising: contacting a modified anchor ligand with a first plurality of candidate ligands and a target, whereby the modified anchor ligand is covalently linked to one or more of the candidate ligands in a reaction catalyzed by the target, thereby forming one or more multi-ligand capture agents. Each of the multi-ligand capture agents comprises the modified anchor ligand and one of the candidate ligands, the anchor ligand can bind the target, and the modified anchor ligand comprises a first functional group, wherein the first functional group is capable of specifically reacting with a corresponding second functional group, and wherein each of the candidate ligands comprises the second functional group.

The method can further comprise, (i) modifying one of the multi-ligand capture agents to comprise a third functional group, wherein the third functional group is capable of specifically reacting with a corresponding fourth functional group, and (ii) contacting the modified multi-ligand capture agent with a second plurality of candidate ligands and a target, whereby the modified multi-ligand capture agent is covalently linked to one or more of the candidate ligands in a reaction catalyzed by the target, thereby forming one or more higher order multi-ligand capture agents. Each of the higher order multi-ligand capture agents can comprise the modified multi-ligand capture agent and one of the candidate ligands, and each of the candidate ligands in the second plurality of capture ligands can comprise the fourth functional group.

The method can further comprise repeating steps (i) and (ii) one or more times, wherein for each repetition of steps (i) and (ii) one of the higher order multi-ligand capture agents formed in the last iteration of step (ii) is used as the multi-ligand capture agent modified in the next iteration of step (i). Steps (i) and (ii) can be repeated two or more times, three or more times, four or more times, five or more times, six or more times, or seven or more times. Steps (i) and (ii) can be repeated until the binding affinity to the target of the higher order multi-ligand capture agent is at least $10^7$, at least $10^8$, at least $10^9$, at least $10^{10}$, at least $10^{11}$, at least $10^{12}$, or at least $10^{13}$ higher that the binding affinity of the anchor ligand. Steps (i) and (ii) can be repeated until the binding affinity to the target of the multi-ligand capture agent is such that the dissociation constant for binding of the multiligand to the target equal to or less than $10^{-6}$ M, $10^{-7}$ M, $10^{-8}$ M, $10^{-9}$ M, $10^{-10}$ M, $10^{-11}$ M, $10^{-12}$ M, $10^{-13}$ M, $10^{-14}$ M, $10^{-15}$ M, or $10^{-16}$ M.

The second plurality of candidate ligands can be the same as the first plurality of candidate ligands. The second plurality of candidate ligands can be different from the first plurality of candidate ligands. Some of the candidate ligands in the second plurality of candidate ligands can be the same as some of the candidate ligands in the first plurality of candidate ligands. Some of the candidate ligands in the second plurality of candidate ligands can be different from some of the candidate ligands in the first plurality of candidate ligands. Some of the candidate ligands in the second plurality of candidate ligands can be the same as some of the candidate ligands in the first plurality of candidate ligands, and some of the candidate ligands in the second plurality of candidate ligands can be different from some of the candidate ligands in the first plurality of candidate ligands.

A different plurality of candidate ligands can be used as the second plurality of candidate ligands in one or more of the iterations of steps (i) and (ii). A different plurality of candidate ligands can be used as the second plurality of candidate ligands in all of the iterations of steps (i) and (ii). The same plurality of candidate ligands can be used as the second plurality of candidate ligands in one or more of the iterations of steps (i) and (ii). The same plurality of candidate ligands can be used as the second plurality of candidate ligands in all of the iterations of steps (i) and (ii). A plurality of different pluralities of candidate ligands can be used as the second plurality of candidate ligands in the iterations of steps (i) and (ii).

The third functional group can be the same as the first functional group. The fourth functional group can be the same as the second functional group. The third functional group can be the same as the second functional group. The fourth functional group can be the same as the first functional group. The third functional group can be different from the first functional group. The third functional group can be different from the second functional group. The fourth functional group can be different from the first functional group. The fourth functional group can be different from the second functional group.

In some forms of the methods, for each repetition of steps (i) and (ii) the same third functional group can be used. In some forms of the methods, for each repetition of steps (i) and (ii) the same fourth functional group can be used. In some forms of the methods, for each repetition of steps (i) and (ii) a different third functional group can be used. In some forms of the methods, for some repetitions of steps (i) and (ii) a different fourth functional group can be used. In some forms of the methods, for some repetitions of steps (i) and (ii) the same third functional group can be used. In some forms of the methods, for some repetitions of steps (i) and (ii) the same fourth functional group can be used. In some forms of the methods, for some repetitions of steps (i) and (ii) a different fourth functional group can be used.

The method can further comprise, prior to the step of contacting the modified anchor ligand with the first plurality of candidate ligands and the target, contacting the target with a third plurality of candidate ligands and identifying candidate ligands that bind to the target, wherein one of the identified candidate ligands is used as the anchor ligand.

The method can further comprise, prior to the step of contacting the modified anchor ligand with the first plurality of candidate ligands and the target, preparing the modified anchor ligand.

The modified anchor ligand can be prepared by synthesizing a form of the anchor ligand comprising the first functional group. The modified anchor ligand can be prepared by completing synthesis of a partially synthesized anchor ligand, wherein the first functional group is added to the anchor ligand during completion of the synthesis. The modified anchor ligand can be prepared by adding the first functional group to the anchor ligand. The higher order multi-ligand capture agent can be the multi-ligand capture agent made by the method. The higher order multi-ligand capture agents formed in the last iteration of step (ii) can be the multi-ligand capture agent made by the method. The modified anchor ligand can be covalently linked to one or more of the candidate ligands via a reaction between the first functional group and the second functional group. The multi-ligand capture agents can bind the target.

In some forms of the methods, it is not known prior to contacting which of the candidate ligands can bind to the target.

The plurality of candidate ligands can comprise a combinatorial library of compounds. The combinatorial library of compounds can comprise compounds comprising permutations of a group of subunits linked in chains. The chains can be straight, branched, circular, or a combination. The group of subunits can comprise amino acids, modified amino acids, or a combination. The group of subunits can further comprise one or more small organic molecules. The amino acids in the group of subunits can consist essentially of a subset of amino acids. The modified amino acids in the group of subunits can consist essentially of a subset of modified amino acids. The group of subunits can consist essentially of amino acids. The group of subunits can consist essentially of a subset of amino acids.

The binding specificity of the multi-ligand capture agent relative to a reference molecule can be at least 5, at least 10, at least 20, or at least 100. The binding of the multi-ligand capture agent to a reference molecule can be undetectable in a reference assay. The reference molecule can be a molecule related to the target. The reference molecule can be the target. The reference target can be an allelic version of the target. The reference target can be a homolog of the target. The reference molecule can be a reference sample. The reference sample can be a sample lacking the target that is of the same type as a sample in which the target is to be detected. The reference sample can be a sample lacking the target that is of the same source as a sample in which the target is to be detected.

The binding affinity to the target of the multi-ligand capture agent can be at least $10^6$, at least $10^7$, at least $10^8$, at least $10^9$, at least $10^{10}$, at least $10^{11}$, at least $10^{12}$, or at least $10^{13}$ higher that the binding affinity of the anchor ligand. The dissociation constant for binding of the multi-ligand capture agent to the target can be equal to or less than $10^{-6}$ M, $10^{-7}$ M, $10^{-8}$ M, $10^{-9}$ M, $10^{-10}$ M, $10^{-11}$ M, $10^{-12}$ M, $10^{-13}$ M, $10^{-14}$ M, $10^{-15}$ M, or $10^{-16}$ M.

In some forms, the modified anchor ligand is not a natural substrate of the target. In some forms, the modified anchor ligand is not a substrate of the target. In some forms, the first plurality of candidate ligands does not comprise natural substrates of the target. In some forms, the first plurality of candidate ligands does not comprise substrates of the target. In some forms, the first plurality of candidate ligands does not comprise compounds modeled on a compound known to bind the target. In some forms, the first plurality of candidate ligands does not comprise compounds derived from a compound known to bind the target. In some forms, the first plurality of candidate ligands does not comprise any compound known to bind the target. In some forms, the first plurality of candidate ligands does not comprise any compound identified as binding to the target. In some forms, the first plurality of candidate ligands does not comprise compounds modeled on a compound known to bind the target prior to the step of contacting the modified anchor ligand, the first plurality of candidate ligands, and the target. In some forms, the first plurality of candidate ligands does not comprise compounds derived from a compound known to bind the target prior to the step of contacting the modified anchor ligand, the first plurality of candidate ligands, and the target. In some forms, the first plurality of candidate ligands does not comprise any compound known to bind the target prior to the step of contacting the modified anchor ligand, the first plurality of candidate ligands, and the target. In some forms, the first plurality of candidate ligands does not comprise any compound identified as binding to the target prior to the step of contacting the modified anchor ligand, the first plurality of candidate ligands, and the target.

Also described are multi-ligand capture agents made by any of the disclosed methods. Also described are multi-ligand capture agents that comprise a modified form of a multi-ligand capture agent made by any of the disclosed methods. One or more functional group portions of the multi-ligand capture agent can be modified. The functional group portion of the multi-ligand capture agent can be modified by replacing the functional group portion with a linker. The functional group portion of the multi-ligand capture agent can be modified by replacing the functional group portion with a subunit. The subunit can comprise an amino acid or a modified amino acid. The subunit can comprise a small organic molecule. The multi-ligand capture agent can comprise two or more subunits linked in chains, wherein one or more of the subunits is modified. The subunit can be modified by replacing the subunit with a different subunit. The subunit can comprise an amino acid or a modified amino acid. The subunit can comprise a small organic molecule.

Also disclosed are multi-ligand capture agents comprising a first ligand and a second ligand, wherein the first ligand and second ligand are covalently linked, wherein in isolation the first ligand can bind a target, wherein in isolation the second ligand can bind the target, wherein the first ligand and the second ligand are bindingly distinguishable in their binding to the target, wherein the multi-ligand capture agent can specifically bind the target, wherein both the first ligand and the second ligand contact the target when the multi-ligand capture agent binds the target. In some forms, the first ligand and the second ligand are not covalently linked in nature. In some forms, the first ligand and the second ligand are not portions of the same natural molecule. In some forms, the first ligand and the second ligand are not portions of the same substrate of the target. In some forms, the first ligand is not modeled on a compound known to bind the target. In some forms, the first ligand is not derived from a compound known to bind the target. In some forms, the second ligand is not modeled on a compound known to bind the target. In some forms, the second ligand is not derived from a compound known to bind the target.

In some forms, the second ligand can be identified by contacting a modified anchor ligand with a plurality of candidate ligands and the target, whereby the modified anchor ligand was covalently linked to one of the candidate ligands in a reaction catalyzed by the target, wherein the second ligand is the candidate ligand that was covalently linked to the modified anchor ligand, wherein the modified anchor ligand comprised a first functional group, wherein the first functional group is capable of specifically reacting with a corresponding second functional group, wherein each of the candidate ligands comprised the second functional group. The anchor ligand can have comprised the first ligand.

The multi-ligand capture agent can comprise a third ligand, wherein the third ligand is covalently linked to the first and second ligands, wherein the third ligand contacts the target when the multi-ligand capture agent binds the target. In some forms, in isolation the third ligand can bind the target. The first ligand and the third ligand can be bindingly distinguishable in their binding to the target. The second ligand and the third ligand can be bindingly distinguishable in their binding to the target. The third ligand can be directly linked to the first ligand. The third ligand can be directly linked to the second ligand. The third ligand can be linked to the second ligand via the first ligand. The third ligand can be linked to the first ligand via the second ligand. In some forms, the first ligand and the third ligand are not covalently linked in nature. In some forms, the first ligand and the third ligand are not portions of the same natural molecule. In some forms, the first ligand and the third ligand are not portions of the same substrate of the target. In some forms, the second ligand and the third ligand are not covalently linked in nature. In some forms, the second ligand and the third ligand are not portions of the same natural molecule. In some forms, the second ligand and the third ligand are not portions of the same substrate of the target. In some forms, the third ligand is not modeled on a compound known to bind the target. In some forms, the third ligand is not derived from a compound known to bind the target.

The third ligand can be identified by contacting a modified anchor ligand with a plurality of candidate ligands and the target, whereby the modified anchor ligand was covalently linked to one of the candidate ligands in a reaction catalyzed by the target, wherein the third ligand is the candidate ligand that was covalently linked to the modified anchor ligand, wherein the modified anchor ligand comprised a first functional group, wherein the first functional group is capable of specifically reacting with a corresponding second functional group, wherein each of the candidate ligands comprised the second functional group. The anchor ligand can have comprised the first ligand. The anchor ligand can have comprised the second ligand.

The multi-ligand capture agent can comprise a fourth ligand, wherein the fourth ligand is covalently linked to the first, second, and third ligands, wherein the fourth ligand contacts the target when the multi-ligand capture agent binds the target. In some forms, in isolation the fourth ligand can bind the target. The first ligand and the fourth ligand can be bindingly distinguishable in their binding to the target. The second ligand and the fourth ligand can be bindingly distinguishable in their binding to the target. The third ligand and the fourth ligand can be bindingly distinguishable in their binding to the target. The fourth ligand can be directly linked to the first ligand. The fourth ligand can be directly linked to the second ligand. The fourth ligand can be directly linked to the third ligand. The fourth ligand can be linked to the second ligand via the first ligand. The fourth ligand can be linked to the second ligand via the third ligand. The fourth ligand can be linked to the first ligand via the second ligand. The fourth ligand can be linked to the first ligand via the third ligand. The fourth ligand can be linked to the third ligand via the first ligand. The fourth ligand can be linked to the third ligand via the second ligand. In some forms, the first ligand and the fourth ligand are not covalently linked in nature. In some forms, the first ligand and the fourth ligand are not portions of the same natural molecule. In some forms, the first ligand and the fourth ligand are not portions of the same substrate of the target. In some forms, the second ligand and the fourth ligand are not covalently linked in nature. In some forms, the second ligand and the fourth ligand are not portions of the same natural molecule. In some forms, the second ligand and the fourth ligand are not portions of the same substrate of the target. In some forms, the third ligand and the fourth ligand are not covalently linked in nature. In some forms, the third ligand and the fourth ligand are not portions of the same natural molecule. In some forms, the third ligand and the fourth ligand are not portions of the same substrate of the target. In some forms, the fourth ligand is not modeled on a compound known to bind the target. In some forms, the fourth ligand is not derived from a compound known to bind the target.

The fourth ligand can be identified by contacting a modified anchor ligand with a plurality of candidate ligands and the target, whereby the modified anchor ligand was covalently linked to one of the candidate ligands in a reaction catalyzed by the target, wherein the fourth ligand is the candidate ligand that was covalently linked to the modified anchor ligand, wherein the modified anchor ligand comprised a first functional group, wherein the first functional group is capable of specifically reacting with a corresponding second functional group, wherein each of the candidate ligands comprised the second functional group. The anchor ligand can have comprised the first ligand. The anchor ligand can have comprised the second ligand. The anchor ligand can have comprised the third ligand.

In some embodiments, the multi-ligand capture agents herein described are comprised in a composition together with a suitable vehicle. The term "vehicle" as used herein indicates any of various media acting usually as solvents, carriers, binders or diluents for the multi-ligand capture agents that are comprised in the composition as an active ingredient. In particular, the composition including the multi-ligand capture agent can be used in one of the methods or systems herein described.

Multi-ligand capture agents herein described can be used in methods and systems for detecting and/or separating one or more targets in a sample.

The terms "detect" or "detection" as used herein indicates the determination of the existence, presence or fact of a target in a limited portion of space, including but not limited to a sample, a reaction mixture, a molecular complex and a substrate. The "detect" or "detection" as used herein can comprise determination of chemical and/or biological properties of the target, including but not limited to ability to interact, and in particular bind, other compounds, ability to activate another compound and additional properties identifiable by a skilled person upon reading of the present disclosure. The detection can be quantitative or qualitative. A detection is "quantitative" when it refers, relates to, or involves the measurement of quantity or amount of the target or signal (also referred as quantitation), which includes but is not limited to any analysis designed to determine the amounts or proportions of the target or signal. A detection is "qualitative" when it refers, relates to, or involves identification of a quality or kind of the target or signal in terms of relative abundance to another target or signal, which is not quantified.

The term "separate" as used herein indicates setting, keeping apart or making a distinction between an item and another, and in particular between a target and another analyte which is not of interest, and includes sorting a plurality of targets of interest. The term "sort" as used herein indicates to set a group set up on the basis of any characteristic in common. In particular; the multi-ligand capture agent herein described can be used to separate a target and/or sorting a plurality of targets in a sample.

The term "sample" as used herein indicates a limited quantity of something that is indicative of a larger quantity of that something, including but not limited to fluids from a biological environment, specimen, cultures, tissues, commercial recombinant proteins, synthetic compounds or portions thereof.

In particular, the multi-ligand capture agents herein described can be used in methods and systems for performing assays for the detection of targets, including monoparameter assays, and multiparameter assays, all of which can be performed as multiplex assays.

The term "monoparameter assay" as used herein refers to an analysis performed to determine the presence, absence, or quantity of one target. The term "multiparameter assay" refers to an analysis performed to determine the presence, absence, or quantity of a plurality of targets. The term "multiplex" or "multiplexed" assays refers to an assay in which multiple assays reactions, e.g., simultaneous assays of multiple analytes, are carried out in a single reaction chamber and/or analyzed in a single separation and detection format.

Monoparameter assays that can be performed with the multi-ligand capture agents herein described, include but are not limited to, any assays for the detection of single markers in serum, single protein detection in biological samples, cell sorting according to one surface marker and further assays that can be performed with a capture agent, which are identifiable by a skilled person upon reading of the present disclosure. Many analytes and targets useful for detection are known to those of skill in the art and can be detected and/or captured using the disclosed multi-ligand capture agents and methods. Many assays and detection methods, including many different assay formats are known to those of skill in the art and can be adapted to use the disclosed multi-ligand capture agents. In particular, any assay or detection method that makes use of an antibody can be adapted to use one or more of the disclosed multi-ligand capture agents in addition to or as a substitute for any antibody used in the assay or method.

Multiparameter assays that can be performed with the multi-ligand capture agents herein described, include but are not limited to any proteomic analysis, tissue analysis, serum diagnostics, biomarker, serum profiling, multiparameter cell sorting, single cell studies, and additional assays identifiable by a person skilled in the art upon reading of the present disclosure.

In some embodiments, the multi-ligand capture agents herein described can advantageously be used to perform diagnostic assays, wherein the target(s) to be detected are predetermined biomarkers associated to a predetermined condition. The wording "associated to" as used herein with reference to two items indicates a relation between the two items such that the occurrence of a first item is accompanied by the occurrence of the second item, which includes but is not limited to a cause-effect relation and sign/symptoms-disease relation. Exemplary biomarkers include clinically informative biomarkers, and diagnostic biomarkers.

Those embodiments are particularly advantageous in a diagnostic approach where different classes of biomaterials and biomolecules are each measured from a different region of a typically heterogeneous tissue sample, thus introducing unavoidable sources of noise that are hard to quantitate.

Figure 21:
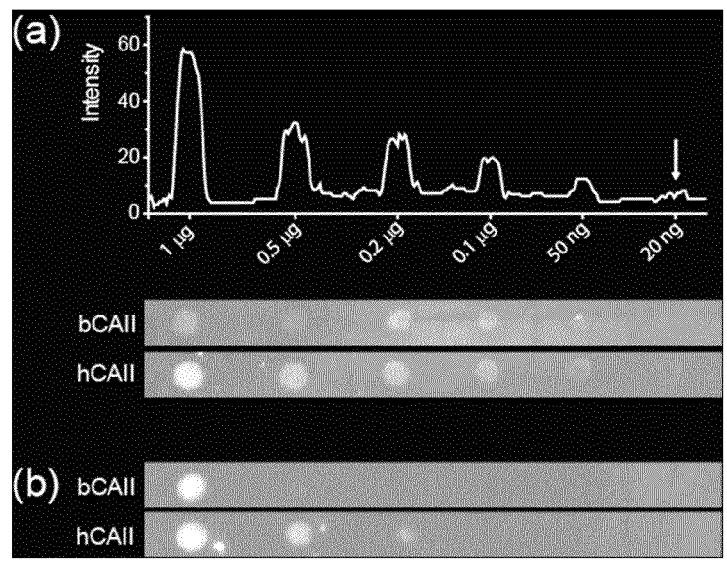
FIG. 21 schematically shows the sensitivity of target detection performed with the biligand of FIG. 14 and the triligand of FIG. 15 according to an embodiment herein described. Panel A shows a dot blot performed with the triligand of FIG. 15 for detection of b(h)CAII in 10% porcine serum (lower part) and a related diagram (upper part). Panel B shows dot blot performed with the biligand of FIG. 14 in 0.1% porcine serum.
Figure 22:
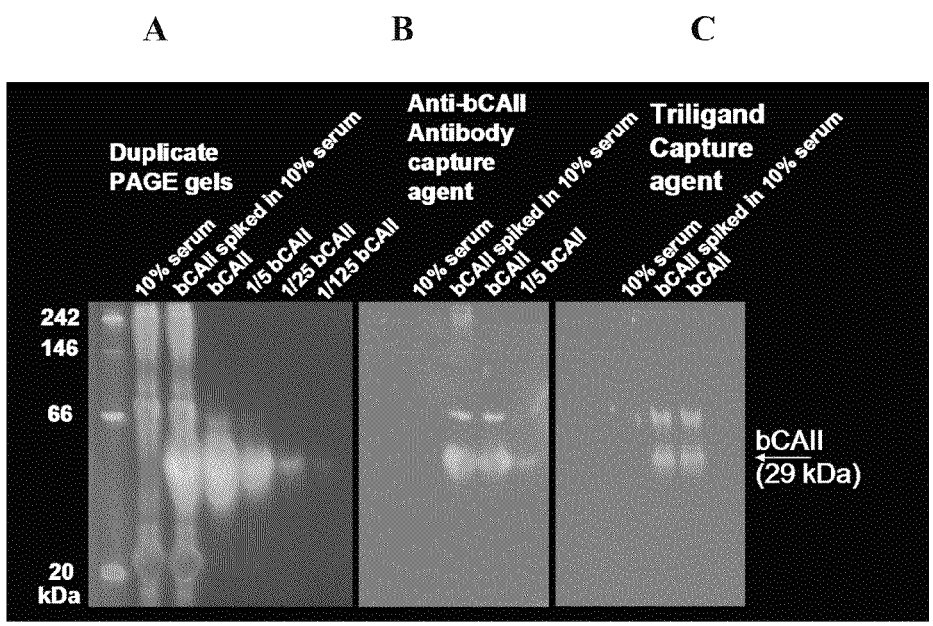
FIG. 22 shows the results of a native western blot performed with multi-ligand capture agents according to some embodiments herein described. Panel A shows Coomassie-stained native gel, detailing the total protein content. Panel B shows a native western blot, illustrating specific protein binding by a primary antibody. Panel C shows a native western blot, illustrating specific protein binding by a triligand capture agent.
Figure 23:
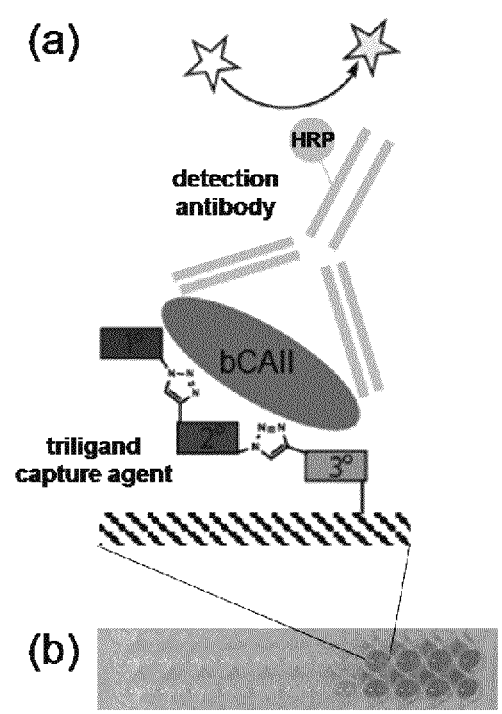
FIG. 23 shows a schematic illustration of a detection of a target molecule performed with a multi-ligand capture agent according to an embodiment herein described. Panel A shows a schematic illustration of the structure of fully assembled ELISA-like sandwich absorbance assays using the triligand capture agent to detect bCAII protein. Panel B shows experimental data of ELISA assays at varying concentrations of bCAII as performed in the wells of a 96-well plate. Increasing bCAII concentration is detected as an increasing grey color. Panels C and D show diagrams illustrating various assay conditions. The target is presented in buffered solution in Panel C, while in Panel D, the target is presented in 10% porcine serum with no compromise in specific binding by either the triligand capture agent or detection antibody.

Exemplary assays that can be performed with the multi-ligand capture agents herein described include but are not limited to serum diagnostics, immunohistochemistry, cell sorting, single cell studies, dot blots, western blots, affinity purification and other separations, and enzyme-linked immunosorbent assays as illustrated in FIG. 21, FIG. 22, and FIG. 23 of Examples 16, 20, and 21.

In additional embodiments, the multi-ligand capture agents herein described can be used to perform microfluidic based assays. The term "microfluidic" as used herein refers to a component or system that has microfluidic features e.g. channels and/or chambers that are generally fabricated on the micron or sub-micron scale. For example, the typical channels or chambers have at least one cross-sectional dimension in the range of about 0.1 microns to about 1500 microns, more typically in the range of about 0.2 microns to about 1000 microns, still more typically in the range of about 0.4 microns to about 500 microns. Individual microfluidic features typically hold very small quantities of fluid, e.g. from about 10 nanoliters to about 5 milliliters, more typically from about 100 nanoliters to about 2 milliliters, still more typically from about 200 nanoliters to about 500 microliters, or yet more typically from about 500 nanoliters to about 200 microliters.

The methods and systems herein described allow the multiplexed multiparameter detection, sorting and of biomarkers of interest and related diagnostic analysis.

As disclosed herein, the multi-ligand capture agents herein described can be provided as a part of systems to perform any assay, including any of the assays described herein. The systems can be provided in the form of arrays or kits of parts. An array, sometimes referred to as a "microarray", can include any one, two or three dimensional arrangement of addressable regions bearing a particular molecule associated to that region. Usually, the characteristic feature size is micrometers.

In a kit of parts, the multi-ligand capture agent and other reagents to perform the assay can be comprised in the kit independently. The multi-ligand capture agent can be included in one or more compositions, and each capture agent can be in a composition together with a suitable vehicle.

Additional components can include labeled molecules and in particular, labeled polynucleotides, labeled antibodies, labels, microfluidic chip, reference standards, and additional components identifiable by a skilled person upon reading of the present disclosure. The terms "label" and "labeled molecule" as used herein as a component of a complex or molecule referring to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence, the wording "labeling signal" as used herein indicates the signal emitted from the label that allows detection of the label, including but not limited to radioactivity, fluorescence, chemiluminescence, production of a compound in outcome of an enzymatic reaction and the like.

In some embodiments, detection of a multi-ligand capture agent can be carried either via fluorescent based readouts, in which the labeled antibody is labeled with fluorophore, which includes, but not exhaustively, small molecular dyes, protein chromophores, quantum dots, and gold nanoparticles. Additional techniques are identifiable by a skilled person upon reading of the present disclosure and will not be further discussed in detail.

In particular, the components of the kit can be provided, with suitable instructions and other necessary reagents, in order to perform the methods here described. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (i.e. wash buffers and the like).

In some embodiments, the multi-ligand capture agents herein described can be included in pharmaceutical compositions together with an excipient or diluent. In particular, in some embodiments, disclosed are pharmaceutical compositions which contain at least one multi-ligand capture agent as herein described, in combination with one or more compatible and pharmaceutically acceptable vehicles, and in particular with pharmaceutically acceptable diluents or excipients. In those pharmaceutical compositions the multi-ligand capture agent can be administered as an active ingredient for treatment or prevention of a condition in an individual.

The term "treatment" as used herein indicates any activity that is part of a medical care for, or deals with, a condition, medically or surgically.

The term "prevention" as used herein indicates any activity which reduces the burden of mortality or morbidity from a condition in an individual. This takes place at primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

The term "condition" as used herein indicates a physical status of the body of an individual (as a whole or as one or more of its parts), that does not conform to a standard physical status associated with a state of complete physical, mental and social well-being for the individual. Conditions herein described include but are not limited disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms.

The term "individual" as used herein in the context of treatment includes a single biological organism, including but not limited to, animals and in particular higher animals and in particular vertebrates such as mammals and in particular human beings.

The term "excipient" as used herein indicates an inactive substance used as a carrier for the active ingredients of a medication. Suitable excipients for the pharmaceutical compositions herein described include any substance that enhances the ability of the body of an individual to absorb the multi-ligand capture agents or combinations thereof. Suitable excipients also include any substance that can be used to bulk up formulations with the peptides or combinations thereof, to allow for convenient and accurate dosage. In addition to their use in the single-dosage quantity, excipients can be used in the manufacturing process to aid in the handling of the peptides or combinations thereof concerned. Depending on the route of administration, and form of medication, different excipients can be used. Exemplary excipients include, but are not limited to, antiadherents, binders, coatings, disintegrants, fillers, flavors (such as sweeteners) and colors, glidants, lubricants, preservatives, sorbents.

The term "diluent" as used herein indicates a diluting agent which is issued to dilute or carry an active ingredient of a composition. Suitable diluents include any substance that can decrease the viscosity of a medicinal preparation.

Further advantages and characteristics of the present disclosure will become more apparent hereinafter from the following detailed disclosure by way or illustration only with reference to an experimental section.

EXAMPLES

The capture agents, methods and system herein described are further illustrated in the following examples, which are provided by way of illustration and are not intended to be limiting. In particular, in the following examples a further a description of the multi-ligand capture agents and related methods and systems of the present disclosure is provided with reference multi-ligand capture agents of a protein nature where the ligands are of formed by polypeptides. A person skilled in the art will appreciate the applicability of the features described in detail for capture agents formed by ligands of amino acid chemical nature to capture agents formed in all or in part by ligands of another chemical nature. In particular, a skilled person reading the present disclosure will appreciate that multi-ligand capture agents of a peptidic chemical nature, are only one exemplary of capture agents and that multi-ligand capture agents can include oligo- and polynucleotides, small molecules, and other biologically active ligands.

In particular, a method for developing multi-ligand capture agents, including multi-ligand capture protein agents and multi-ligand capture agents of a protein nature, that can replace the current standard, antibodies, is described and demonstrated with reference to exemplary embodiments where the ligands are provided by peptide-like molecules. In particular, each ligand is a peptide-like molecule, comprised of natural, artificial, or non-natural amino acids and other organic molecule building blocks. Each multi-ligand is comprised of two or more ligands, and each ligand is comprised of a multiple of building blocks (amino acids, etc.). As the number of ligands comprising the multi-ligand is increased, the selectivity and affinity of the multi-ligand for the protein of interest rapidly increases. The target protein itself is utilized as a catalyst to assemble its own multi-ligand capture agent. The individual ligands themselves (and their constituent amino acids) are specifically designed for this catalytic process. Chemical and biochemical stability, water solubility, thermal stability, and other desired characteristics can be designed into the multi-ligand. Furthermore, the multi-ligand can be produced in gram-scale quantities using conventional chemical methods.

In the following examples uses of protein-catalyzed, multi-ligand capture agents in standard protein assays are also exemplified. There are a number of standard protein assays that are used in either laboratory or clinical settings. The standard assays fall into two classes: assays performed by direct labeling of the sample analyte, and label-free assays. For these standard assays, the most common protein capture agents are antibodies.

Label-free assays are those in which at least one antibody is utilized to detect its cognate protein. These include assays such as western blots and dot blots, and sandwich assays such as the enzyme-linked immunosorbent assay (ELISA).

Example 1

Synthesis and Characterization of Functionalized Artificial Amino Acids

For azide-containing artificial amino acid synthesis, all chemicals were purchased from Sigma-Aldrich (St. Louis, Mo.) and used as received. Fmoc-D-propargylglycine (Fmoc-D-Pra-OH) was acquired from a commercial vendor (Chem-Impex International, Wood Dale, Ill.) and used as the acetylene handle for construction of anchor ligands and biligands.

Scheme 1 describes the synthesis of the azide-containing artificial amino acids Fmoc-Az4-OH and Fmoc-Az8-OH which were incorporated in one-bead one-compound peptide libraries. Detailed synthetic protocol and spectroscopic characterization is provided for Fmoc-Az4-OH. For Fmoc-Az8-OH, only spectroscopic characterization is provided.

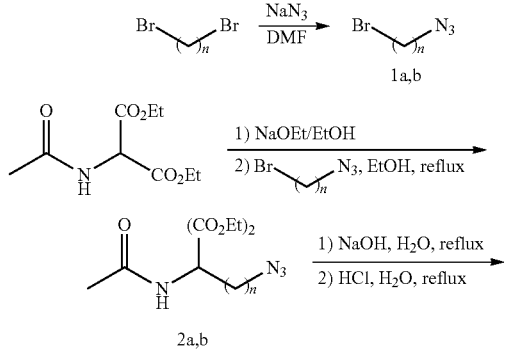

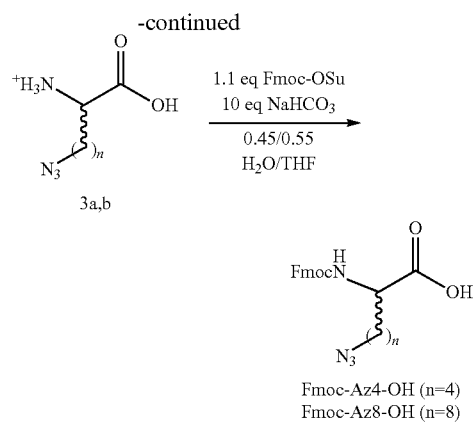

Fmoc-Az4-OH (n=4)
Fmoc-Az8-OH (n=8)

a: n = 4
b: n = 8

Azidobutylbromide (1a). To a solution of 1,4-dibromobutane (123 mmol), sodium azide (61.5 mmol) was added and stirred overnight in N,N'-dimethylformamide (DMF) at 50° C. The reaction was diluted with ethyl acetate, and the organic layer was washed with water, then brine, and then dried over MgSO$_4$. The crude residue was purified by silica gel chromatography (100% hexanes) to give a product (80%) as clear oil. $^1$H NMR (300 MHz, CDCl$_3$): δ 3.44 (2H, t, J=6.3 Hz), 3.34 (2H, t, J=6.6 Hz), 1.93-1.98 (2H, m), 1.74-1.79 (2H, m).

Azidooctylbromide (1b). Synthesis was carried out as described above, except 1,8-dibromobutane was used as the starting material. $^1$H NMR (300 MHz, CDCl$_3$): δ 3.41 (2H, t, J=6.9 Hz), 3.26 (2H, t, J=6.6 Hz), 1.86 (2H, p, J=6.9 Hz), 1.60 (2H, p, J=8.7 Hz), 1.34-1.55 (4H, m).

Diethyl 2-acetamido-2-(4-azidobutyl)malonate (2a). To a solution of 0.598 g (0.026 mol) sodium metal in 25 ml absolute EtOH, 5.65 g diethyl acetamidomalonate (0.026 mol) was added, following previously published procedures (Chenault, H. K. et al., 1989). The mixture was stirred for 30 min at room temperature. By dropwise addition, azidobutylbromide 1a (4.82 g, 0.027 mol) was added with stirring. The reaction mixture was stirred for 2 h at room temperature and refluxed for 6 h at 80° C. After cooling overnight, the reaction mixture was concentrated to dryness, and the residue was extracted with diethyl ether. The combined ether extracts were washed with water, sat. NaHCO$_3$, water, and brine, and were dried over MgSO$_4$ and then concentrated. Silica gel chromatography (Hex:EtOAc=1:1) gave a product (63%) as a clear, viscous oil. $^1$H NMR (300 MHz, CDCl$_3$): δ 6.77 (1H, s), 4.24 (4H, q, J=6.9 Hz), 3.26 (2H, t, J=6.9 Hz), 2.31-2.37 (2H, m), 2.04 (3H, s), 1.59 (2H, p, J=7.5 Hz), 1.26 (6H, t, J=6 Hz), 1.16-1.27 (2H, m). ESI-MS m/e 315.

Diethyl 2-acetamido-2-(4-azidooctyl)malonate (2b). Similar synthetic protocol as 2a was adopted, only azidooctylbromide 1b served as the starting material. $^1$H NMR (300 MHz, CDCl$_3$): δ 6.76 (1H, s), 4.24 (4H, q, J=7.2 Hz), 3.24 (2H, t, J=6.9 Hz), 2.27-2.33 (2H, m), 2.04 (3H, s), 1.56 (2H, p, J=7.5 Hz), 1.25 (6H, t, J=7.2 Hz), 1.06-1.16, 1.2-1.4 (10H, m). ESI-MS m/e 371.

2-Azidobutyl amino acid (3a). Following standard methods, the diester 2a (2.8 mmol) in 25 ml of 10% NaOH solution was heated to reflux for 4 h (van Hest, J. C. M. et al., 2000). The solution was then neutralized with concentrated HCl and evaporated. The residue was dissolved in 25 ml of 1 M HCl and heated to reflux for 3 h. The solvent was reduced and extraction with MeOH afforded amino acid 3a as the hydrochloride salt (85%). $^1$H NMR (300 MHz, CD$_3$OD): δ 3.98 (1H, t, J=6.3 Hz), 3.35 (2H, t, J=7.8 Hz), 1.45-1.7, 1.85-2.05 (6H, m). MALDI-MS m/e 173.

2-Azidooctyl amino acid (3b). Synthesis was carried out as described above, using diester 2b as the starting material. $^1$H NMR (300 MHz, CD$_3$OD): δ 3.94 (1H, t, J=6.3 Hz), 3.27 (2H, t, J=6.9 Hz), 1.3-1.52, 1.52-1.62, 1.8-1.98 (14H, m). ESI-MS m/e 229.

Fmoc-2-Azidobutyl amino acid (Fmoc-Az4-OH). The amino acid 3a (26.3 mmol) was dissolved in 0.45:0.55 H$_2$O:THF (150 ml), and NaHCO$_3$ (22.1 g, 263 mmol) was added, following published methods (Lee, H.-S. et al., 2003). After the mixture was cooled to 0° C., Fmoc-OSu (9.7 g, 28.9 mmol) was added dropwise over 5 min. The reaction mixture was allowed to come to room temperature and stirred overnight. Evaporation of THF was completed in vacuo and the aqueous residue was washed with diethyl ether (2×200 ml). The aqueous layer was then collected and acidified with conc. HCl to pH 2 before extraction with ethyl acetate (4×100 ml). The combined organic layers were washed with brine, dried over MgSO$_4$, filtered, and concentrated. The organic residue was purified by column chromatography (2% MeOH in DCM) to yield a white powder (48% yield). $^1$H NMR (300 MHz, CDCl$_3$): δ 7.76 (2H, d, J=7.5 Hz), 7.59 (2H, d, J=6.9 Hz), 7.40 (2H, t, J=7.5 Hz), 7.31 (2H, t, J=7.5 Hz), 5.34 (1H, d, J=7.8 Hz), 4.49-4.59 (1H, m), 4.43 (2H, d, J=6.6 Hz), 4.22 (1H, t, J=6.6 Hz), 3.27 (2H, t, J=6.6 Hz), 1.3-2.0 (6H, m). ESI-MS m/e 395.

Fmoc-2-Azidooctyl amino acid (Fmoc-Az8-OH). The amino acid 3b was treated to Fmoc protection as described above. $^1$H NMR (300 MHz, CDCl$_3$): δ 7.75 (2H, d, J=7.5 Hz), 7.57-7.61 (2H, m), 7.39 (2H, t, J=7.5 Hz), 7.30 (2H, t, J=7.2 Hz), 5.40 (1H, d, J=8.1 Hz), 4.42-4.52 (1H, m), 4.40 (2H, d, J=7.2 Hz), 4.21 (1H, t, J=7.2 Hz), 3.23 (2H, t, J=6.9 Hz), 1.18-1.98 (14H, m). ESI-MS m/e 450.

Example 2

Construction of One-Bead-One-Compound Peptide Libraries

Materials. Fmoc-D-Ala-OH (Fmoc, fluoren-9-ylmethoxycarbonyl), Fmoc-D-Arg(Pbf)-OH (Pbf, pentamethyldihydrobenzofuran-5-sulfonyl), Fmoc-D-Asn(Trt)-OH (Trt, trityl), Fmoc-D-Asp(OtBu)-OH (tBu, tert-butyl), Fmoc-D-Glu(OtBu)-OH, Fmoc-D-Gln(Trt)-OH, Fmoc-Gly-OH, Fmoc-D-His(Trt)-OH, Fmoc-D-Ile-OH, Fmoc-D-Leu-OH, Fmoc-D-Lys(Boc)-OH (Boc, tert-butyloxycarbonyl), Fmoc-D-Met-OH, Fmoc-D-Phe-OH, Fmoc-D-Pro-OH, Fmoc-D-Ser(tBu)-OH, Fmoc-D-Thr(tBu)-OH, Fmoc-D-Trp(Boc)-OH, Fmoc-D-Tyr(tBu)-OH, and Fmoc-D-Val-OH were purchased from Anaspec (San Jose, Calif.) and used as received. TentaGel S—NH$_2$ resin (90 μm, 0.31 mmol/g) was obtained from Anaspec (San Jose, Calif.) and utilized for OBOC library construction. Fmoc-Rink Amide MBHA resin (50 μm, 0.67 mmol/g) was obtained from Anaspec (San Jose, Calif.) and utilized for bulk synthesis of hit peptide sequences. Amino acid coupling reactions were performed in 1-methyl-2-pyrrolidinone (NMP, 99%) with HATU (2-(7-Aza-1H-benzotriazole-1-yl)-1,1,3,3-tetramethylammonium hexafluorophosphate, ChemPep, Miami, Fla.) and N,N-diisopropylethylamine (DIEA) (99%, Sigma-Aldrich, St. Louis, Mo.). For removal of N$^α$-Fmoc protecting groups, a solution of 20% piperidine in NMP was used. For final deprotection of the peptide libraries, trifluoroacetic acid (98% min. titration) and triethylsilane (TES) were used (Sigma-Aldrich, St. Louis, Mo.).

Peptide library construction. Using the one-bead-one-compound (OBOC) combinatorial library methodology, randomized libraries of penta- to heptapeptides were synthesized peptide libraries were synthesized by a split-and-mix synthesis approach as previously reported (Lam, K. S. et al., 1997; Furka, A. et al., 1991; Geysen, H. M. and T. J. Mason, 1993).

In particular, randomized OBOC libraries of penta- to heptapeptides were synthesized manually via standard split-and-mix solid-phase peptide synthesis methods on 90 μm polyethylene glycol-grafted polystyrene beads (TentaGel S—NH$_2$, 0.31 mmol/g, 2.86×10$^6$ beads/g) (Lam, K. S. et al., 1997; Furka, A. et al., 1991; Geysen, H. M. and T. J. Mason, 1993). Non-natural D-stereoisomers (denoted by lowercase one-letter amino acid code) were used at every possible position in the peptide sequence. At least a 5-fold excess of beads was utilized in each library synthesis to ensure adequate representation of each library element. A standard solid-phase peptide synthesis method with Fmoc chemistry was used (Coin, I. et al., 2007). All wash, deprotection, and coupling steps were facilitated by 180-degree shaking of the resin. The resin was pre-swelled in NMP in a plastic fritted reaction vessel, and was separated into multiple aliquots. Each aliquot was reacted with 2-fold molar excess (relative to resin) of a single N$^\alpha$-Fmoc-amino acid. Amide coupling was initiated by addition of a 2-fold molar excess of HATU and a 6-fold molar excess of DIEA (Carpino; L. A. et al., 1994). The coupling reaction was run for 15 min. Another 2 equiv N$^\alpha$-Fmoc-amino acid, 2 equiv HATU, and 6 equiv DIEA were added, and allowed to react for 15 min ("double coupling"). In some cases, "triple coupling" with a third set of coupling reagents and N$^\alpha$-Fmoc-amino acid was performed (Table 1, Libraries D, E, F, and G). Following coupling, the aliquots were thoroughly washed (5×NMP), mixed together into a single vessel, and deprotected with 20% piperidine in NMP (30 min). The resin was thoroughly washed (5×NMP), dried (5×DCM), and re-divided into multiple equal-mass aliquots for the next cycle of coupling. The procedures were repeated until the desired length of peptide was attained.

The amino acid side-chain protecting groups were then removed by incubation in trifluoroacetic acid (95%), water (5%), and triethylsilane (2-fold molar excess per protected side chain) for 2 h at 25° C. The library resin was then neutralized with DMF, and washed thoroughly with DMF (5×), water (5×), methanol (MeOH, 5×), and methylene chloride (DCM, 5×) (Dixon, S. M. et al., 2006), and then dried under vacuum and stored in phosphate-buffered saline [PBS (pH 7.4)]+0.05% NaN$_3$ at 25° C.

Table 1 lists the libraries that were utilized in development of linear and branched biligand and triligand capture agents.

TABLE 1

Libraries Synthesized and Screened.[†]

| Library | Formula | Components | # of Unique Sequences |
|---|---|---|---|
| A | x$_1$x$_2$x$_3$x$_4$x$_5$ | x$_i$ = 19 D-amino acids (no D-Cys) | 2,476,099 |
| B | x$_1$x$_2$x$_3$x$_4$x$_5$x$_6$ | x$_i$ = r, k, l, w, f, h, y | 117,649 |
| C | Az$_n$-x$_2$x$_3$x$_4$x$_5$x$_6$-Az$_n$ | x$_i$ = 19 D-amino acids (no D-Cys) Az$_n$ = ⅓ Az4, ⅓ Az8, ⅓ no amino acid at all | 22,284,891 |
| D | x$_1$x$_2$x$_3$x$_4$x$_5$x$_6$-Tz1-kfwlkl | x$_i$ = k, l, w, f, i, g, v Tz1 = triazole formed between Az4 (on terminal k) and D-Pra (on x$_6$) | 117,649 |
| E | x$_7$x$_6$x$_5$x$_4$x$_3$x$_2$-Tz2-kwlwGl-Tz1-kfwlkl | x$_i$ = d, r, s, w, G, f, l Tz1 = triazole formed between Az4 (on terminal k) and D-Pra (on l) Tz2 = triazole formed between Az4 (on terminal x$_2$) and D-Pra (on k) | 117,649 |
| F | Az4-x$_2$x$_3$x$_4$x$_5$x$_6$x$_7$ | x$_2$ = r, n, l, i; | 3200 |
| G | x$_7$x$_6$x$_5$x$_4$x$_3$x$_2$-Tz2-kwlwGl-Tz1-kfwlkl | x$_3$ = w, f, l, i; x$_4$ = r, w, f, l, i; x$_5$ = w, f, v, l; x$_6$ = r, w, f, l, k; x$_7$ = f, r | 3200 |
| H | x$_1$x$_2$x$_3$x$_4$x$_5$x$_6$ | x$_i$ = k, w, f, i, g, l, v, Az4 | 262,144 |
| I | x$_1$x$_2$x$_3$-AZ4-x$_5$x$_6$ | x$_i$ = k, w, i, g, v, l, f | 16,807 |
| J | x$_0$x$_1$-k-x$_3$-Az4-x$_5$-w | x$_0$ = a, G, l, i, v, y, w, f, s, t, e, d, h, p, r, n, q, k x$_1$ = k(N$^\epsilon$-Aloc), w, v x$_3$ = v, w, r, n, q, d, k, s, t, h, G, a. x$_5$ = f, l, r, n, q, d, k, s, t, h, G, a | 7776 |

[†]Randomized positions are denoted by x (for D-amino acids) and Az$_n$ (for azide-containing artificial amino acids).

Example 3

General Screening Procedures

Providing protein target. Carbonic anhydrase II (bCAII) served as the target for proof-of-concept development of multi-ligand protein capture agents. The bCAII (C2522), from bovine erythrocytes, lyophilized powder, ≥3,000 W-A units/mg protein was obtained from Sigma-Aldrich (St. Louis, Mo.) and used as received. The protein was dye-labeled with the Alexa Fluor 647 Microscale Protein Labeling Kit (Invitrogen, Carlsbad, Calif.) following the manufacturer's protocol for low degree of labeling (DOL). Briefly, 100 μg protein was incubated with 6 mol equiv Alexa Fluor 647 NHS ester for 15 min at 25° C. Excess dye was removed by BioGel P-6 size exclusion resin. The labeled protein (bCAII-Alexa647) was characterized by UV-Vis and mass spectrometry.

Screening procedures suitable for ligand screening is summarized as follows. A typical peptide anchor ligand screen began with a library incubation in PBS (pH 7.4)+0.1% Tween 20+0.1% bovine serum albumin (BSA)+0.05% NaN$_3$ (PBST-BNaN$_3$) for 1 h, with shaking, to block non-specific protein binding (Lehman, A. et al., 2006). The library was then washed with 3×5 mL PBSTBNaN$_3$. On-bead multi-ligand screens were conducted at an appropriate bCAII-Alexa Fluor 647 dilution (see Table 2 and scheme in FIG. 24), and then washed with 3×5 mL PBSTBNaN$_3$, 3×5 mL PBS (pH 7.4)+ 0.1% Tween 20, and finally 6×5 mL PBS (pH 7.4). All in situ multi-ligand screens contained an additional 2 h pre-incubation of bCAII-Alexa Fluor 647 with peptide anchor ligand (typically ≥2000 equiv. relative to protein), after which the bead library was added to this mixture and the screen was continued (see Table 2 and scheme in FIG. 24). Following screens for in situ multi-ligands, beads were washed with 3×5 mL PBSTBNaN$_3$, 3×5 mL PBS (pH 7.4)+0.1% Tween 20, and then 6×5 mL PBS (pH 7.4).

A summary of the screening conditions used for Libraries A to J of Example 2 is reported on Table 2 below.

every two methylene units added to the azidoalkyl side chain. Fmoc-Az2-OH was synthesized according to literature protocol (Roice, M. et al., 2004), while Fmoc-Az6-OH was synthesized according to Scheme 1 of Example 1 above.

Example 4

Screening Approaches: First Generation Anchor Ligands

Screening for anchor ligand. In particular, first-generation screens were conducted using the pentamer Library A (4 g, ~2,500,000 beads) prepared as described in Example 2 above and illustrated in FIG. 19. In particular, Library A was sepa-

TABLE 2

Screening summary.

| Screen | Library | [bCAII-AF647] | Time (h) | % hit beads | Buffer | Other components |
|---|---|---|---|---|---|---|
| An1 | A | 100 nM | 1 h | 0.02% | PBS | |
| An2a | B | 50 nM | 1 h | 0.09% | PBS | |
| An2b | B | 8 nM | 24 h | 2 hits | PBS | |
| Bi1 | C | 50 nM | 2 h; 37° (no beads) + 48 h; 37° | 0.007% | PBS + 1% DMSO (v/v) | 100 µM of lklwfk-(D-Pra) |
| Bi2a | D | 50 nM | 17 h | 0.07% | PBSTBNaN$_3$ | |
| Bi2b | D | 10 nM | 17 h | 0.008% | PBSTBNaN$_3$ | |
| Tri1 | C | 50 nM | 2 h (no beads) + 15 h | 0.007% | PBSTBNaN$_3$ + 1% DMSO (v/v) | 100 µM of (D-Pra)-kwlwGI-Tz1-kfwlkl |
| Tri2 | E | 10 nM | 17 h | 0.008% | PBSTBNaN$_3$ | |
| TriX | A | 10 nM | 17 h | 0.007% | PBSTBNaN$_3$ + 1% DMSO (v/v) | 100 µM of (D-Pra)-kwlwGI-Tz1-kfwlkl |
| Tri3 | F | 0.5 nM | 2 h (no beads) + 18 h | 0.005-0.01% | PBSTBNaN$_3$ + 1% DMSO (v/v) | 100 µM of (D-Pra)-kwlwGI-Tz1-kfwlkl |
| Tri4 | G | 0.25 nM | 18 h | 0.005-0.01% | PBSTBNaN$_3$ | |
| BrBi1 | H | 50 nM | 2 h; 37° (no beads) + 18 h; 37° | 0.01% | PBSTBNaN$_3$ + 1% DMSO (v/v) | 100 µM of lklwfk-(D-Pra) |
| BrBi2 | I | 10 nM to 500 pM | 2 h (no beads) + 15 h | 0.06%-0.006% | PBSTBNaN$_3$ + 1% DMSO (v/v) | 40 µM of lklwfk-(D-Pra) |
| BrBi3 | J | 10 nM | 2 h (no beads) + 6 h; 37° C. | 0.07% | PBSTBNaN$_3$ + 1% DMSO (v/v) | 40 µM of lklwfk-(D-Pra) |
| BrTri1 | C | 50 nM | 2 h (no beads) + 16 h | 0.003% | PBSTBNaN$_3$ + 1% DMSO (v/v) | 100 µM branched biligand anchor |

All screens were conducted at pH = 7.4 and T = 25° C., unless otherwise noted.

Screened beads were transferred onto a glass microscope slide and immediately imaged for fluorescence using a GenePix 4200 array scanner ($\lambda_{ex}$=635 nm). The hit beads were selected manually by glass micropipette. To remove bound proteins, each hit bead was incubated in 7.5 M guanidine hydrochloride (pH 2.0) for 1 h, followed by ten rinses with water.

Single hit beads were sequenced by Edman degradation. In particular, Edman sequencing was carried out on a Model 494 Procise cLC Sequencing System (Applied BioSystems, Foster City, Calif.). Iterative N-terminal chemical degradation cycles yield direct positional amino acid information. Each degradation cycle produces one PTH-amino acid (PTH=phenylthiohydantoin) product that is analyzed by HPLC and identified by retention time as compared with PTH-amino acid standards. To allow for resolution of artificial azide-containing amino acids by this method, a custom Edman degradation method was utilized, which includes extended gradient and flask cycles.

The Edman traces corresponding to elution of Az2, Az4, Az6 and Az8 demonstrate a 6-min retention time increase for rated into 10 mg portions in polypropylene fritted tubes. Then, bCAII-Alexa647, at 100 nM dilution in 1 mL PBS [20 mM sodium phosphate, 150 mM NaCl (pH 7.4)], was incubated with each library portion for 1 h at 25° C., with shaking. The screened beads were washed with 3×5 mL PBS (pH 7.4) and 7×5 mL water. The beads were transferred onto a glass microscope slide in a minimal amount of water and immediately imaged for fluorescence using a GenePix 4200 array scanner. The hits were selected manually by glass micropipette. To remove bound proteins, each hit bead was incubated in 7.5 M guanidine hydrochloride (pH 2.0) for 1 h, followed by ten rinses with water.

Hit sequences were then decoded by Edman degradation. Histogram analysis was used to analyze the hit sequences for amino acid frequency and for positional sequence homology among samples. An example of a first-generation anchor ligand analysis is presented in FIG. 25.

Figure 25:
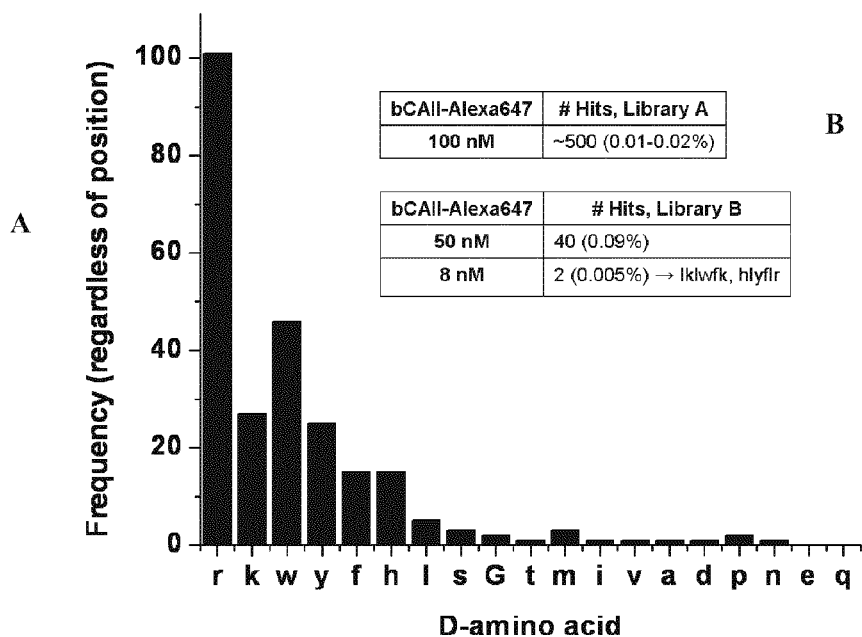
FIG. 25 shows a diagram illustrating results of a method for selecting a primary or anchor ligand of multi-ligand capture agents according to some embodiments herein described. Panel A shows a diagram plotting frequency vs. D-amino acid for 51 hit sequences isolated from screening Library A (first-generation anchor ligand screen). Panel B shows hit rates for Library A and B (second-generation anchor ligand) screens, leading to the selection of 2 anchor ligands.

In particular in the illustration of FIG. 25 the frequency vs. D-amino acid for 51 hit sequences isolated from screen An1 is shown in Panel A. The hit rates for screens An2a and An3b are shown in Panel B of FIG. 25, leading to the selection of 2 peptide anchor ligands.

From this, it was determined that basic/charged (k, r) and aromatic residues (y, f, w) were important amino acids in an anchor ligand for bCAII and used those amino acids to build focused Library B according to procedures illustrated in the following Example 5.

Example 5

Screening Approaches: Second Generation Anchor Ligands

Focused Library B was constructed according to the procedure exemplified in Example 2, to reflect the highly occurring amino acids identified according to procedures exemplified in Example 4.

Specifically, the amino acids k, r, y, f, w, h, and l were included and the peptide length was increased to a hexamer. The tighter distribution of constituent amino acids and increased peptide length was shown to enrich the second-generation screen to select even more specific anchor ligands.

Second-generation anchor ligand screens were then conducted using one copy of Library B (40 mg, ~120,000 beads), following similar protocols to screen An1 illustrated in Example 3 above. Here, 8 to 50 nM bCAII-Alexa647 dilutions in 4 mL PBS (pH 7.4) were incubated with the library for 1 to 24 h at 25° C., with shaking.

Reference is made to FIG. 25B illustrates the results of the second-generation screens An2a and An2b (see also FIG. 19). Here, hits were isolated at even lower protein concentration and with lower frequency.

The most stringent screen yielded two hits, hlyflr and lklwfk, which represent the two selected anchor ligands.

Example 6

Synthesis and Affinity Measurement for the Anchor Ligand

Peptide synthesis. Hits from screen An2b were re-synthesized to contain the appropriate artificial amino acid (azide/acetylene) linkers at their termini to make them suitable for click chemistry. Bulk synthesis of hit peptide sequences was performed on either Fmoc-Rink amide MBHA (50 µm, 0.67 mmol/g) or 2-chlorotrityl chloride (1.5 mmol/g) resins (Anaspec; San Jose, Calif.), on a typical resin scale of 0.3 g per sequence. Crude peptides were precipitated with ether, and then purified to >98% by HPLC (Beckman Coulter System Gold 126 Solvent Module and 168 Detector, Fullerton, Calif.) on a $C_{18}$ reversed phase semi-preparative column (Phenomenex Luna 10 µm, 250×10 mm). The pure peptides were used for affinity measurements, screens, and binding assays. Hit peptide sequences were also re-synthesized on TentaGel S—$NH_2$ on a similar resin scale, and used for on-bead binding assays.

$K_D$ determination by fluorescence polarization. The N-terminus of the anchor ligand was labeled with fluorescein isothiocyanate (FITC) following published protocols (Yin, H. et al., 2006). After resin cleavage, the crude fluoresceinated anchor ligand was precipitated with ether and then purified to >98% by $C_{18}$ reversed phase HPLC.

Luminescence spectra were recorded by Fluorolog2 spectrofluorimeter (Jobin Yvon, Longjumeau, France) in the Beckman Institute Laser Resource Center (Pasadena, Calif.). All samples contained 6 µM fluoresceinated anchor ligand and varying concentrations of bCAII (0.2 µM to 800 µM) in PBS (pH 7.4)+3% (v/v) DMSO. Stock protein and anchor ligand concentrations were verified by UV-Vis using $\epsilon_{280}$ (bCAII)=57,000 $M^{-1}cm^{-1}$ or $\epsilon_{494}$ (FITC, 0.1 N NaOH)=68,000 $M^{-1}$ $cm^{-1}$ for fluoresceinated under ligand. Samples were excited at 488 nm (2-nm band-pass), and luminescence spectra were obtained between 500 nm and 700 nm (4-nm band-pass). All measurements were taken at 2-nm intervals with 0.5 s integration times at 25° C. All luminescence spectra were subjected to background subtraction.

The ratio of sensitivities (G) for the vertically and horizontally plane-polarized light in the system was calculated by the equation $G=I_{HH}/I_{HV}$ using the $I_{HH}$ and $I_{HV}$ luminescence spectra obtained from a peptide-only sample. The luminescence spectra $I_{VV}$ and $I_{VH}$ were integrated, and the fluorescence polarization value (P) was obtained by applying Equation 1.

$$P = \frac{I_{VV} - GI_{VH}}{I_{VV} + GI_{VH}} \quad (1)$$

The polarization values were fitted with a sigmodial dose-response curve using the Origin 6.1 (Northampton, Mass.).

Figure 26:
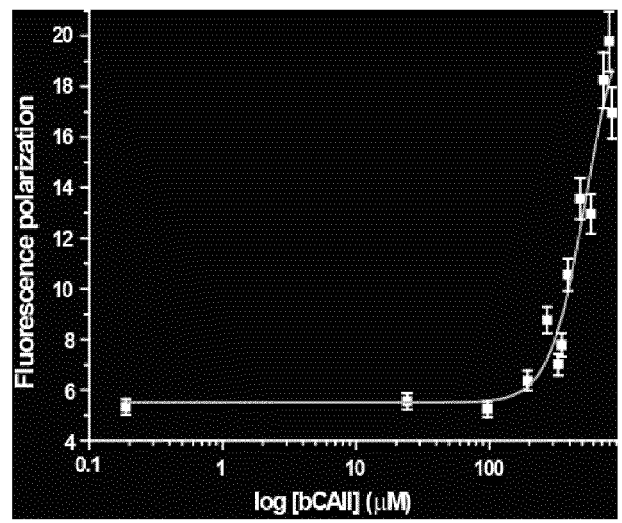
FIG. 26 shows a diagram illustrating detection of affinity for a ligand or a multi-ligand capture agent according to some embodiments herein described. In particular, the diagram of FIG. 26 illustrates the results of fluorescence polarization experiments for a fluoresceinated anchor ligand titrated with increasing concentrations of the target (0.2 $\mu$M to 800 $\mu$M), and suggests a 500 $\mu$M affinity for this binding interaction.

By this method, a 500-µM affinity for bCAII was measured for the fluoresceinated anchor ligand lklwfk-(D-Pra). The fluoresceinated anchor ligand titrated with increasing concentrations of the target (0.2 µM to 800 µM), and suggests a 500 µM affinity for this binding interaction (FIG. 26).

Example 7

Identification of Secondary Ligands: Biligand Screens

Secondary ligands were identified by two complementary approaches: 1) in situ biligand screens; 2) on-bead biligand screens. (see FIG. 24)

In situ biligand screen: In the first approach (see FIG. 20 and FIG. 24A), the peptide anchor ligand and protein are in solution, and the cognate library of secondary ligands is on-bead. The protein is acting as a catalyst for the in situ assembly of the biligand on-bead.

In the screen Bi1, a solution of 50 nM bCAII-Alexa647 was pre-incubated with peptide anchor ligand (lklwfk-(D-Pra), 2000×relative to protein) for 2 h at 37° C. Screens were conducted using the azide heptamer Library C (4 g, ~2,250,000 beads) separated into 60 mg portions per polypropylene fitted tube. The anchor ligand/protein solution was added to the bead library and incubated for 48 h at 37° C., with shaking. The screened beads were washed with 3×5 mL PBS (pH 7.4) and 7×5 mL water. The beads were imaged for fluorescence using the protocol outlined in Example 3. Hits, representing in situ biligands, were selected manually by micropipette. The selected beads were then processed to remove bound protein [7.5 M guanidine hydrochloride (pH 2.0)], and the sequences of the secondary ligands were obtained by Edman degradation.

Figure 27:
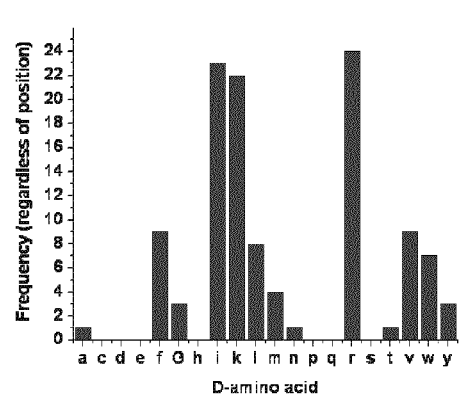
FIG. 27 shows identification of a secondary ligand of a multi-ligand capture agent according to some embodiments herein described. Panel A shows a diagram illustrating frequency (y-axis) of D-amino acids (x-axis) for secondary ligand candidates of a biligand capture agent isolated from a screening library in presence of an anchor ligand and target. Panel B shows an abbreviated list of the exact secondary ligand sequences isolated from the screening library of Panel A.

FIG. 27 illustrates the result of this first-generation in situ biligand screen Bi1. From a histogram analysis and raw analysis of hit secondary ligands in this first-generation in situ biligand screen Bi1, a secondary ligand candidate emerged (Az4-kiwiG), whose motif was repeated over several hit samples. In particular, FIG. 8A 27A shows the frequency vs. D-amino acid histogram for secondary ligand candidates isolated from screening Library C in the presence of 100 µM anchor ligand (lklwfk-(D-Pra)). FIG. 27B shows an abbreviated list of hit sequences isolated from screening Library C against 50 nM bCAII-Alexa647.

The method for screening secondary ligands by in situ biligand assembly can be validated by a pairwise screen. In particular, pairs of anchor ligand and secondary ligand are combined in solution in the presence of protein target. The protein-catalyzed assembly of the biligand capture agent is monitored by analytical methods such as those described by Manetsch, Krasiński et al. 2004 and Krasinski, Radić et al. 2005.

Pairwise screen. Stock solutions of secondary ligand (azide, Az4-kiwiG, 13.1 mM) and anchor ligand (acetylene, lklwfk-(D-Pra), 2.1 mM) were prepared in DMSO. Stock solutions of bCAII and bovine serum albumin (BSA) were prepared in PBS (pH 7.4). Each reaction contained 394 µM azide, 65 µM alkyne, and 36 µM protein in 100 µL PBS (pH 7.4)+6% DMSO (v/v). Reactions proceeded for 48 h at 37° C., followed by 5 days at 25° C. Reactions were quenched with 100 µL of 7.5 M guanidine hydrochloride (pH 2.0), and proteins were subsequently removed by centrifugal filtration (Microcon YM-3, Millipore, Billerica, Mass.).

The formation of in situ biligands was identified by MALDI-TOF mass spectrometry. Control experiments were conducted (1) in the absence of bCAII, and (2) replacing bCAII with BSA, to verify that the click reaction between the azide and alkyne is specific to the bCAII protein target. A third control, performed in the absence of protein, represents the slow thermally driven reaction between solutions of azide and alkyne.

Figure 28:
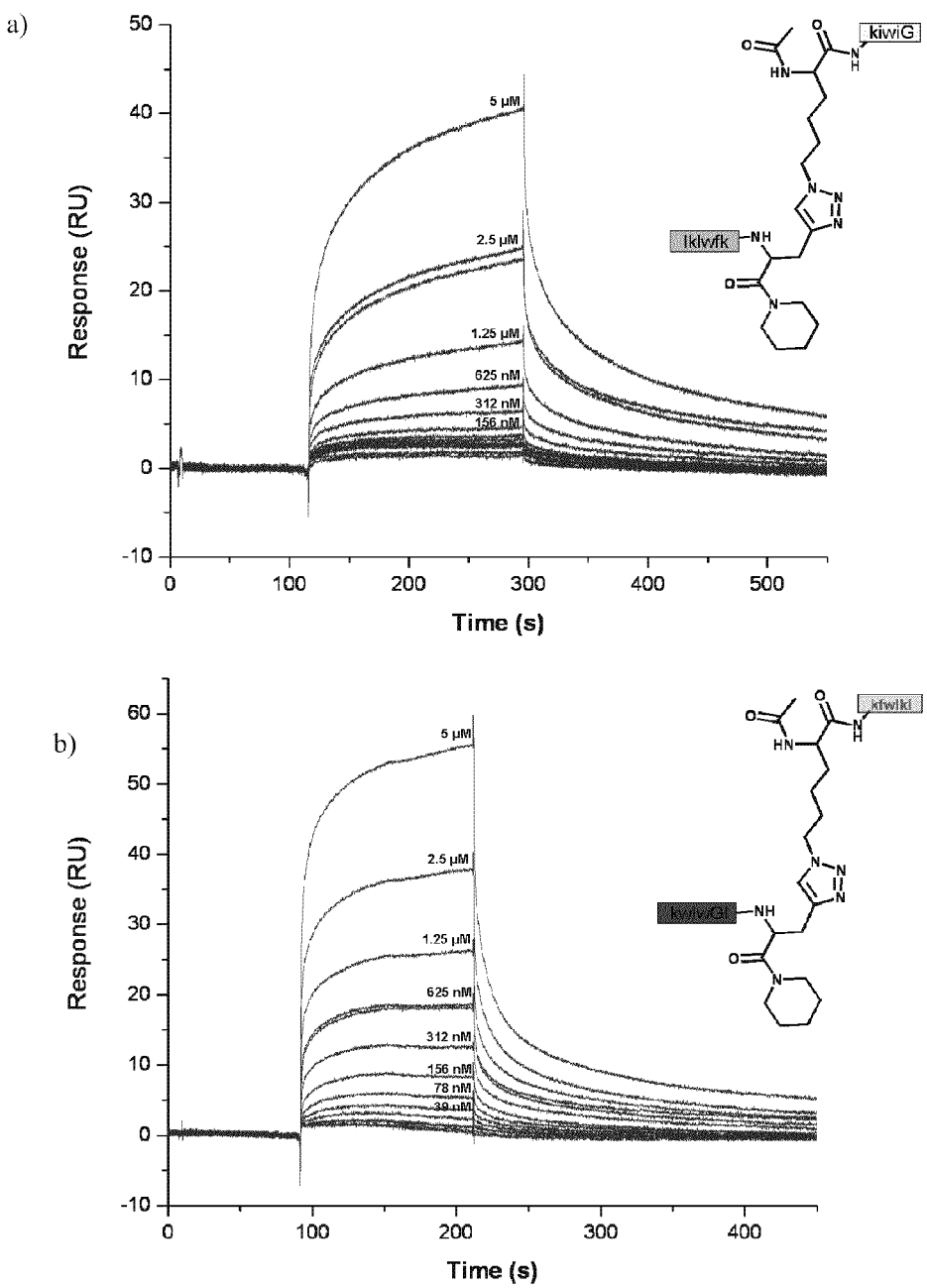
FIG. 28 shows diagrams illustrating variation of detected binding affinity for a multi-ligand capture agent with increasing concentration of the multi-ligand capture agent according to an embodiment herein described. In particular, the diagrams of FIG. 28 illustrate the results of surface plasmon resonance (SPR) experiments for the interaction of each of two biligand capture agents with the target immobilized on a sensor surface. Panel A shows SPR response sensorgrams obtained with increasing concentration of the biligand lkl-wfk-Tz1-kiwiG (2 nM to 5 $\mu$M). Panel B shows SPR response sensorgrams obtained with increasing concentration of the biligand kwlwGl-Tz1-kfwlkl (2 nM to 5 $\mu$M).
Figure 29:
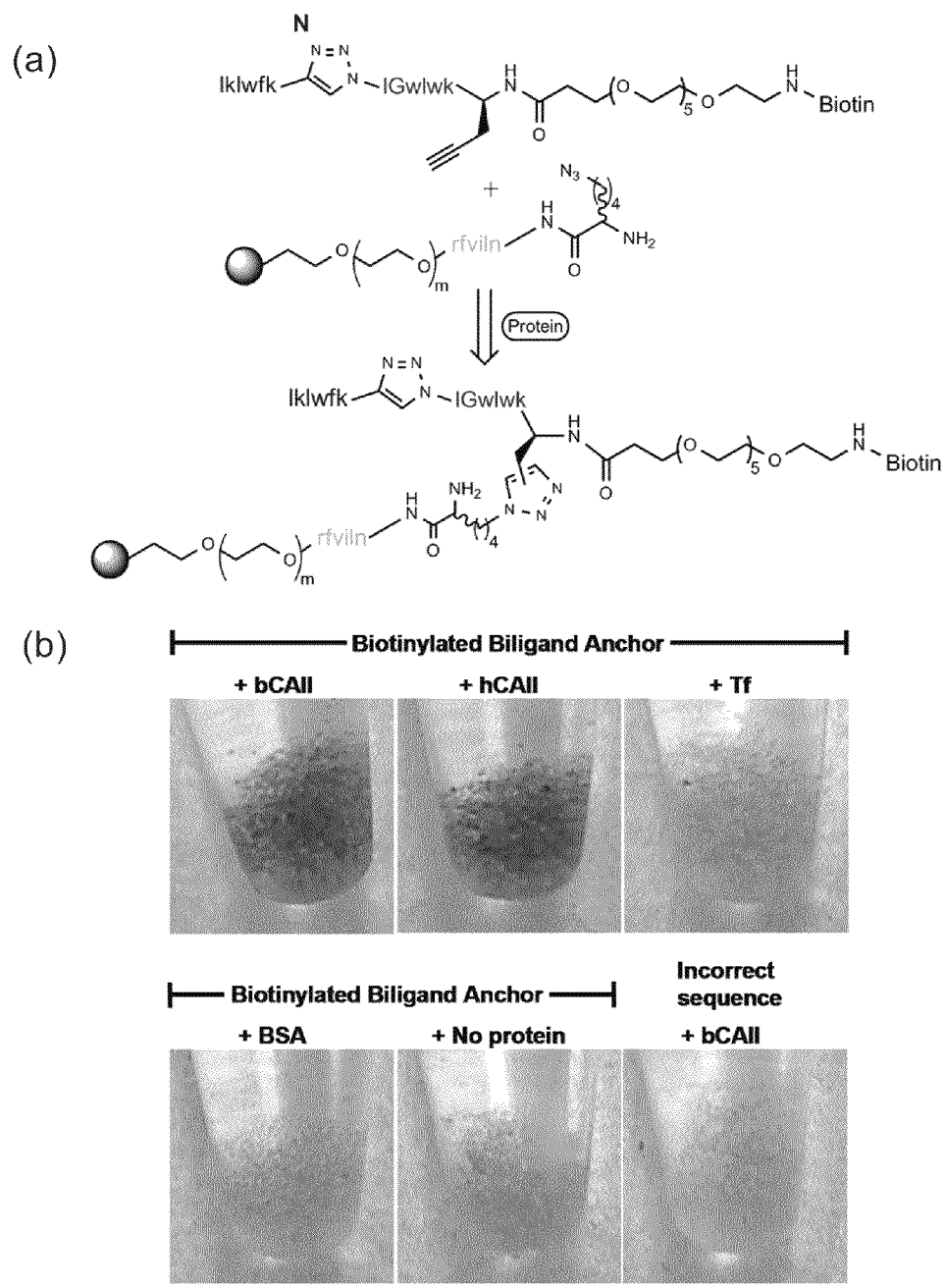
FIG. 29 shows a method for detecting the linkage between ligands of a multi-ligand capture agent according to some embodiments herein described. In particular, Panel A shows a schematic of in situ click assay for on-bead triazole formation, using a biotinylated biligand anchor, and Panel B shows purple beads (shown in dark grey) as a positive indicator of triazole formation.
Figure 30:
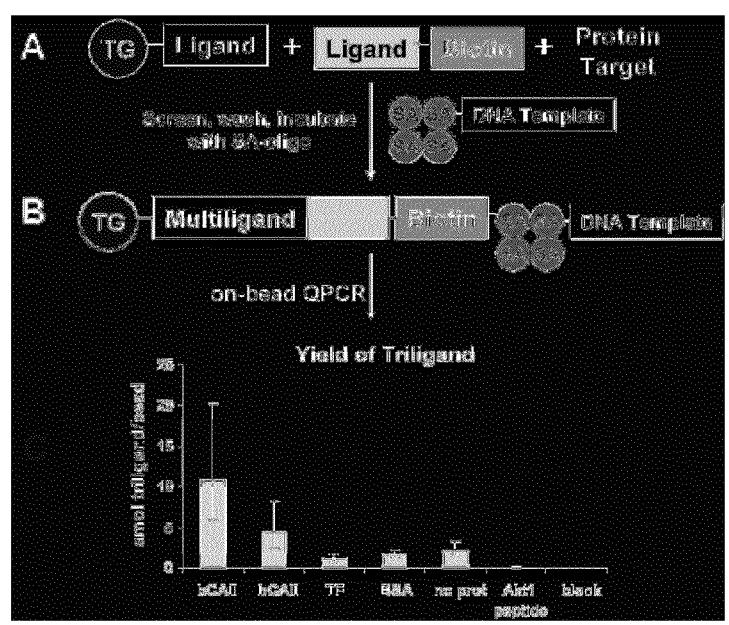
FIG. 30 shows a schematic representation of a method to detect a multi-ligand capture agent according to embodiments herein described. Panel A shows a schematic representation of a method for detecting the on-bead multi-ligand detection by QPCR, with the detection of a triligand as the exemplary case. Panel B illustrates a schematic representation of a quantitation of the formation of the biotinylated triligand of FIG. 29 performed by QPCR. Panel C shows a diagram illustrating data concerning the quantitation of Panel B and exhibits an approximate selectivity of 10:1 over the controls.

In MALDI-MS result of a pairwise screen, where the protein bCAII has catalyzed the turnover of an in situ biligand, illustrated in FIG. 28. Background reactions catalyzed by BSA or the thermal click reaction are low, proving that much of the biligand turnover can be attributed to bCAII. In certain embodiments, amplification of the products of pairwise screens can be performed as illustrated in FIG. 29 and FIG. 30 of Example 13.

On-bead biligand screen: In the second approach for identifying secondary ligands (see FIG. 24B) the peptide anchor ligand is covalently coupled to the on-bead library of secondary ligands via the copper(I)-catalyzed azide-alkyne cycloaddition (CuAAC). In particular, this library of pre-assembled biligands is screened against the protein target to yield secondary ligand candidates. The protein target is not a catalyst in this approach; this screen was used as a validation tool for comparison against the in situ capture agent screens.

Screens Bi2a and Bi2b were conducted using Library D (40 mg, ~120,000 beads) in a polypropylene fitted tube, following Example 3 above. To block non-specific protein binding, the library was first incubated in PBS (pH 7.4)+0.1% Tween 20+0.1% bovine serum albumin (BSA)+0.05% $NaN_3$ ($PBSTBNaN_3$) for 1 h, with shaking (Lehman, A. et al., 2006). Following this pre-blocking step, the library was washed with 3×5 mL $PBSTBNaN_3$. bCAII-Alexa647, at 10 to 50 nM dilution in 4 mL $PBSTBNaN_3$, was incubated with the library for 17 h at 25° C., with shaking. The screened beads were washed with 3×5 mL $PBSTBNaN_3$, then 3×5 mL PBS (pH 7.4)+0.1% Tween 20, and finally 6×5 mL PBS pH 7.4. The beads were imaged for fluorescence, and the hits were selected by micropipette. After washing the hits to remove bound protein [7.5 M guanidine hydrochloride (pH 2.0)], their sequences were determined by Edman degradation, following Example 3 above.

All secondary ligand sequences obtained by screens Bi2a and Bi2b display striking sequence homology. Several sequences were repeated more than once, including kwlwGl and kwiwGw.

Figure 31:
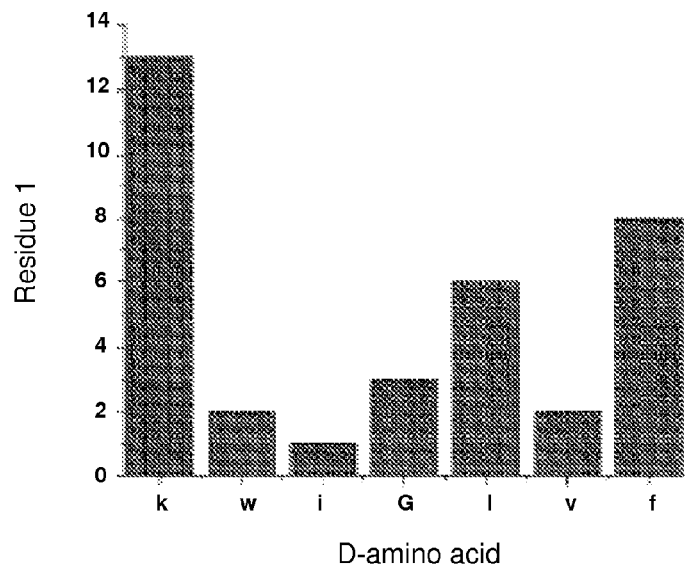
FIG. 31 shows diagrams illustrating screening of second generation ligands according to some embodiments herein described. In particular, the diagrams of FIG. 31 show distribution of D-amino acids found in positions 1-6 based on the analysis of 37 biligand hit beads. The frequency of an amino acid residue for each position is indicative of a consensus.
Figure 31:
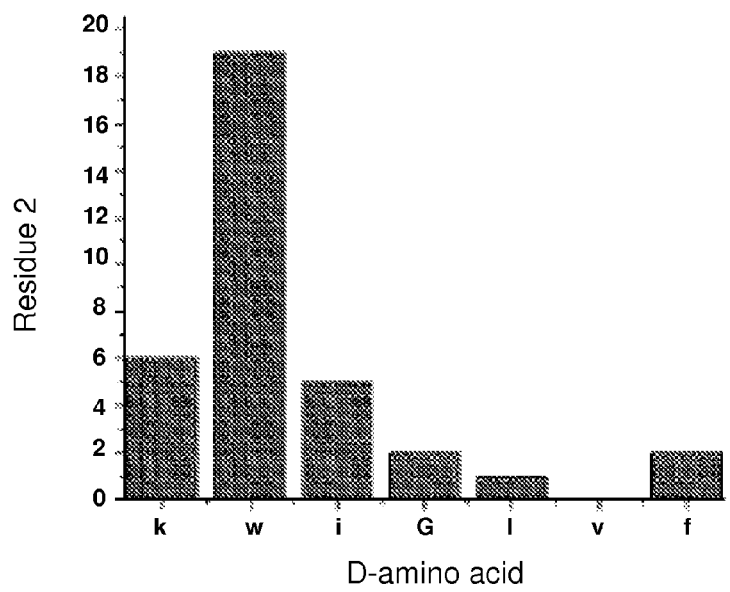
Figure 31:
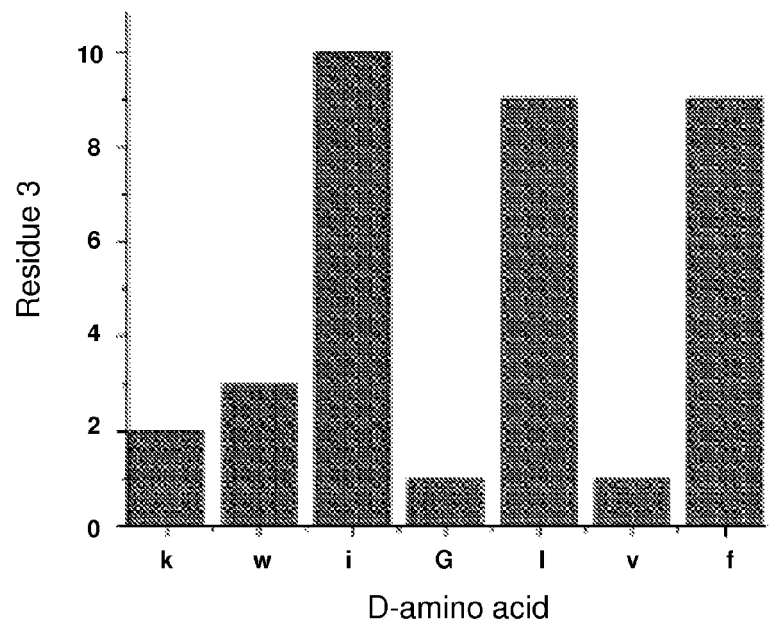
Figure 31:
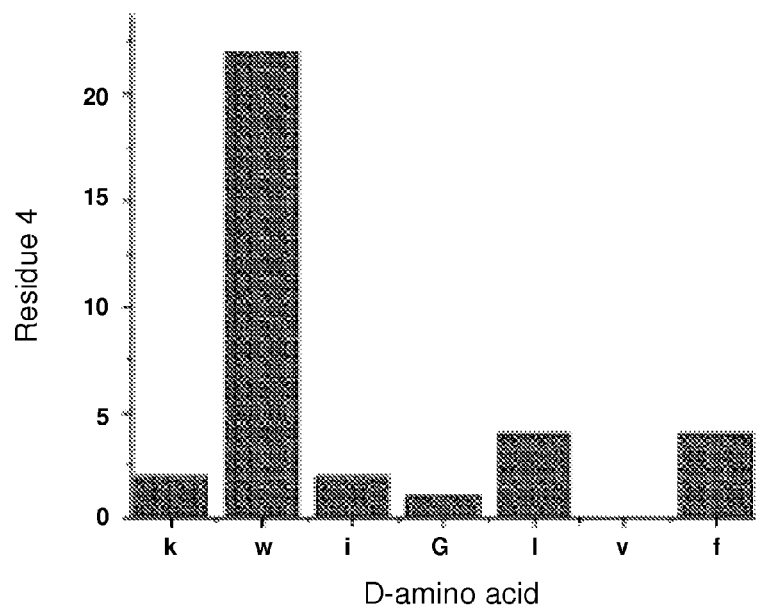
Figure 31:
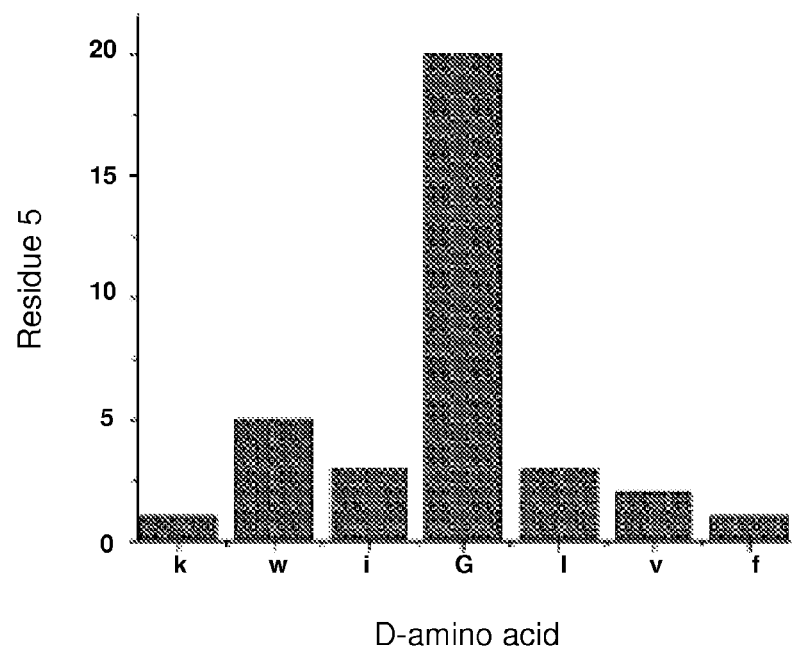
Figure 31:
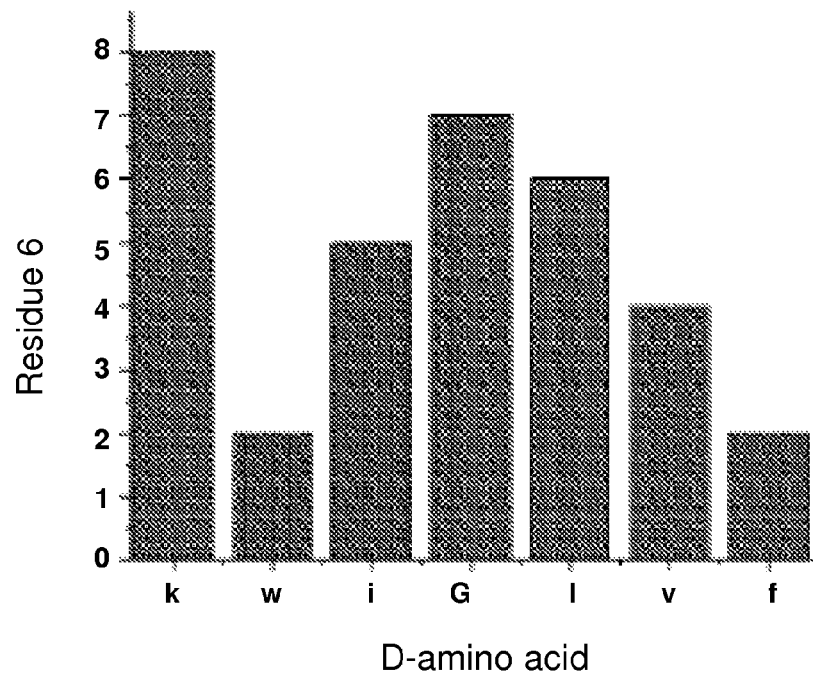

A residue-by-residue histogram analysis (FIG. 31) of all secondary ligand hits illustrates a strong preference for only one amino acid to be found at each Residue 1 (k), 2 (w), 4 (w), and 5 (G) in the secondary ligand component of the biligand capture agent. In particular, the distribution of D-amino acids illustrated in FIG. 31, found in positions 1-6 based on the analysis of 37 biligand hit beads, suggests the consensus sequence k-w-$x_3$-w-g (where $x_3$=hydrophobic amino acid).

Example 8

Utilization of a Biligand as an Anchor Ligand for Longer Multi-Ligand Capture Agent Once a biligand is identified, that biligand can serve as the FIG. 7 anchor ligand, and the same OBOC library is employed to identify a triligand, and so forth.

As shown in the illustration of FIG. 7, representation of a sequential in situ click chemistry screen to prepare a multi-ligand capture agent. 1°) A comprehensive OBOC peptide library on TentaGel (TG) beads ($x_i$=variable region) is incubated together with a fluorescently labeled protein target. Hits are identified by their fluorescence intensity, as detailed in Examples 4 and 5. 2°) Hit peptide from 1° screen is employed as an anchor ligand and incubated in the presence of the OBOC peptide library now appended with an azide linker (n=4, 8). Biligands are selected, as detailed in Example 7. 3°) Process is repeated but now employing the biligand from the 2° screen as the new anchor unit, allowing the rapid identification of higher order multi-ligands.

With the addition of each ligand to the capture agent, the affinity and the selectivity of that capture agent for its cognate protein rapidly increase. The FIG. 7 screen was used to identify lklwfk-(D-Pra) as the anchor ligand and (D-Pra)-kwlwGl-Tz1-kfwlkl as the biligand, and ultimately implemented (D-Pra)-kwlwGl-Tz1-kfwlkl as the anchor ligand for identification of a triligand against bCAII, according to the procedures exemplified in Examples 2 to 7.

The biligand kwlwGl-Tz1-kfwlkl against bCAII exhibited a 3 µM binding affinity to bCAII, as measured by surface plasmon resonance (SPR) as illustrated in Example 9 below (see also Example 10 for SPR procedures). The measured dissociation constant for this biligand is 150 times better than that measured for anchor ligand lklwfk-(D-Pra) interacting with the target.

Example 9

Biligand Synthesis Using On-Bead Click Reaction

Identification of specific biligand for bCAII, plus affinity measurements were performed as described below.

Materials. For peptide biligand synthesis, acetylation reagents (acetic anhydride, 2,6-lutidine, and N,N-dimethylformamide (DMF)) were purchased from Sigma-Aldrich (St. Louis, Mo.). For the on-bead Cu(I)-catalyzed click reaction, copper(I) iodide, L-ascorbic acid, and sodium diethyldithiocarbamate trihydrate were purchased from Sigma-Aldrich (St. Louis, Mo.).

On-bead biligand synthesis. Biligand synthesis was completed in four steps: (1) anchor ligand synthesis, (2) acetylation, (3) click reaction, and (4) addition of secondary ligand sequence according to procedures exemplified in the preceding examples. Scheme 2 illustrates the acetylation and click reactions. For the acetylation, the fully protected TentaGel S—$NH_2$ bead-bound sequence (0.420 g, 0.13 mmol) was capped by a solution of acetic anhydride (1 mmol) in DMF, containing a catalytic amount of 2,6-lutidine.

The acetylated peptide was reacted with Fmoc-D-Pra-OH (0.218 g, 0.65 mmol) in the presence of copper(I) iodide (0.124 g, 0.65 mmol), L-ascorbic acid (0.114 g, 0.65 mmol), and DMF/piperidine (8/2) at 25° C. for 6 h (Zhang, Z. and E. Fan, 2006). The reaction solution was drained from the resin, and the resin was washed with 5×5 mL sodium diethyldithiocarbamate trihydrate ($Et_2NCSSNa.3H_2O$, 1% w/v), containing 1% DIEA (v/v) in DMF to remove excess coordinated copper following the click reaction (Weterings, J. J. et al., 2006).

In particular, the biligand anchor (D-Pra)-kwlwGl-Tz1-kfwlkl was synthesized on 2-chlorotrityl chloride (1.6 mmol/g) resin (Anaspec, San Jose, Calif.) using Scheme 2. The biligand anchor was released either as the fully deprotected peptide by cleavage with 95:5 TFA:water (+2 mol equiv triethylsilane scavenger per side chain protecting group), or as the fully protected peptide by cleavage with 99:1 DCM:TFA (Garcia-Martin, F. et al., 2007). To facilitate the on-bead click reaction, it is noted that the 1° ligand was synthesized here as Az4-kfwlkl (displaying N-terminal $Az_n$ modification), and to this sequence was coupled D-Pra and the 2° ligand to produce the linear biligand.

Scheme 2 illustrates the method for installing a 1,2,3-triazole to join an anchor ligand to a secondary ligand of a biligand or longer multi-ligand.

SCHEME 2

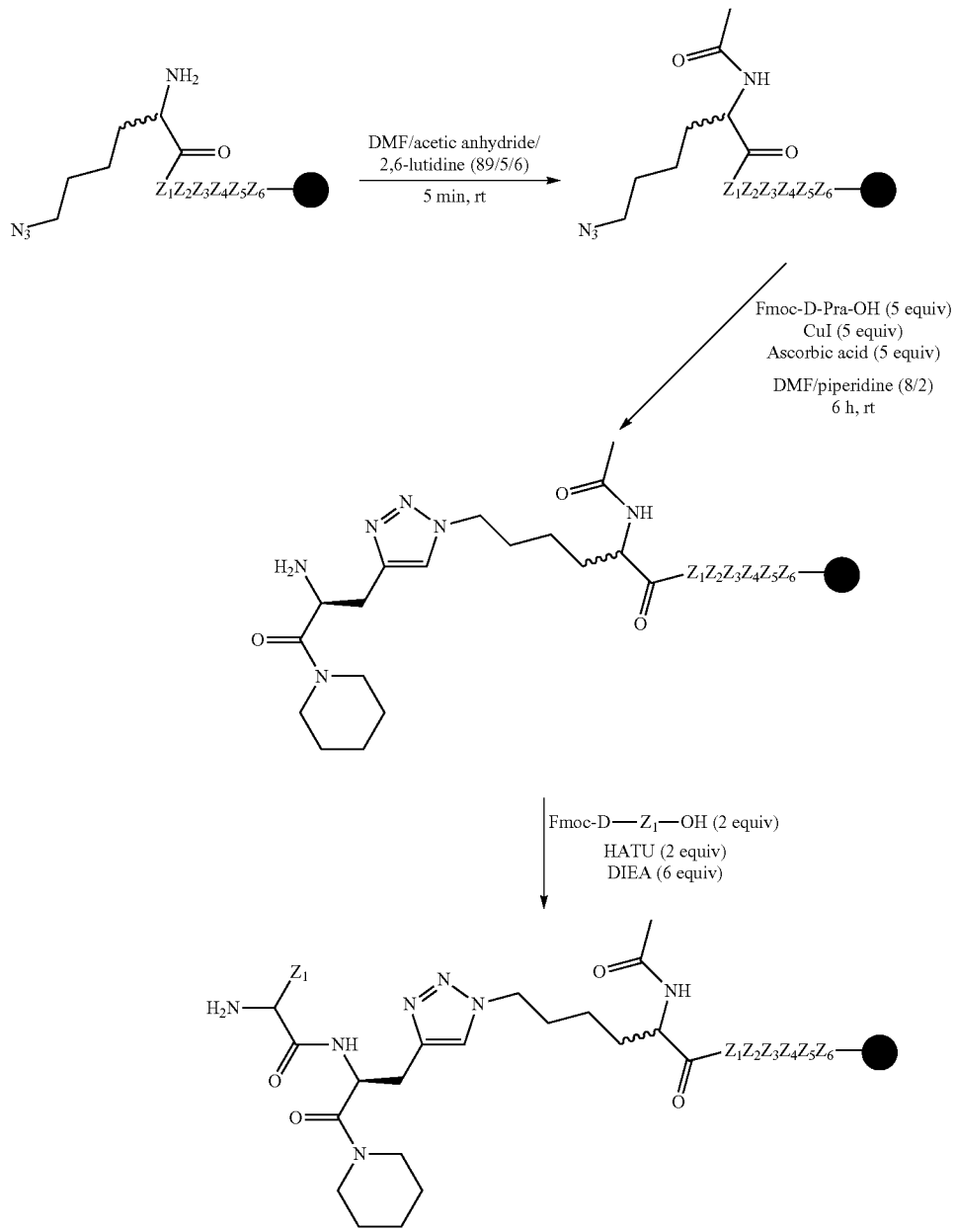

Example 10

Affinity Measurements for Biligands $K_D$ determination by surface plasmon resonance (SPR). Immobilization and biligand sensing experiments were performed by Biacore T100 SPR (California Institute of Technology Protein Expression Center, Pasadena, Calif.). One flow cell of the biosensor surface (Biacore CM5) was immobilized with bCAII following standard procedures using 0.25 mg/mL bCAII prepared in 10 mM sodium acetate (pH 5.0) buffer and a 1:1 solution of 0.1 mM NHS and 0.4 mM EDC (Papalia, G. A. et al., 2006). Similarly, a second flow cell was immobilized with hCAII following standard procedures using 0.25 mg/mL hCAII prepared in 10 mM sodium acetate (pH 5.5) buffer (Svedhem, S. et al., 2001). Immobilization levels of ~4000 RU were achieved using a flow rate of 100 µL/min over 420 s. The remaining two flow cells were left underivatized, to correct for changes in bulk refractive index and to assess nonspecific binding. The running buffer was prepared to contain 10 mM HEPES+150 mM NaCl+0.05% Tween20+3% DMSO, and this buffer was used for all experiments. Prior to the peptide analyte experiment, 8 buffer-alone cycles were completed to establish baseline stabilization. Biligand samples were injected in a concentration series (5 µM to 2 nM) at 100 µL/min flow rate for 120-180 s across the four flow cells. Following background subtraction, the analyte response data was fitted for 1:1 binding affinity using the BiaEvaluation software.

The binding responses (FIG. 28) reveal $10^{-6}$ M affinity of two biligands toward bCAII. This proves that the in situ biligand screen, whose selected biligand is depicted in FIG. 28A, and the on-bead biligand library screen, whose selected biligand is depicted in FIG. 28B, converge on similar biligand sequences with similar affinities.

In particular, FIG. 28A shows SPR data sets for the biligand selected from in situ screen Bi1, implementing Library C indicate that $K_D$=11 µM. FIG. 28B shows SPR data sets for the biligand selected from on-bead screen Bi2b, implementing Library D indicate that $K_D$=3 µM. These equilibrium dissociation constants represent a 150-fold affinity enhancement compared to the interaction between anchor ligand and target FIG. 26).

In view of the above, the biligand anchor (D-Pray-kwlwGl-Tz1-kfwlkl was synthesized (Mol. Wt.: 1993.49).

Example 11

Identification of a Triligand Capture Agent

With the biligand (D-Pra)-kwlwGl-Tz1-kfwlkl serving as the new anchor unit, the FIG. 7 screen was repeated with Library C (see Examples 2, 3, and 7) to identify a triligand rfviln-Tz2-kwlwGl-Tz1-kfwlkl (FIG. 6) that exhibited 60 nM and 45 nM binding affinities against bCAII and hCAII, respectively, by SPR.

Figure 32:
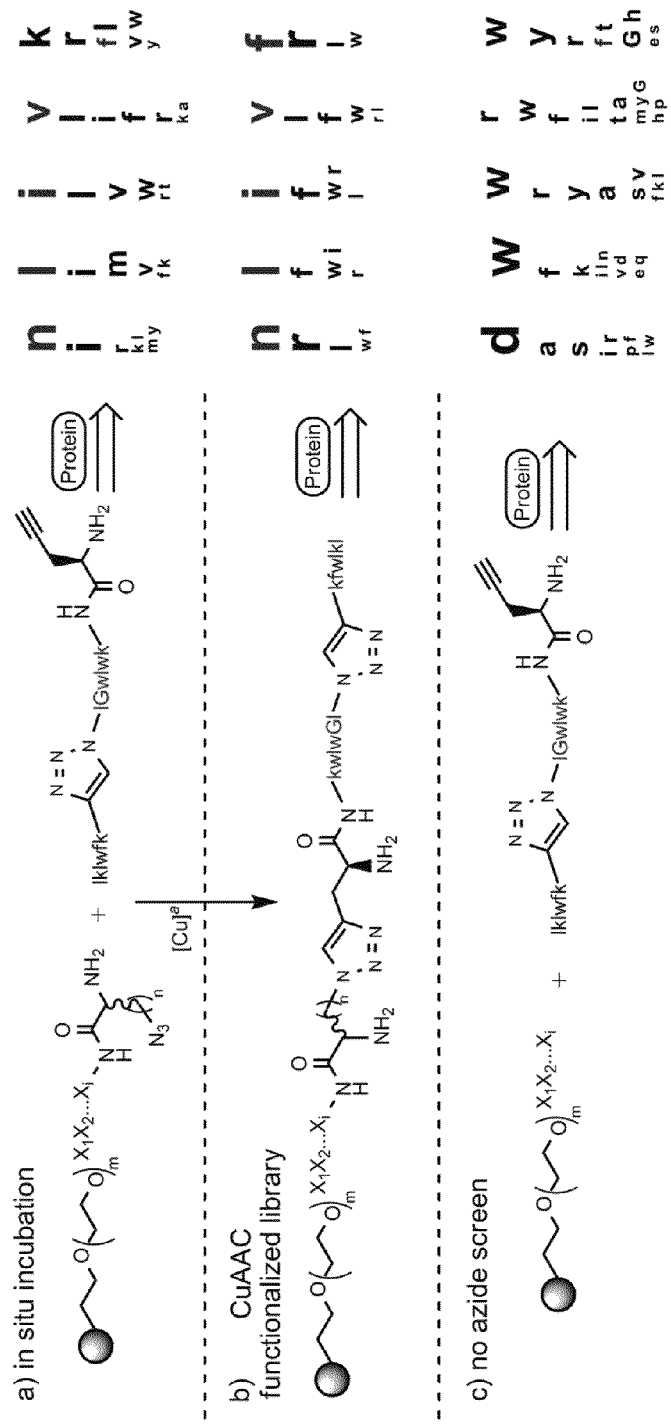
FIG. 32 shows a schematic illustration of method to validate formation of a multi-ligand capture agent according to some embodiments herein described. In particular, position-dependent histograms for the first-generation tertiary ligand screens, for peptides (Panel A) with and (Panel C) without an azide-containing amino acid, to generate a triligand are illustrated, together with (Panel B) first- and second-generation CuAAC library screens. The final consensus triligand sequence is indicated by grey fonts.

For the case of the in situ triligand screens, using FIG. 7, a histogram charting the position-dependent frequency of amino acids observed in the hit beads was generated (FIG. 32). The consensus tertiary ligand was Az4-nlivfr.

FIG. 32 shows position-dependent histograms for the first-generation in situ click screens, for peptides (a) with and (c) without an azide-containing amino acid, to generate a triligand. (a) For the in situ screen (Tri1), ⅓ of the beads had no azide at the $x_1$ or $x_7$ positions, but all hit beads contained an azide. (b) First- and second-generation CuAAC library screens (Tri2 and Tri4), where the 3° ligand variable region was coupled, via CuAAC (Tz2; FIG. 32), to the biligand, yielded independent validation of the in situ result. The final, consensus triligand sequence is indicated by grey font. Both this on-bead triligand screen, and the in situ screen, yielded the same consensus sequence and confirmed the equivalence of the two types of screens. (c) In the absence of azide, the in situ triligand screens yielded completely different, and much less homologous, hit sequences because the triligand capture agent was prohibited from forming (control screen TriX implemented). This result illustrates the importance of the functional groups, such as azide and acetylene, interacting on the surface of the target to form a multi-ligand capture agent. Sample size: in situ=25 hits; in situ no azide=24 hits; CuAAC library=21 hits.

The consensus tertiary ligand obtained by second-generation in situ screen Tri3 resembles almost exactly the tertiary ligand isolated by the first-generation screen (Tri1). Such sequence homology is unique to the in situ screens, which display target-guided selection.

Example 12

Triligand Synthesis Using On-Bead Click Reaction

Composed of individual 6-mers, the triligand can be prepared in bulk quantities by standard solid-phase synthesis and then the individual segments ligated via the Cu(I)-catalyzed azide-alkyne cycloaddition (CuAAC) [Tornøe and Meldal, "Peptidotriazoles: Copper(I)-Catalyzed 1,3-Dipolar Cycloadditions on Solid-Phase" in Peptides: The Wave of the Future (Lebel and Houghten, eds., 2001), p. 263; Tornøe et al., J. Org. Chem. 67(9):3057-3064 (2002); Rostovtsev, V. V. et al., 2002].

Alternately, triligand synthesis can be performed on bead. The Cu(I)-catalyzed click chemical reaction was carried out on bead, with 4 general steps: (1) anchor ligand synthesis, (2) acetylation, (3) click reaction, and (4) addition of 2° ligand sequence according to procedures exemplified in the preceding Example 9. In particular, triligands were synthesized by click reaction between the fully protected biligand anchor (D-Pra)-kwlwGl-Tz1-kfwlkl (0.274 g, 0.1 mmol, >98% HPLC) and bead-bound 3° ligand Az4-nlivfr (0.1 g, 0.03 mmol) using copper iodide (0.021 g, 0.1 mmol) and L-ascorbic acid (0.020 g, 0.1 mmol) in DMF/piperidine (8/2) at 25° C. overnight.

The above procedure was used for preparing Libraries D, E, and G (see Table 1 of Example 2), as well as for bulk synthesis of triligand candidates.

Example 13

Validation of Protein-Catalyzed In Situ Multi-Ligand Formation

Protein catalyzed, multi-ligand capture agents are prepared according to the scheme of FIG. 7, in which the production of a triligand capture agent is illustrated.

In particular, in the illustration of FIG. 7 a scheme for the development of a protein-catalyzed, multi-ligand capture agent is shown. It should be noted that two potential structures of the triazole linkages that bridge between the individual peptide ligands that comprise the multi-ligand are possible. Only one of the two possible structures is shown.

When an in situ multi-ligand screen is carried out according to FIG. 7; only a very small fraction of the on-bead n-order ligands are covalently coupled to the solution-phase anchor ligand by the protein. Analysis of the n-order ligands on the bead using standard methods yields information largely about the sequences of the n-order ligands themselves, since they comprise >99% of the molecules bound to the bead, and not the complete multi-ligand. For previously published in situ click chemistry screens, the triazole product was identified using chromatographic separation followed by mass spectrometry [Lewis, W. G. et al., 2002; Manetsch, R. et al., 2004; Bourne, Y. et al., 2004; Mocharla, V. P. et al., 2005; Whiting, M. et al., 2006]. For the case of the biligand screens, using in situ FIG. 7, the pairwise screen of Example 7 was adopted. This was not a broadly applicable method, but showed efficacy in one exemplary case (FIG. 28). Thus, alternative strategies are useful for demonstrating that the protein-catalyzed multi-ligand capture agent chemistry has been successful.

Two alternative strategies include: sequence homology analysis, and assays that involve amplification of one or more labeled ligands.

Sequence homology: For both the first-generation biligand and triligand screens, a striking result was the extremely high sequence homology that was observed for the hit beads. For example, for the first 17 hit beads sequenced from screen Bi1, two peptides were identical, and a third peptide varied by only a single amino acid. For screen Tri1 (against the same library), the most commonly observed amino acids by position (FIG. 32) almost exactly reflect the consensus sequence identified in the second generation (focused) screen Tri3. Such sequence homology was unique to in situ screens, and argues that these screens generate highly selective hits.

Figure 6:
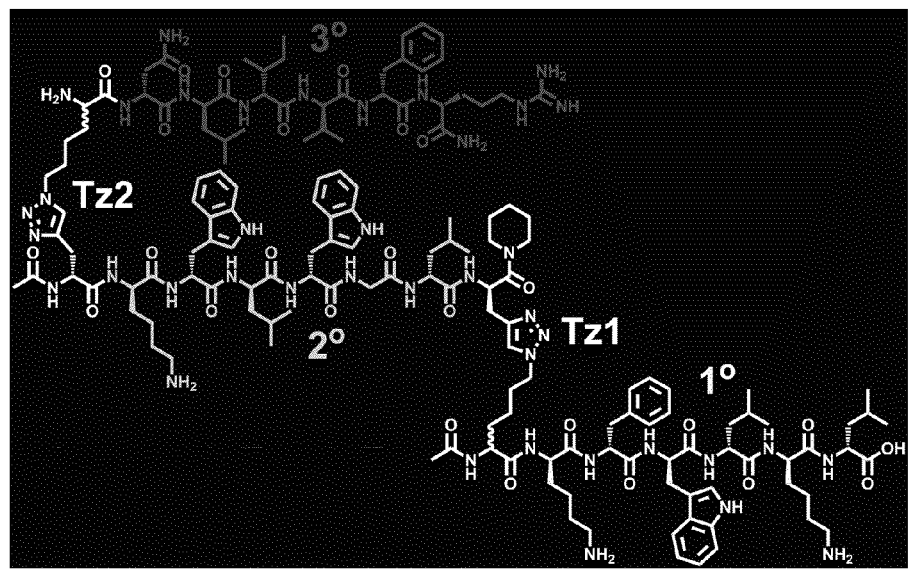
FIG. 6 shows a triligand capture agent according to an embodiment herein described. In particular, the anchor ligand is indicated by dark grey fonts, the secondary ligand by medium grey fonts, and the tertiary ligand by light grey fonts. The connections between the ligands are formed by 1,2,3-triazoles (Tz1 and Tz2).

For the case of the triligand screens, using in situ FIG. 7, a histogram charting the position-dependent frequency of amino acids observed in the hit beads was generated (FIG. 32A). Based upon that histogram, two focused OBOC libraries were constructed. The first library contained only the 3° ligand variable region, and was used in the in situ screen Tri3. The second library (Library G) contained the same 3° ligand variable region and was coupled, via CuAAC (Tz2; FIG. 6), to the biligand. Both this on-bead triligand screen Tri4, and the in situ screen Tri3, yielded the same consensus sequence. This confirmed the equivalence of the two types of screens. In addition, a third in situ screen TriX was carried out, but the $Az_n$ (azide-containing) amino acid was not included in the OBOC library, thus prohibiting the formation of a triazole linkage. That screen generated a very different, and much less homologous, set of hit sequences (FIG. 32). This result confirmed the importance of the triazole linkage in providing for a multi-ligand.

Assays with labeled ligands: an enzyme-linked, colorimetric assay was developed for detecting on-bead, protein-templated multi-ligand (FIG. 29). This approach relies upon appending a small molecule, such as biotin, to the solution-phase anchor ligand that is used in the screen. Once the screen has been completed, only the beads that contain the protein-catalyzed multi-ligand will also contain that small molecule. That molecule then provides a handle for building up a chemical construct that can generate some detectable signal. The most successful approaches will rely on signals that can be amplified. For example, if an enzyme is appended to the small molecule, and then that enzyme is utilized to catalyze some chemical process, then the chemical process itself represents an amplified signature of the on-bead protein-catalyzed multi-ligand. The product molecules produced by the enzymatic reaction can be uniquely colored, fluoresce or have some other unusual chemical or physical property that can be detected, which in turn provides evidence for the formation of the on-bead multi-ligand product. Results of such an assay, utilized to detect the on-bead formation of the triligand shown as the product of the 3° ligand screen of FIG. 7, are presented in FIG. 29.

In particular, the illustration of FIG. 29A shows the schematic of in situ click assay for on-bead triazole formation, using a biotinylated biligand anchor [Biotin-$(EG)_5$-(D-Pra)-kwlwGl-Tz1-kfwlkl]. After dissociation of the target, FIG. 29B shows that treatment with alkaline phosphatase-streptavidin (AP-SA) then BCIP (5-bromo-4-chloro-3-indoyl phosphate; following Liu, G. and K. S. Lam, 2000) yields purple beads (shown in dark grey) as a positive indicator of multi-ligand formation. In situ triligand was only formed in the presence of b(h)CAII protein, and not when the protein was human transferrin (Tf), BSA, or absent. Also, triligand is not observed when the biligand anchor sequence is incorrect.

PCR Assay for the detection and quantitation of the formation of on-bead, protein-catalyzed multi-ligand protein capture agent. This assay is shown in FIG. 21. The PCR-based assay is a variation of the enzymatic assay where AP-SA is replaced with streptavidin conjugated to a small template oligonucleotide (5' . . . $NH_2$—$(CH_2)_6$-GGGACAATTAC-TATTTACAATTACAATGCTCACGTGG-TACGAGTTCGTCTCCCAGG . . . 3'-SEQ ID NO: 1). Binding of this reagent to biotinylated triligand results in the recruitment of the template oligonucleotide to the bead surface where it can be amplified by PCR. The extent of amplification is directly proportional to the amount of oligonucleotide at the bead surface, providing a quantitative read-out of the assembled triligand.

The streptavidin oligo reagent was prepared as described below: SAC expression was performed according to previously published protocols (Sano, T. and C. R. Cantor, 1990).

Prior to use, stock SAC (streptavidin-cysteine) was buffer exchanged to Tris buffered Saline (TBS) containing 5 mM Tris(2-Carboxyethyl) phosphine Hydrochloride (TCEP) using desalting columns (Pierce). MHPH (3-N-Maleimido-6-hydraziniumpyridine hydrochloride, Solulink) in DMF was added to SAC at a molar excess of 300:1. In parallel, SFB in DMF (succinimidyl 4-formylbenzoate, Solulink) was added in a 40:1 molar excess to the 5'aminated oligo. The mixtures were allowed to react at room temperature for 3-4 hours. Excess MHPH and SFB were removed and samples were buffer exchanged to citrate buffer (50mM sodium citrate, 150 mM NaCl, pH 6.0) using zeba desalting spin columns (Pierce). The SFB-labeled oligo was then combined in a 20:1 molar excess with the derivatized SAC and allowed to react for 2-3 hours at room temperature before transferring to overnight incubation at 4° C. Unreacted oligos were removed using a Pharmacia Superdex 200 gel filtration column at 0.5 ml/min isocratic flow of PBS. Fractions containing the SAC-oligo conjugates were concentrated using 10K mwco concentration filters (Millipore). The synthesis of SAC-oligo constructs was verified by non-reducing 8% Tris-HCl SDS-PAGE.

The triligand-containing beads were prepared as described above (see FIG. 29A). After dissociation of the target, 0.5 mg beads were washed 10 times in water and resuspended in blocking buffer (0.15% BSA (w/v), 0.1% Tween-20, 150 μg/mL sheared salmon sperm DNA, in PBS pH 7.4). The beads were washed 3 times in 100 μL blocking buffer and incubated for 1 h at 25° C. in 100 μL blocking buffer. The beads were then filtered and washed twice more in 100 μL blocking buffer. 100 μL of Streptavidin-oligo (170 ng/mL in blocking buffer) was added and the beads were incubated for 1 h at 25° C. The beads were washed 5 times in 250 μL blocking buffer followed by three washes in 250 μL PBS. The beads were resuspended in dH$_2$O and spotted on a glass slide.

After evaporation, the beads were manually picked and placed in thin-walled PCR tubes.

Quantitative PCR (QPCR) was carried out on a Bio-Rad Real Time PCR system. To each tube containing 1-5 individual beads was added 12.5 μL iQ SYBR Green Supermix (Bio-Rad), 11.5 μL dH$_2$O, 100 nM Forward Primer (5' . . . TAATACGACTCACTATAGGGACAATTAC-TATTTACAATTACA . . . 3'-SEQ ID NO: 2), and 100 nM Reverse Primer (5' . . . ACCGCTGCCAGACCCCGATTTG-GCCTGGGAGACGAACTCG . . . 3' SEQ ID NO: 3). Real time PCR was carried out for 30 cycles with the following thermal profile: 94° C., 30 sec, 50° C., 45 sec., 72° C., 60 sec. A standard curve was generated using known template concentrations ranging from 0.01 nM to 0.01 pM. The Ct values for each of the known concentrations were plotted against the log of the template concentration to generate a linear standard curve which was then used to determine the concentration of oligo in each of the sample tubes. This was adjusted based on the number of oligonucleotide templates present per streptavidin tetramer as estimated by SDS-PAGE.

Example 14

Affinity Measurements for Triligands

Figure 33:
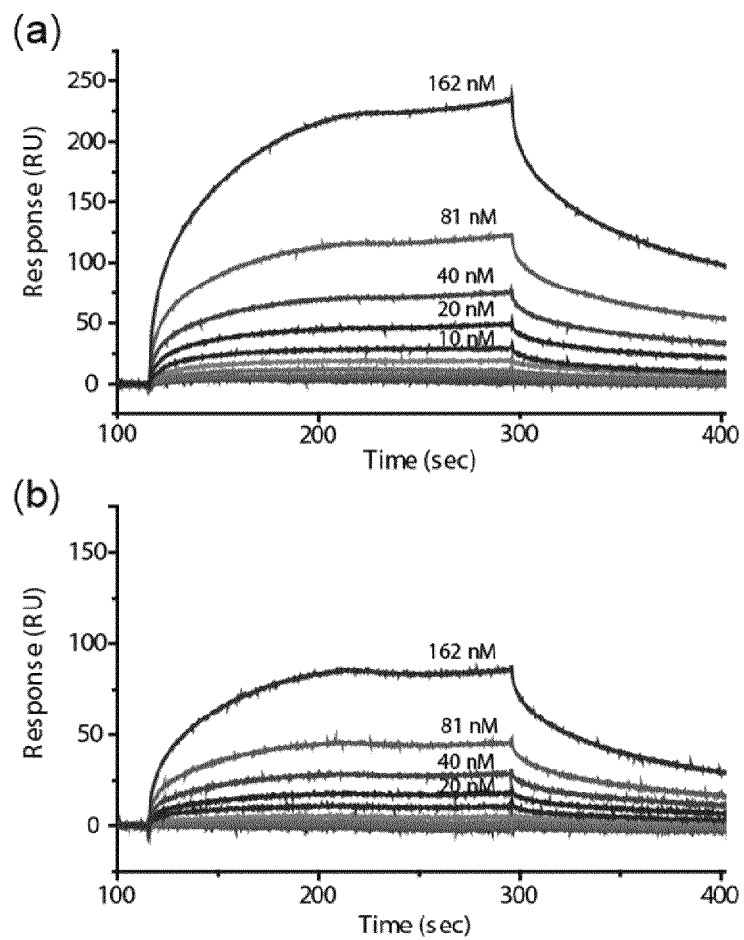
FIG. 33 shows diagrams illustrating variation of detected binding affinity for a multi-ligand capture agent with increasing concentration of the multi-ligand capture agent according to an embodiment herein described. In particular, Panels A and B show SPR response sensorgrams for the triligand capture agent of FIG. 15 (rfviln-Tz2-kwlwGl-Tz1-kfwlkl) obtained with increasing peptide concentration (0.1 nM to 162 nM) measured for human (A) and bovine (B) CAII targets, respectively.

Binding affinity measurements describing the specific interaction between triligand capture agent and b(h)CAII were performed using the methods exemplified in Example 10. Response data were then collected for triligand (FIG. 33) analytes over varying concentrations at a 100 μL/min flow rate, 120-180 s contact time, and 300 s dissociation phase across the four flow cells. Following background subtraction, the analyte response data was fitted for 1:1 binding affinity using the BiaEvaluation software. In FIG. 33, representative results are shown (FIG. 33A and FIG. 33B).

In particular, the illustration of FIG. 33A shows SPR response sensorgrams obtained with increasing concentration of the triligand rfviln-Tz2-kwlwGl-Tzl-kfwlkl (0.1 nM to 162 nM), and demonstrate 45-nM and 64-nM affinities for human (FIG. 33A) and bovine (FIG. 33B) CA II, respectively. These equilibrium dissociation constants represent a 50-fold affinity enhancement compared to the interaction between biligand and target (see also FIG. 28).

Example 15

Enzyme Activity Assay in the Presence of Triligand

Enzymatic activity of bCAII on the substrate 4-nitrophenyl acetate (4-NPA; Pocker, Y. and J. T. Stone, 1967) was measured in presence and in absence of a triligand capture agent as well as in absence of bCAII as a control. The esterase activity over time is unchanged when the triligand capture agent is present in the assay.

Figure 34:
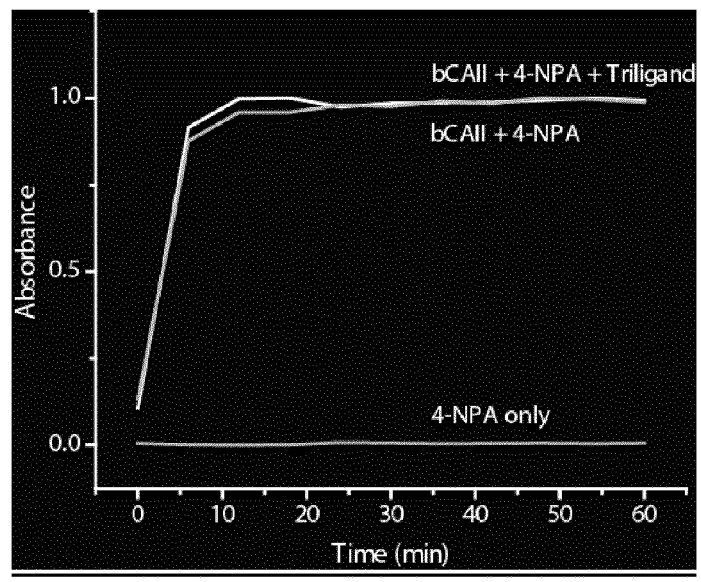
FIG. 34 shows a diagram illustrating enzymatic activity of a target molecule in a complex with a multi-ligand capture agent according to an embodiment herein described. In particular, the diagram of FIG. 34 shows enzymatic activity of bCAII on the substrate 4-nitrophenyl acetate (4-NPA) in presence (grey) and in absence (black) of a triligand capture agent as well as in absence of bCAII (dark grey) as a control. The activity over time is unchanged when the triligand capture agent is present in the assay.

The experimental results are presented in FIG. 34. It was observed that the triligand did not interfere with the enzyme activity of bCAII, apparently binding away from, or at least not interfering with, the normal catalysis of the active site. Such off-site, yet highly selective binding is common for natural antibodies raised against proteins, and bodes well for the scope of the technique at hand.

Example 16

Dot Blot Selectivity/Sensitivity Assays in Serum

Dot blots are a common method for detecting proteins. The sensitivity and selectivity of the multi-ligand (biligand and triligand) capture agents for b(h)CAII in complex environments were demonstrated through the use of dot blot experiments in 10% porcine serum. For a dot blot, the solution containing the protein of interest is simply dotted onto an absorbent membrane material (typically nitrocellulose). The capture agent (typically an antibody) is labeled with biotin molecule, and applied to the same spot. The spot is rinsed, and then horseradish peroxidase (HRP)-labeled streptavidin is added, binding to the biotin that is bound to the protein. Optical methods are typically utilized to detect this binding.

For these tests, Biotin-PEG-NovaTag resin (0.48 mmol/g; Novabiochem) was utilized for bulk synthesis of C-terminal biotin-labeled multi-ligands. After resin cleavage, the crude biotinylated multi-ligand was precipitated with ether and then purified to >98% by C$_{18}$ reversed phase HPLC.

For a dot blot assay, the procedure was as follows: b(h)CAII antigens were prepared as 1 mg/mL stocks in PBS (pH 7.4). A dilution series of antigen was applied to a nitrocellulose membrane, typically ranging from 2 μg to 0.5 ng per spot. The membrane was blocked at 4° C. overnight in 5% milk in Tris-buffered saline (TBS) [25 mM Tris, 150 mM NaCl, 2 mM KCl (pH 8.0)]. The membrane was then washed with TBS. The biotinylated multi-ligand was prepared at 1 μM in 10% porcine serum in TBS+0.1% DMSO and incubated over the membrane overnight at 4° C. After washing with TBS for 1 h, 1:3000 Streptavidin-HRP (Abcam, Cambridge, Mass.) prepared in 0.5% milk/TBS was added to the membrane and incubated for 1 h. After washing with TBS for 1 h, the membrane was treated to chemiluminescent reagents (SuperSignal West Pico Chemiluminescent Enhancer and Substrate Solutions, Pierce, Rockford, Ill.) and then immediately developed on film.

Results for the dot blot assay to use the biligand (FIG. 14) and the triligand (FIG. 15) to detect hCAII and bCAII from porcine serum are shown in FIG. 21. It is noted that bCAII and hCAII are >80% identical by sequence (PDB ID: 1CA2, 1V9E).

In particular, FIG. 21A shows a dot blot illustrating the limit of detection by the triligand for b(h)CAII in 10% porcine serum. This detection limit is 20 ng protein. FIG. 21B shows that when the biligand anchor (D-Pra)-kwlwGl-Tz1-kfwlkl is used as the capture agent in 0.1% serum, the sensitivity is reduced >10-fold.

Example 17

Branched Multi-Ligand Capture Agents

Linear polypeptide chains may adopt folded structures, thus displaying a number of possible tertiary interactions with the potential protein target. A branched oligopeptide can emulate such folded structures, but with the major advantage that it has a much smaller footprint (and is thus much cheaper to make). Branched multi-ligand capture agents, as prepared by methods illustrated in FIG. 8 can also exhibit a host of desired chemical, physical, and biochemical properties—namely, stability in various environments in which antibodies and natural polypeptides are not stable.

Figure 17:
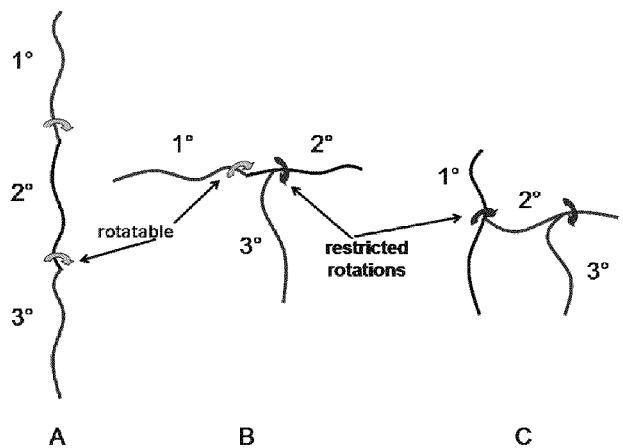
FIG. 17 shows a schematic illustration of branched multi-ligand capture agents according to an embodiment herein described. Panel A shows a linear triligand capture agent. Panels B and C show branched triligand capture agents, highlighting the bonds with restricted rotations in such structures. The bonds with restricted rotations of Panels B and C have the potential to increase avidity relative to a similarly developed, but linear, multi-ligand capture agent (Panel A).
Figure 18:
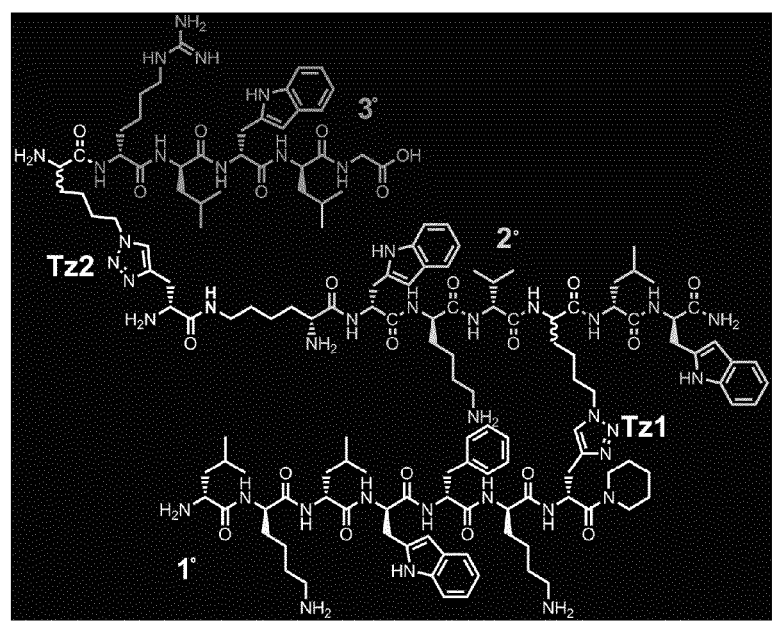
FIG. 18 shows the structure of a branched triligand capture agent according to several embodiments herein described. The anchor ligand is denoted as 1°, the secondary ligand as 2°, the tertiary ligand as 3° and the two 1,2,3-triazole linker (connecting 1° and 2° and 2° with 3°) as Tz1 and Tz2 respectively.

Of relevance to improving capture agent avidity with low molecular weight peptides are the comparative binding kinetics and thermodynamics of branched and linear multi-ligand capture agents. FIG. 17 schematically illustrates this effect.

In particular, the illustration of FIG. 17 schematically compares linear to branched triligand capture agents. FIG. 17A shows a linear triligand capture agent, which is a single peptide chain. FIG. 17B (one branchpoint) and FIG. 17C (two branchpoints) show representative structures of branched triligand capture agents. The branchpoints in the branched multi-ligands impart different conformational dynamics, as compared with the linear multi-ligand and within classes of branched capture agents. The restricted rotations around these bonds in the branched multi-ligand structures have the potential to increase avidity relative to a similarly developed but linear multi-ligand capture agent.

A branched multi-ligand capture agent has been developed against the b(h)CAII protein, using the method exemplified in FIG. 8. As in the linear case (FIG. 7), the anchor ligand lklwfk-(D-Pra) was utilized in a two-generation in situ biligand screen. The first-generation screen BrBi1 identified a position within the library of secondary) (2°) ligands (Library H) tolerant of branching. In the screen BrBi1, a solution of 50 nM bCAII-Alexa647 was pre-incubated with peptide anchor ligand (lklwfk-(D-Pra), 2000×relative to protein) for 2 h at 37° C. in PBS (pH 7.4)+0.1% Tween20+0.1% BSA+0.05% NaN$_3$+1% DMSO (v/v). The anchor ligand/protein solution was added to Library H and incubated for 18 h at 37° C., with shaking. The screened beads were washed with 6×5 mL PBS (pH 7.4)+0.1% Tween20+0.1% BSA+0.05% NaN$_3$, 2×5 mL PBS (pH 7.4)+0.1% Tween20, and 4×5 mL PBS. The beads were imaged for fluorescence using the protocol outlined in Example 3. Hits (representing in situ biligands) were picked by micropipette, processed with 7.5 M guanidine hydrochloride (pH 2.0) to remove bound protein, and then analyzed by Edman degradation to decode the secondary ligand sequences.

The results of screen BrBi1 are shown in Table 3. The high conservation of Az4 as the 4th residue in selected secondary ligands indicates that our method of FIG. 8 is successful for selecting branchpoints.

TABLE 3

| $x_1$ | $x_2$ | $x_3$ | $x_4$ | $x_5$ | $x_6$ |
|---|---|---|---|---|---|
| i | k | f | Az4 | v | w |
| i | k | v | Az4 | i | w |
| f | k | w | Az4 | i | w |
| f | k | w | Az4 | i | w |
| v | k | v | Az4 | i | w |
| w | k | v | Az4 | i | w |
| w | k | i | Az4 | i | w |
| f | k | l | f | i | k |
| f | k | l | w | i | k |
| i | f | i | k | i | k |
| i | v | k | w | k | k |
| f | k | f | Az4 | f | f |
| Az4 | k | w | G | G | l |
| Az4 | k | f | Az4 | i | w |

The second-generation screen BrBi2 using a focused library of secondary) (2°) ligands (Library I) identified vkw (Az4)fw and wkv(Az4)lw as two optimized secondary ligand candidates. In the screen BrBi2, solutions ranging from 10 nM to 500 pM bCAII-Alexa647 were pre-incubated with peptide anchor ligand (lklwfk-(D-Pra), 40 µM) for 2 h at 25° C. in PBS (pH 7.4)+0.1% Tween20+0.1% BSA+0.05% NaN$_3$+1% DMSO (v/v). The anchor ligand/protein solution was added to Library I and incubated for 15 h at 25° C., with shaking. The screened beads were washed, imaged for fluorescence, and picked using the protocol outlined in Example 3. After treatment with 7.5 M guanidine hydrochloride (pH 2.0) to remove bound protein, analysis by Edman degradation yielded a list of optimized secondary ligand sequences which were subjected to histogram analysis as described in Example 7. Histogram analysis illustrated that all hits from screen BrBi2 contained a single consensus sequence, $x_1$-k-$x_3$-Az4-$x_5$-w. Two branched biligand capture agent candidates, vkw (Tz1)fw-kfwlkl and wkv(Tz1)lw-kfwlkl (the former shown by molecular structure in FIG. 16A), appeared predominant in that they were observed twice during the same screen and were isolated as the only hits at the lowest protein concentrations tested (i.e., ≤1 nM target).

Branched biligand synthesis using on-bead click reaction. Branched biligand synthesis was performed as shown in Scheme 4 by modification of the linear biligand synthesis (Scheme 2 of Example 9). First, the secondary (2°) ligand was synthesized on Fmoc-Rink amide MBHA resin (0.67 mmol/g) using N$^\alpha$-Fmoc protection strategy. The terminal amino acid (e.g., D-Val as shown in Scheme 4) was installed as the N$^\alpha$-Boc protected version, which capped further synthesis on this segment. Next, the Fmoc-D-Pra-OH (0.15 mmol) was covalently linked to the bead-bound secondary ligand (0.03 mmol) by CuAAC using copper iodide (0.15 mmol) and L-ascorbic acid (0.15 mmol) in DMF/piperidine (8/2) at 25° C. overnight. To this branchpoint, which reveals a terminal amine for further peptide synthesis, the remaining portion of the anchor ligand sequence (lklwfk) was coupled through standard N$^\alpha$-Fmoc protection strategy. After treatment with 95:5 TFA:triethylsilane (TES) scavenger, this branched biligand was purified by HPLC to >95%.

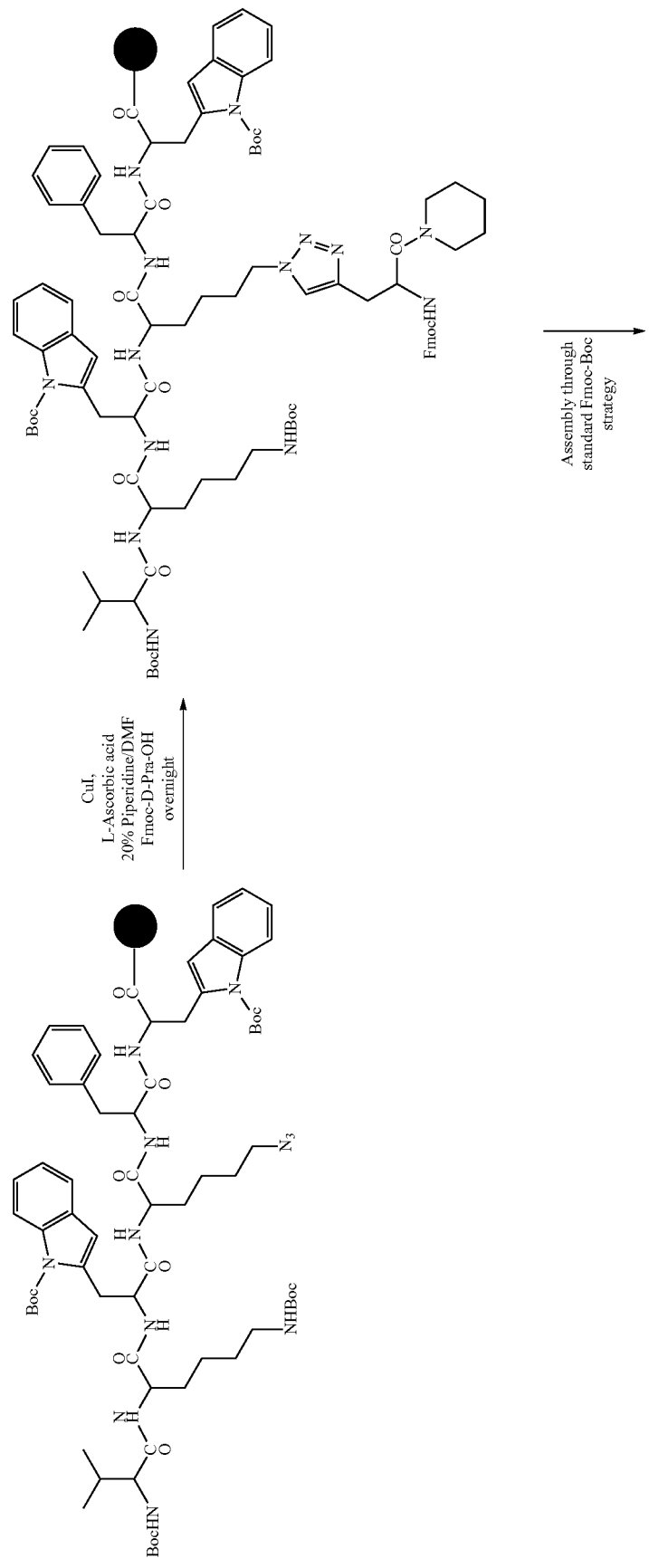

-continued
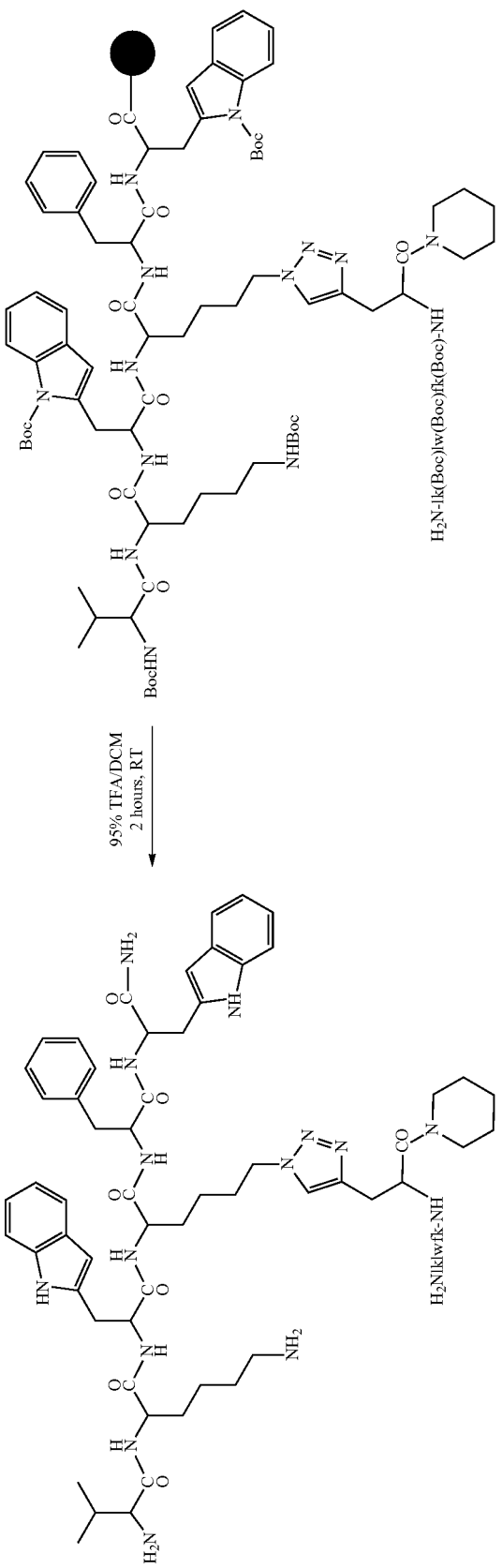
95% TFA/DCM
2 hours, RT

FIG. 16A shows the chemical structure of a branched biligand capture agent vkw(Tz1)fw-kfwlkl for bCAII. Binding affinity measurements describing the specific interaction between branched biligand capture agent and bCAII were performed using the SPR methods detailed in Example 10. FIG. 16B shows SPR response sensorgrams obtained with increasing concentration of the biligand (0 to 1656 nM), demonstrating a 500 nM biligand affinity to bCAII. When compared to the binding affinity for the similarly developed linear biligand capture agent (see also FIG. 28), the affinity of this branched entity is better by a factor of 5. A branched triligand accordingly can adhere to this same affinity enhancement and should display pM affinity.

Utilization of a Branched Biligand as an Anchor Ligand for Longer Branched Multi-Ligand Capture Agent.

Once a branched biligand is identified, that branched biligand can serve as the FIG. 8 anchor ligand, and a branched triligand can be selected in a tertiary (3°) screen. The third-generation screen BrBi3 using an even more focused library of secondary (2°) ligands (Library J) identified that D-Lys is a suitable amino acid for installing a new branchpoint at a position $x_0$. In the screen BrBi3, a solution of 10 nM bCAII-Alexa647 was pre-incubated with peptide anchor ligand (lkl-wfk-(D-Pra), 40 µM) for 2 h at 25° C. in PBS (pH 7.4)+0.1% Tween20+0.1% BSA+0.05% $NaN_3$+1% DMSO (v/v). The anchor ligand/protein solution was added to Library J and incubated for 15 h at 25° C., with shaking. The screened beads were washed, imaged for fluorescence, and picked using the protocol outlined in Example 3. After treatment with 7.5 M guanidine hydrochloride (pH 2.0) to remove bound protein, analysis by Edman degradation yielded the sequences shown in Table 4. Analysis of Table 4 led to the decision that kwkv(Az4)lw, with a second branchpoint installed at $x_0$, was suitable for building a branched biligand anchor.

TABLE 4

| $x_0$ | $x_1$ | $X_2$ | $x_3$ | $x_4$ | $x_5$ | $x_6$ |
|---|---|---|---|---|---|---|
| k | w | K | w | Az4 | l | w |
| r | v | K | w | Az4 | i | w |

TABLE 4-continued

| $x_0$ | $x_1$ | $X_2$ | $x_3$ | $x_4$ | $x_5$ | $x_6$ |
|---|---|---|---|---|---|---|
| v | w | K | v | Az4 | i | w |
| k | w | K | v | Az4 | l | w |
| a | v | K | v | Az4 | l | w |
| i | v | K | w | Az4 | l | w |
| i | w | K | v | Az4 | f | w |

The method of the BrBi3 screen can be repeated using the triligand, tetraligand, etc. for the identification of new branch-point positions in n-order anchors for selecting n-order branched multi-ligand capture agents.

Branched biligand anchor synthesis was performed as shown in Scheme 5 by slight modification of Scheme 4. First, the secondary (2°) ligand was synthesized on Fmoc-Rink amide MBHA resin (0.67 mmol/g) using standard $N^\alpha$-Fmoc protection strategy. The N-terminal position of this secondary (2°) ligand was synthesized to present the second branchpoint via incorporation of D-Lys(ivDde) (ivDde=1-(4,4-dimethyl-2,6-dioxocyclohex-1-ylidene)-3-methylbutyl), which allowed for selective deprotection and reaction with the D-Lys side chain at a later stage. Note that D-Lys was an $x_0$ residue selected by screen BrBi3. After this D-Lys(ivDde) coupling and capping with acetic anhydride (see Example 9), the modified secondary ligand Ac-k(ivDde)wkv(Az4)lw resulted. Next, the Fmoc-D-Pra-OH (0.15 mmol) was covalently linked to the bead-bound modified secondary ligand (0.03 mmol) by CuAAC using copper iodide (0.15 mmol) and L-ascorbic acid (0.15 mmol) in DMF/piperidine (8/2) at 25° C. overnight. To this branchpoint, which reveals a terminal amine for further peptide synthesis, the remaining portion of the anchor ligand sequence (lklwfk) was coupled through standard $N^\alpha$-Fmoc protection strategy. Finally, selective removal of the ivDde protecting group by treatment with 2% hydrazine in DMF reveals a primary amine to which Fmoc-D-Pra-OH is coupled by standard amide coupling chemistry.

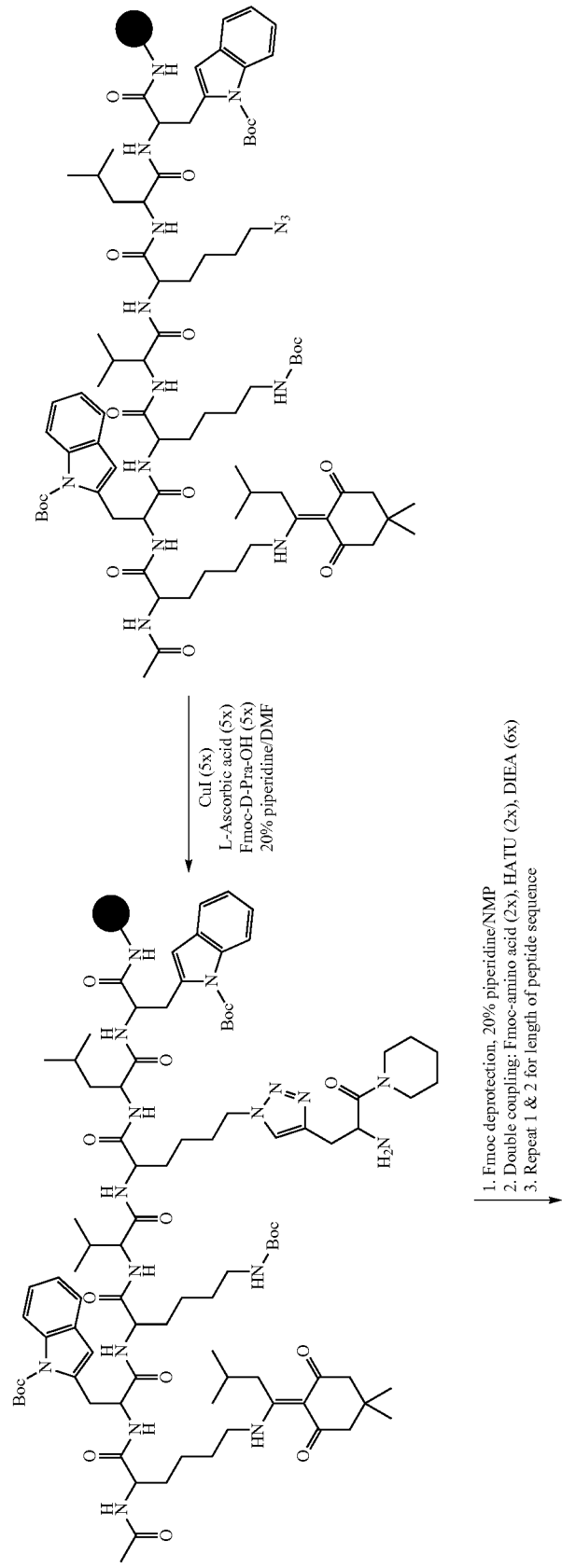
SCHEME 5

-continued
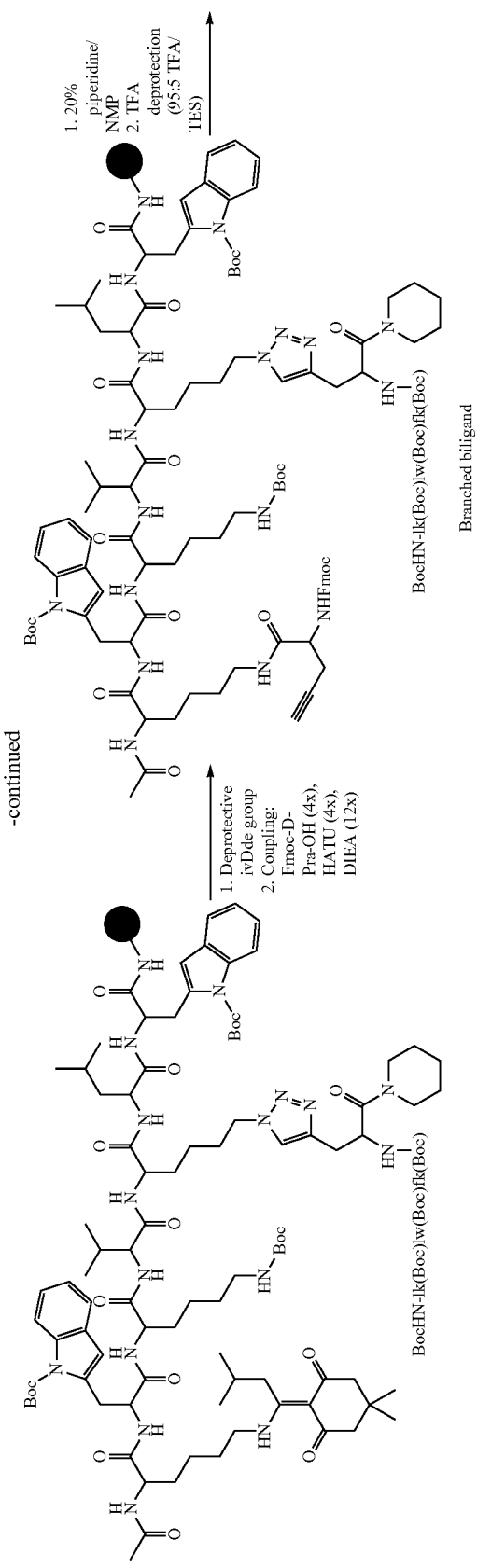
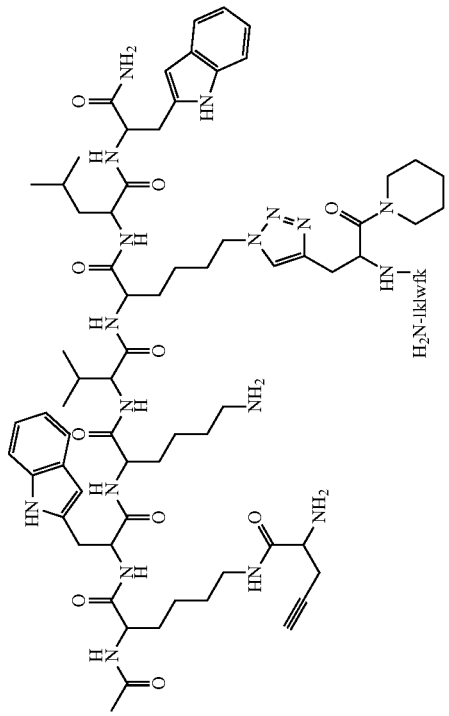

Identification of a branched triligand capture agent. With the branched biligand anchor (D-Pra)-kwkv(Tz1)lw-kfwlkl of Scheme 5, A tertiary (3°) screen was performed against bCAII and Library C following the method depicted in FIG. 8 to identify a branched triligand capture agent. In the screen BrTri1, a solution of 50 nM bCAII-Alexa647 was pre-incubated with 100 μM branched biligand anchor for 2 h at 25° C. in PBS (pH 7.4)+0.1% Tween20+0.1% BSA+0.05% NaN3+ 1% DMSO (v/v).

The anchor ligand/protein solution was added to Library C and incubated for 16 h at 25° C., with shaking. The screened beads were washed, imaged for fluorescence, and picked using the protocol of Example 3. After treatment with 7.5 M guanidine hydrochloride (pH 2.0) to remove bound protein, analysis by Edman degradation yielded the tertiary) (3°) ligand sequences. Histogram analysis of the tertiary ligand sequences, following the methods of Example 11, yielded branched triligand capture agents, like the one shown schematically in FIG. 17B and by molecular structure in FIG. 18.

Example 18

Methods for Synthesizing a Multi-Ligand Capture Agent

Figure 35:
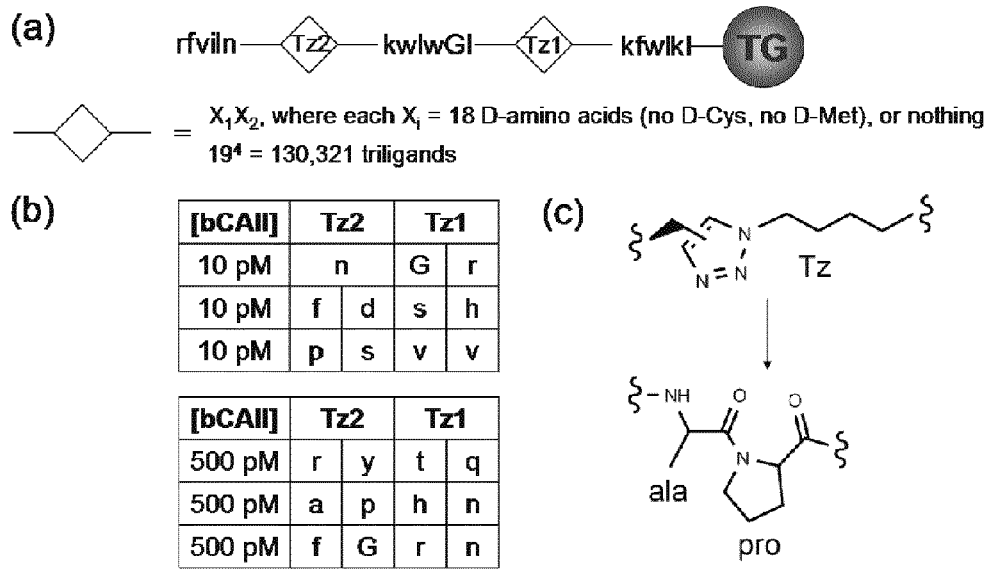
FIG. 35 shows a schematic illustration of a method to identify suitable linkers connecting the ligands of a multi-ligand capture agent according to an embodiment here described. Panel A shows a schematic illustration of a formulation of a library utilized for screening alternate linkers to replace the 1,2,3-triazole linkers (Tz1 and Tz2) in the triligand capture agent against b(h)CAII. Panel B shows representative hits, indicating D-amino acids that would be suitable replacements for Tz1 or Tz2. Panel C shows an illustration of the compatibility of the alternate amide linkers representing a more compact version of the original 1,2,3-triazole.

Functional groups, such as azide and acetylene (FIG. 2), enable the protein-catalyzed assembly of multi-ligand capture agents as exemplified in Example 5 and Example 17. Functional groups are merely screening tools, and are not necessarily desired in the capture agents implemented in diagnostics assays, separations, and the like. A procedure for synthesizing multi-ligand capture agents in bulk quantities for such assays involves the replacement of the azide-alkyne 1,2,3-triazole linker by a 2-amino acid linker (see FIG. 35). This alternate linker allows for high-throughput production of the capture agent with no modification to current automated peptide synthesis instrumentation. FIG. 35A shows the formulation of one OBOC library utilized for screening alternate linkers to replace the 1,2,3-triazole linkers (Tz1 and Tz2) in the triligand capture agent against bCAII. Screens were conducted using this library following Example 3 above.

Figure 36:
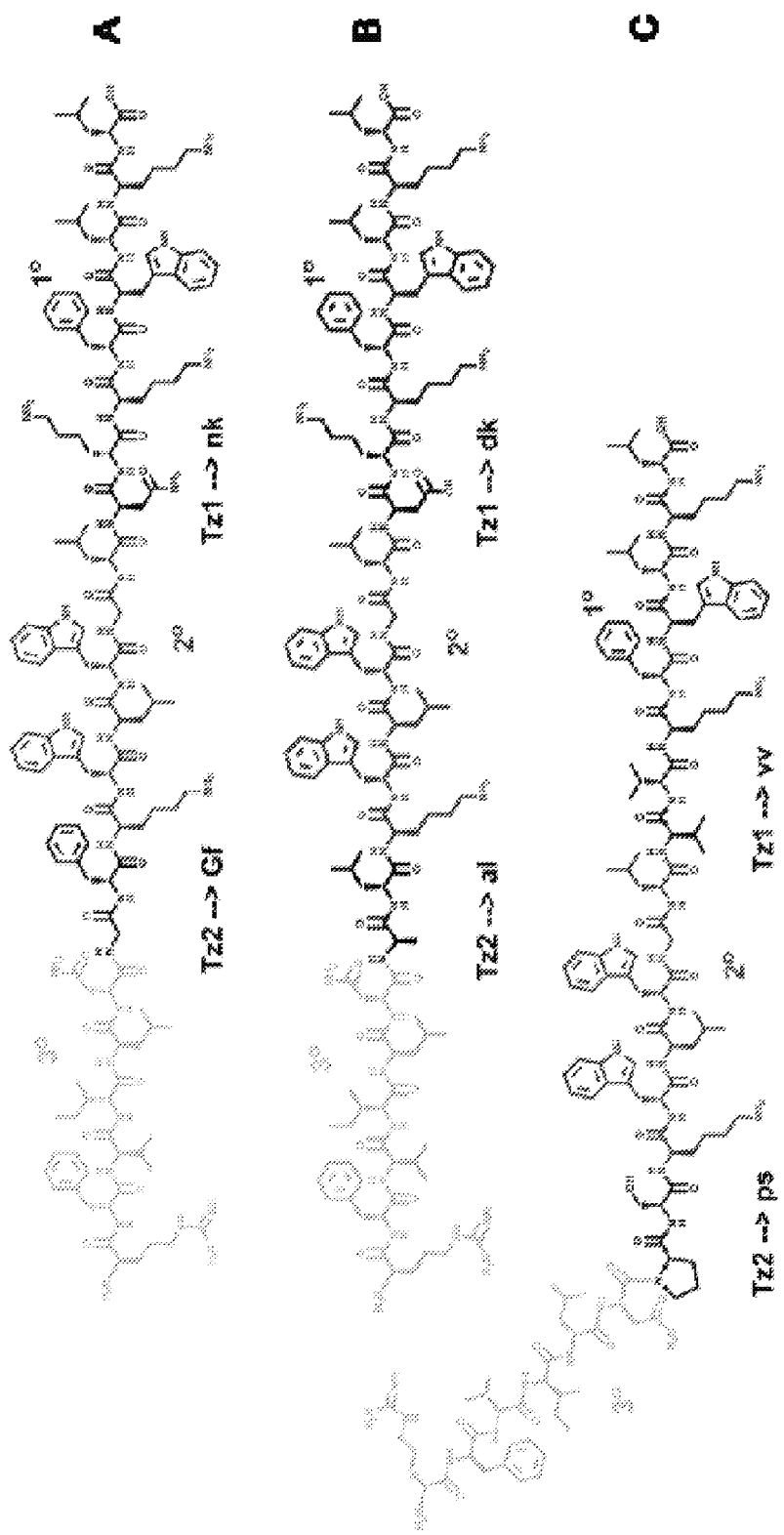
FIG. 36 shows the molecular structures of three triligand capture agents presenting amide linkers instead of the 1,2,3-triazole linkers (Tz1 and Tz2): Panel A, denoted TzR1, where Tz2=Gf, and Tz1=nk; Panel B, denoted TzR3, where Tz2=al, and Tz1=dk; and Panel C, denoted TzR2, where Tz2=ps, and Tz1=vv.

FIG. 35B shows representative hits, indicating which D-amino acids would be suitable replacements for Tz1 or Tz2. The molecular structures of several of these hits is shown in FIG. 36: FIG. 36A denoted TzR1, where Tz2=Gf, and Tz1=nk; FIG. 36B, denoted TzR3, where Tz2=al, and Tz1=dk; and FIG. 36C, denoted TzR2, where Tz2=ps, and Tz1=vv.

Note that the new surrogate for the 1,2,3-triazole itself is one backbone amide bond, as shown in FIG. 37C (reproduced from Bock, V. D. et al., 2006). The amide bond functions as a rigid linking unit that can mimic the atom placement and electronic properties of the 1,2,3-triazole (Kolb, H. C. and K. B. Sharpless, 2003; Bock, V. D. et al., 2006). The Tz1 and Tz2 linkers represent the covalent synthesis of the 1,2,3-triazole between azidobutyl and propargyl side chain groups (see FIG. 6), however, and so two to five amide bonds can ideally mimic the atom placement and electronic properties of an entire linker. FIG. 35C shows an illustration that the chosen amide linkers can be more compact than the original Tz1 and Tz2 linkers. One can exploit amide linker mimics as a means for tuning the properties of the capture agent for the protein assays (e.g., western blots, dot blots, and ELISA-like assays) described in this Examples 16, 20, and 21.

Figure 37:
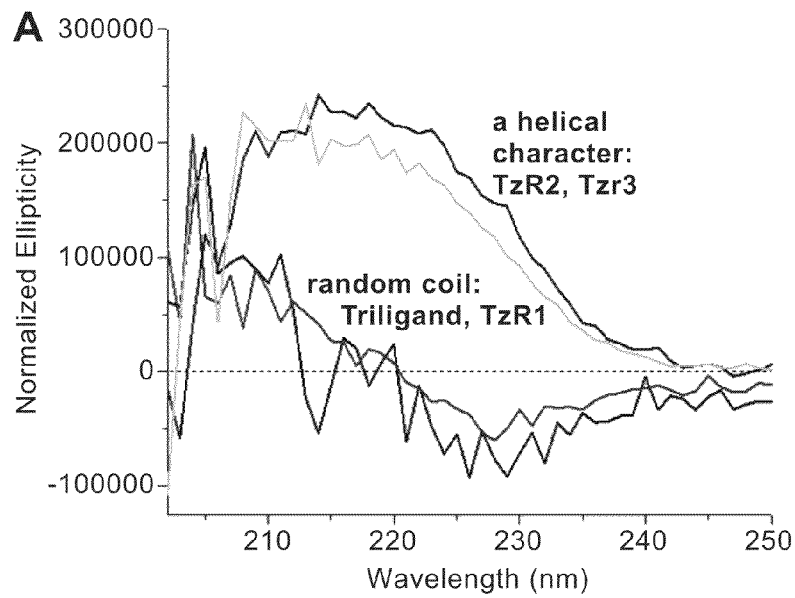
FIG. 37 describes properties of triligand capture agents whose connecting linker between ligands has been replaced by one or more amide bonds. Panel A shows results of circular dichroism (CD) experiments, illustrating that triligand capture agent TzR1 shares similar structure with original triligand sequence (rfviln-Tz2-kwlwGl-Tz1-kfwlkl, FIG. 6) in that they are both random coils. Panel B shows results of the binding interaction between TzR1 (0 to 1500 nM analyte) and b(h)CAII by SPR, where an equilibrium dissociation constant was estimated as high nM. Panel C illustrates that the atom placement and electronic properties of a 1,2,3-triazole may be mimicked by an amide bond.
Figure 37:
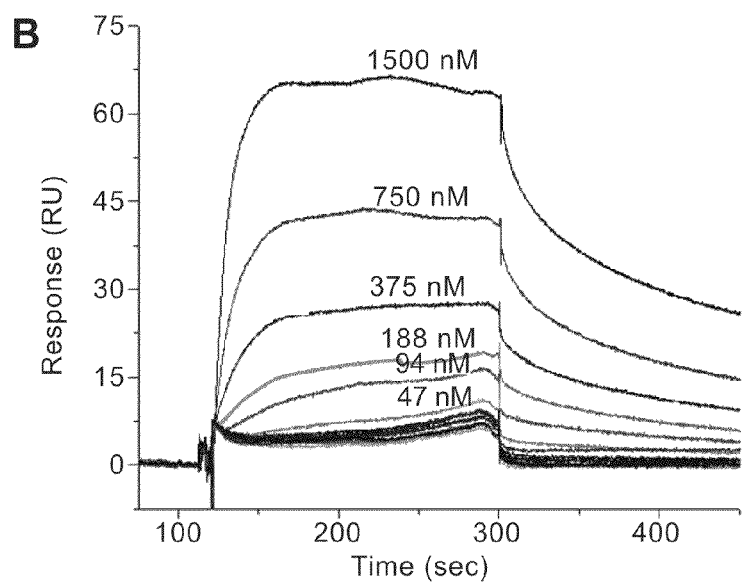
Figure 37:
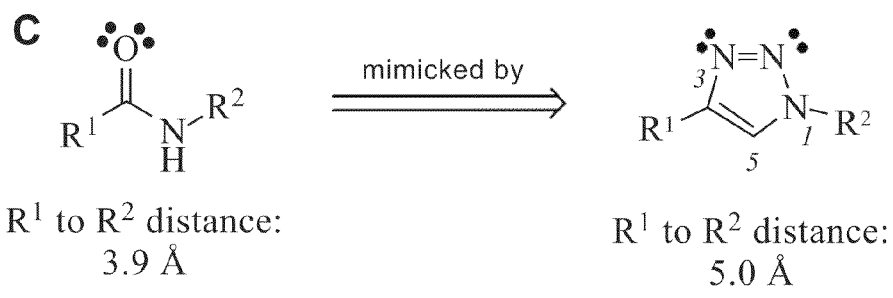

Properties of triligand capture agents with surrogate amide linkages are illustrated in FIG. 37. By circular dichroism (CD) experiments, triligand capture agent TzR1 was found to share similar structure with original triligand sequence (rfviln-Tz2-kwlwGl-Tz1-kfwlkl, FIG. 6); they are both random coils (FIG. 37A). In contrast, TzR2 and TzR3 were ruled out as suitable candidates based on their strong α-helical character, which is unlike the triligand of FIG. 6. When the binding interaction between TzR1 and b(h)CAII was measured by SPR, an equilibrium dissociation constant was estimated as high nM (FIG. 33B). a second-generation screen of triligands with surrogate amide linkages, focusing on random coil structures and longer 3- to 5-amino acid linker lengths can yield a surrogate triligand whose $K_D$ is 45-64 nM or better than the original triligand.

Figure 38:
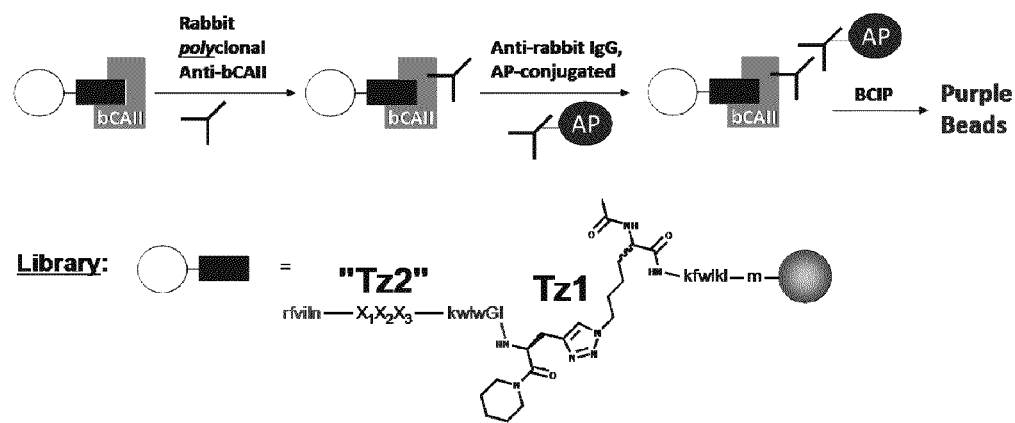
FIG. 38 shows an example of a screening approach for identification of a 3-amino acid linker to replace the Tz2 linker in the triligand capture agent of FIG. 6. It is noted that this screening approach is similar to the ELISA-like sandwich assay of FIG. 23 but with the substrate being a bead rather than a microwell.

An example of a screening approach for identification of a 3-amino acid linker to replace the Tz2 linker is shown in FIG. 38. It is noted that this screening approach is an ELISA-like sandwich assay (see Example 21) but with the substrate being a bead rather than a microwell. In this approach, a comprehensive library of 3-amino acid linkers ($X_i$=any D-stereoisomer, except D-Met and D-Cys), totaling 5832 sequences, is first blocked overnight at 25° C. in Blocking Buffer (25 mM Tris-Cl, 10 mM $MgCl_2$, 150 mM NaCl, 14 mM 2-mercaptoethanol, 0.1% (w/v) BSA, 0.1% (v/v) Tween 20, pH 7.5)). After blocking, the comprehensive library is contacted with the target (e.g., 10 nM to 1 μM bCAII). After contact for 1 h at 25° C., the library/target complex is washed with 5×1 mL Blocking Buffer to remove excess target and then incubated with a primary antibody (e.g., rabbit polyclonal anti-bCAII at 1:5000 dilution) for 1 h. Beads were washed with Blocking Buffer to remove excess primary antibody, and then incubated with a secondary antibody (e.g., anti-rabbit IgG, alkaline phosphatase (AP)-conjugated, at 1:2000 dilution) in Blocking Buffer for 30 min with shaking. Excess secondary antibody was removed by washing the beads with 5×1 mL Wash 1 Buffer (25 mM Tris-Cl, 10 mM $MgCl_2$, 700mM NaCl, 14 mM 2-mercaptoethanol, pH 7.5), followed by 5×1 mL Wash 2 Buffer (25 mM Tris-Cl, 14 mM 2-mercaptoethanol, pH 7.5). Beads were developed for 20 min in the chromogenic substrate BCIP. The darkest purple beads were selected as hits, washed with guanidine hydrochloride (pH 2.0) to remove bound protein, and then sequenced by Edman degradation as described in Example 3 to identify $X_1$, $X_2$, and $X_3$.

Example 19

Biligand and Triligand Capture Agents—Structural Considerations

Figure 5:
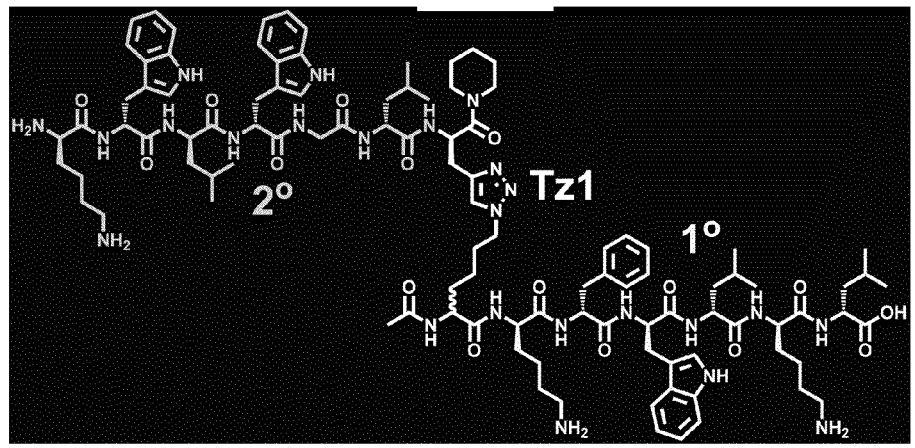
FIG. 5 shows a biligand capture agent according to an embodiment herein described. In particular, a biligand capture agent composed of 14 non-natural and artificial amino acids can be synthesized with high purity (displaying a single parent mass). The anchor ligand is denoted as 1°, the secondary ligand as 2°, and the 1,2,3-triazole linker (connecting 1° and 2°) as Tz1.

Structures of a protein-catalyzed biligand capture agent and a protein-catalyzed triligand capture agent are shown in FIG. 5 and FIG. 6 respectively. These capture agents were made according to the methods of Examples 4-12.

The capture agents shown in FIG. 5 and FIG. 6 were assembled sequentially, starting with a 1° peptide ligand that was comprised of non-natural amino acids (D-stereoisomers) and artificial amino acids. A protein-catalyzed screen that consisted of the 1° peptide ligand, the protein bCAII, and a large one-bead-one-compound library was utilized to identify the biligand (1°+2°). The triligand (1°+2°+3°) was similarly prepared, but with the biligand and the protein bCAII screened against a large one-bead one-compound library.

Figure 14:
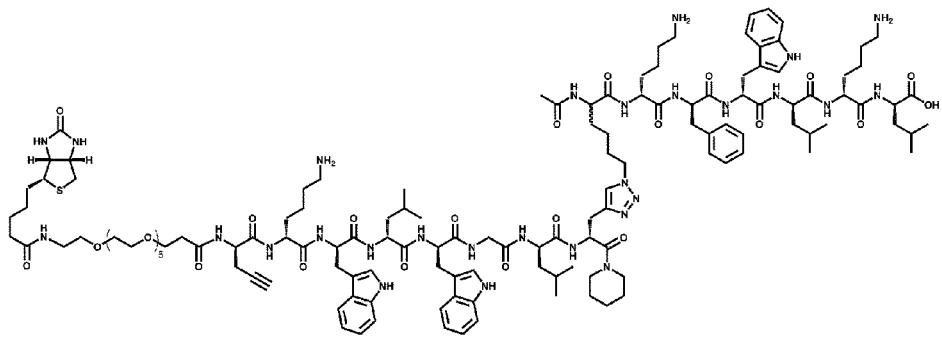
FIG. 14 shows the structural formula of a biotinylated biligand anchor according to an embodiment herein described. In particular, the depicted biotinylated biligand anchor is an extension of the deprotected biligand anchor shown in FIG. 12, wherein biotin provides the resulting modified multi-ligand capture agent with detectability. The biotinylated biligand anchor of FIG. 14 can be used as a suitable reagent for dot blot experiments (see FIG. 21) and the assay schematically shown in FIG. 29 (see Example 13).
Figure 15:
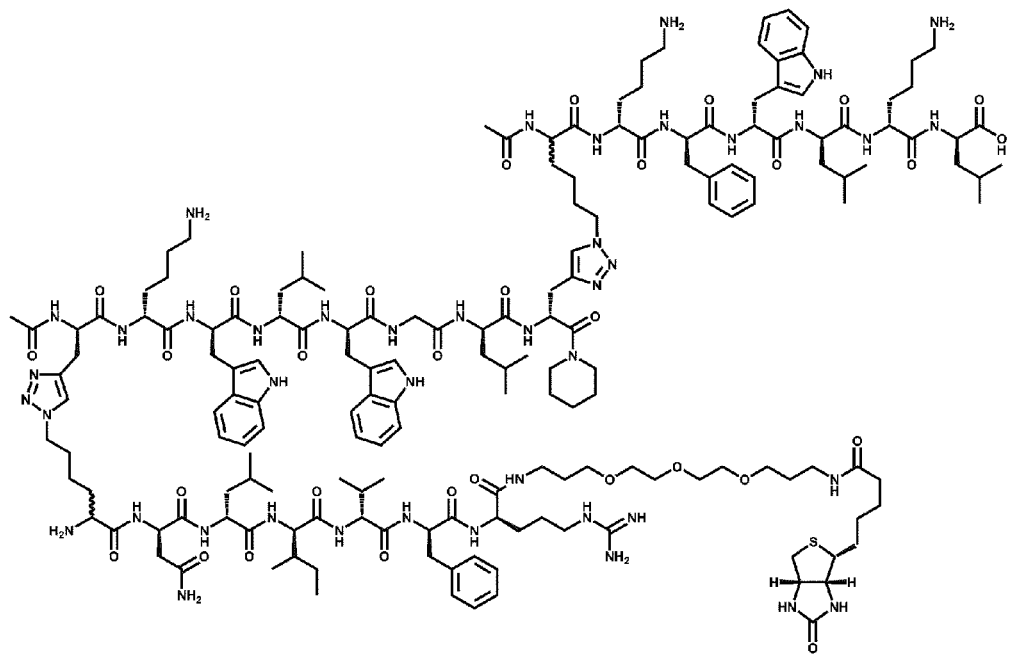
FIG. 15 shows the structural formula of a biotinylated triligand capture agent according to an embodiment herein described. In particular, the biotinylated triligand capture agent of FIG. 15 is an extension of the triligand capture agent shown in FIG. 6, wherein biotin provides the resulting modified multi-ligand capture agent with detectability. The biotinylated biligand anchor of FIG. 14 can be used as a suitable reagent for dot blot, western blot, and ELISA-type assays illustrated by Examples 16, 20 and 21.

These capture agents can modified by adding a biotin molecule to the terminal end of one of the ligand components, as shown in FIG. 14 and FIG. 15 Anchor ligands (FIG. 26) and biligands can be modified with fluorescein isothiocyanate (FITC) other fluorophores, other small molecule labels, oligonucleotides, and proteins that can be site-specifically coupled to capture agents.

Example 20

Western Blot Performed with Multi-Ligand Capture Agents

Western blots are a second common method for detecting proteins. The difference between a native western blot, and a western blot procedure, is that the protein to be detected is denatured for a standard western blot.

In the native western blot method for detecting proteins, the proteins in a sample are subjected to non-denaturing gel electrophoresis and transferred to an absorbent membrane. The capture agent, which includes but is not limited to an antibody or multi-ligand, is used to interrogate the proteins on the membrane. After specific binding of the capture agent to the target, a secondary detection agent is added to specifically bind the capture agent. The secondary detection agent (e.g., streptavidin-HRP) often exhibits chemiluminescence which allows visualization of the results.

Demonstrations of native western blots to detect bCAII from 10% serum, with direct comparisons between the triligand and a commercial antibody are shown in FIG. 22.

FIG. 22A shows a Coomassie-stained native gel, detailing the total protein content. Native western blots, probing with a primary antibody (FIG. 22B) or triligand capture agent (FIG. 22C), illustrate strong selectivity for bCAII even in the presence of serum and indicate that the triligand is nearly as sensitive as the commercial antibody.

Example 21

ELISA-Like Sandwich Assay Executed with Multi-Ligand Capture Agents

Sandwich assays are a third common method for detecting proteins. Sandwich assays rely upon two antibodies, a primary capture antibody (1°) and a labeled detection antibody (2° antibody), for detecting the target (protein) of interest. The 1° antibody is typically coated onto a surface, such as the surface of a well within a 96-well plate. A solution, such as serum, which contains the protein, is added to the well and the protein is allowed to diffuse to the surface where it is captured by the 1° antibody. The 2° antibody is then added to the same well. This antibody is designed to bind to a different binding site, or epitope, of the protein to be detected, and this 2° antibody can be labeled in a way that allows for the entire complex of protein+antibodies to be detected optically or by some other means. For optical detection, the label is often an optically absorbent dye molecule or a fluorescent dye molecule, and that label is often attached to the 2° antibody using by first conjugating biotin to the 2° antibody, and then allowing a labeled protein (e.g., streptavidin) to bind to the biotin. Other methods are possible, such as directly attaching the fluorescent label to the 2° antibody, or utilizing a gold nanoparticle as a label instead of the fluorescent or optically absorbent dye molecule, or using a radioactive molecule as the label, in which case the final detection is done using a scintillation counter or appropriately sensitized film.

In a typical ELISA sandwich assay, a primary capture antibody (1°) is coated onto a surface (e.g., a well within a 96-well plate), and then a solution containing the target molecule is allowed to diffuse to the surface and specifically bind. A labeled (e.g., biotin) detection antibody (2°) completes the "sandwich" by specifically binding to an orthogonal site on the target molecule. The label is then detected by fluorescence or some other optical method, and the signal intensity is proportional to the amount of target molecule captured in the assay.

Demonstration of sandwich-type ELISA assays on streptavidin-functionalized microtiter plates to detect bCAII using a combined commercial antibody (2° capture agent) and triligand (as the 1° capture agent) are shown in FIG. 23.

Figure 23C:
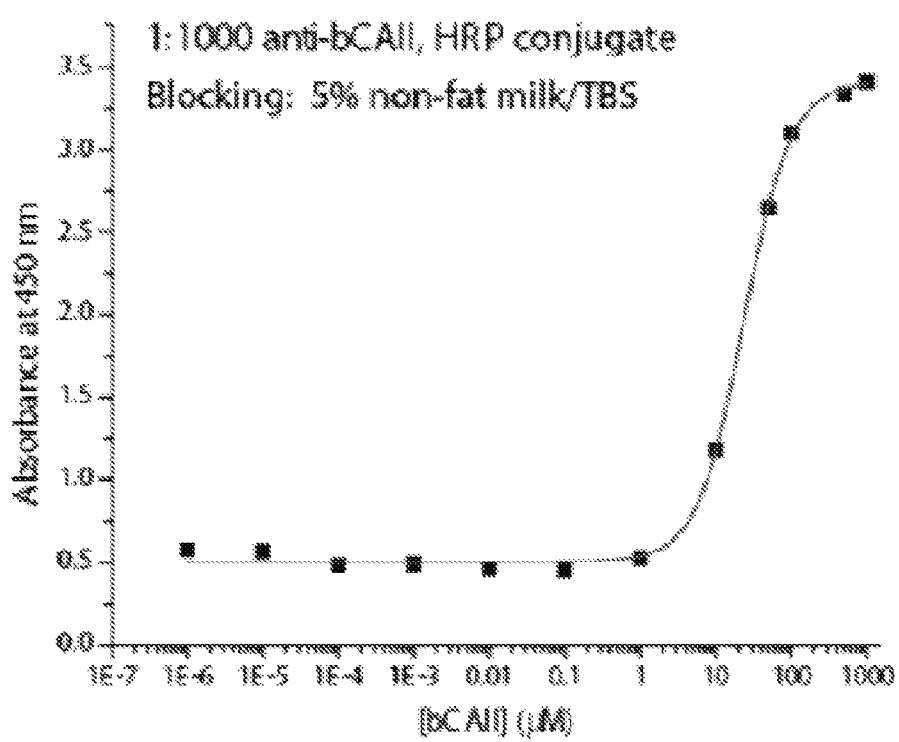
Figure 23D:
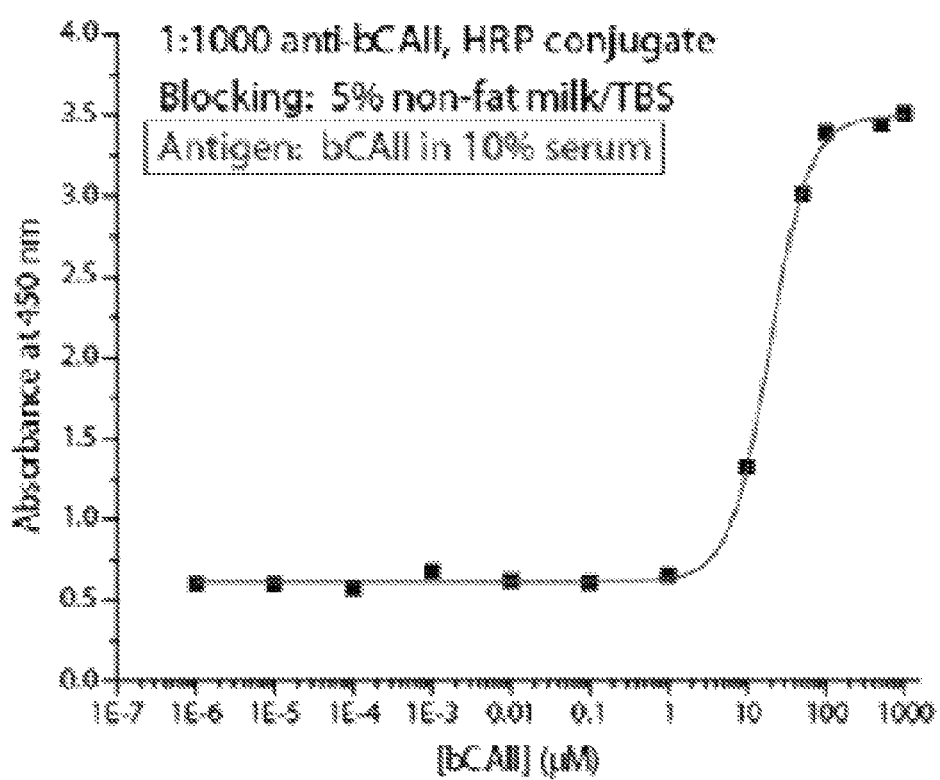
Figure 24:
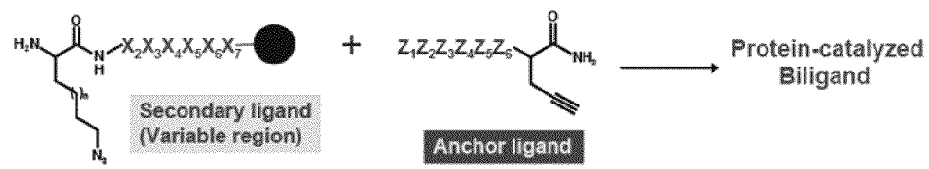
FIG. 24 shows a schematic illustrating two types of biligand screen according to some embodiments herein described. In Panel A, the in situ screen for a secondary (2°) ligand, originally detailed in FIG. 20, is re-drawn for comparison. In Panel B, the on-bead screen for a secondary (2°) ligand is shown that was utilized as confirmation that the Panel A screen was working.
Figure 24:
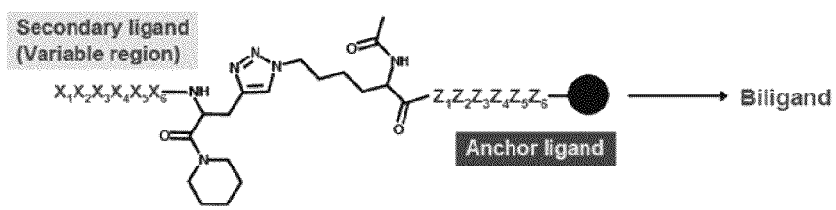

FIG. 23 24 shows an ELISA-like sandwich absorbance assays using triligand to detect bCAII protein. In particular FIG. 23A shows the structure of a fully assembled assay. FIG. 23B shows experimental data of ELISA assays at varying concentrations of bCAII as performed in the wells of a 96-well plate. Increasing bCAII concentration is detected as increasing grey color. FIGS. 23C-23D show two typical assay conditions. FIG. 23C is an assay performed with bCAII presented in buffered solution, while FIG. 23D is an assay performed in 10% porcine serum with no compromise in specific binding by either the triligand capture agent or detection antibody.

The examples set forth above are provided to give those of ordinary skill in the art a complete disclosure and description of how to make and use the embodiments of the devices, systems and methods of the disclosure, and are not intended to limit the scope of what the inventors regard as their disclosure. All patents and publications mentioned in the disclosure are indicative of the levels of skill of those skilled in the art to which the disclosure pertains. All references cited in this disclosure are incorporated by reference to the same extent as if each reference had been incorporated by reference in its entirety individually.

The entire disclosure of each document cited (including patents, patent applications, journal articles, abstracts, laboratory manuals, books, or other disclosures) is hereby incorporated herein by reference.

Further, the hard copy of the sequence listing submitted herewith and the corresponding computer readable form are both incorporated herein by reference in their entireties.

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The terms "multiple" and "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications may be made without departing from the spirit and scope of the present disclosure. In particular, modifications of the above-described modes for carrying out the disclosure that are obvious to persons of skill in the art are intended to be within the scope of the present disclosure. Accordingly, other embodiments are within the scope of the following claims.

REFERENCES

Atherton, E. and R. C. Sheppard, in *Solid Phase Peptide Synthesis—A Practical Approach*, Oxford University Press, USA, 1989, p. 136.

Baldwin, J. J., J. J. Burbaum, I. Henderson, and M. H. J. Ohlmeyer (1995). "Synthesis of a Small Molecule Combinatorial Library Encoded with Molecular Tags." *J. Am. Chem. Soc.* 117(20): 5588-5589.

Bock, V. D., H. Hiemstra, and J. H. van Maarseveen, (2006). "Cu$^1$-Catalyzed Azide-Alkyne "Click" Cycloadditions from a Mechanistic and Synthetic Perspective." *Eur. J. Org. Chem.:* 51-68.

Bourne, Y., H. C. Kolb, Z. Radić, K. B. Sharpless, P. Taylor, and P. Marchot (2004). "Freeze-frame inhibitor captures acetylcholinesterase in a unique conformation." *Proc. Natl. Acad. Sci. USA* 101(6): 1449-1454.

Brown, S. (1997). "Metal-recognition by repeating polypeptides." *Nat. Biotechnol.* 15: 269-272.

Cao, P., K. Xu, and J. R. Heath (2008). "Azidation of Silicon (111) Surfaces." *J. Am. Chem. Soc.* 130(45): 14910-14911.

Carpino, L. A., A. El-Faham, C. A. Minor, and F. Albericio (1994). "Advantageous applications of azabenzotriazole (triazolopyridine)-based coupling reagents to solid-phase peptide synthesis." *J. Chem. Soc., Chem. Commun.* 2: 201-203.

Chenault, H. K., J. Dahmer, and G. M. Whitesides (1989). "Kinetic resolution of unnatural and rarely occurring amino acids: Enantioselective hydrolysis of N-acyl amino acids catalyzed by acylase I." *J. Am. Chem. Soc.* 111(16): 6354-6364.

Coin, I., M. Beyermann, and M. Bienert (2007). "Solid-phase peptide synthesis: From standard procedures to the synthesis of difficult sequences." *Nat. Protocols* 2(12): 3247-3256.

Dixon, S. M.; P. Li, R. Liu, H. Wolosker, K. S. Lam, M. J. Kurth, and M. D. Toney (2006). "Slow-binding human serine racemase inhibitors from high-throughput screening of combinatorial libraries." *J. Med. Chem.* 49(8): 2388-2397.

Eteshola, E., L. J. Brillson, and S. C. Lee (2005). "Selection and characteristics of peptides that bind thermally grown silicon dioxide films." *Biomol. Eng.* 22: 201-204.

Fan, R., O. Vermesh, A. Srivastava, B. K. H. Yen, L. Qin, H. Ahmad, G. A. Kwong, C.-C. Liu, J. Gould, L. Hood, and J. R. Heath (2008). "Integrated barcode chips for rapid, multiplexed analysis of proteins in microliter quantities of blood." *Nat. Biotechnol.* 26: 1373-1378.

Furka, A., F. Sebestyen, M. Asgedom, and G. Dibo, (1991). "General method for rapid synthesis of multicomponent peptide mixtures." *Int. J. Pept. Protein Res.* 37: 487-493.

Garcia-Martin, F., N. Bayó-Puxan, L. J. Cruz, J. C. Bohling, and F. Albericio (2007). "Chlorotrityl Chloride (CTC) Resin as a Reusable Carboxyl Protecting Group." *QSAR Comb. Sci.* 26(10), 1027-1035.

Geysen, H. M. and T. J. Mason (1993). "Screening chemicallly synthesized peptide libraries for biologically-relevant molecules." *Bioorg. Med. Chem. Lett.* 3(3): 397-404.

Gramlich, P. M. E., C. T. Wirges, J. Gierlich, and T. Carell (2008). "Synthesis of Modified DNA by PCR with Alkyne-Bearing Purines Followed by a Click Reaction." *Org. Lett.* 10(2): 249-251.

Halpin, D. R., J. A. Lee, S. J. Wrenn, and P. B. Harbury (2004). "DNA Display III. Solid-Phase Organic Synthesis on Unprotected DNA." *PLoS Biology* 2(7): 1031-1038.

Hochgürtel, M., H. Kroth, D. Piecha, M. W. Hofmann, C. Nicolau, S. Krause, O. Schaaf, G. Sonnenmoser, and A. V. Eliseev (2002). "Target-induced formation of neuraminidase inhibitors from in vitro virtual combinatorial libraries." *Proc. Natl. Acad. Sci. USA* 99(6): 3382-3387.

Hu, X., J. Sun, H.-G. Wang, and R. Manetsch (2008). "Bcl-X$_L$-Templated Assembly of Its Own Protein-Protein Interaction Modulator from Fragments Decorated with Thio Acids and Sulfonyl Azides." *J. Am. Chem. Soc.* 130(42): 13820-13821.

Kolb, H. C. and K. B. Sharpless (2003). "The growing impact of click chemistry on drug discovery." *Drug Disc. Today* 8(24): 1128-1137.

Krasiński, A., Z. Radić, R. Manetsch, J. Raushel, P. Taylor, K. B. Sharpless, and H. C. Kolb (2005). "In situ selection of lead compounds by click chemistry: Target-guided optimization of acetylcholinesterase inhibitors." *J. Am. Chem. Soc.* 127(18): 6686-6692.

Lam, K. S., M. Lebl, and V. Krchňák (1997). "The 'one-bead-one-compound' combinatorial library method." *Chem. Rev.* 97(2): 411-448.

Landon, L. A., J. Zou, and S. L. Deutscher (2004). "Effective combinatorial strategy carbohydrate to increase affinity of carbohydrate binding by peptides." *Mol. Diversity* 8: 35-50.

Laursen, R. A. (1971). "Solid-phase Edman degradation: An automatic peptide sequencer." *Eur. J. Biochem.* 20: 89-102.

Lee, H.-S., J.-S. Park, B. M. Kim, and S. H. Gellman (2003). "Efficient synthesis of enantiomerically pure $^{β2}$-amino acids via chiral isoxazolidinones." *J. Org. Chem.* 68(4): 1575-1578.

Lehman, A., S. Gholami, M. Hahn, and K. S. Lam (2006). "Image subtraction approach to screening one-bead-one-compound combinatorial libraries with complex protein mixtures." *J. Comb. Chem.* 8(4): 562-570.

Lewis, W. G., L. G. Green, F. Grynszpan, Z. Radić, P. R. Carlier, P. Taylor, M. G. Finn, and K. B. Sharpless (2002). "Click chemistry in situ: Acetylcholinesterase as a reaction vessel for the selective assembly of a femtomolar inhibitor from an array of building blocks." *Angew. Chem.* 114(6): 1095-1099; *Angew. Chem. Int. Ed.* 41(6): 1053-1057.

Lewis, J. K., J. Wei, and G. Siuzdak (2000). "Matrix-assisted laser desorption/ionization mass spectrometry in peptide and protein analysis." In *Encyclopedia of Analytical Chemistry,* R. A. Meyers (ed.), 5880-5894.

Li. S., D. Bowerman, N. Marthandan, S. Klyza, K. J. Luebke, H. R. Gamer, and T. Kodadek (2004). "Photolithographic Synthesis of Peptoids." *J. Am. Chem. Soc.* 126(13): 4088-4089.

Li, S., N. Marthandan, D. Bowerman, H. R. Garner, and T. Kodadek (2005). "Photolithographic synthesis of cyclic peptide arrays using a differential deprotection strategy." *Chem. Commun.* 581-583.

Liu, G. and K. S. Lam, in *Combinatorial Chemistry—A Practical Approach,* Ed. H. Fenniri, Oxford University Press, USA, 2000, pp. 43-44.

Lusvarghi, S., J. M. Kim, Y. Creeger, and B. A. Armitage (2009). "Refined multivalent display of bacterial spore-binding peptides." *Org. Biomol. Chem.* 7: 1815-1820.

Manetsch, R., A. Krasiński, Z. Radić, J. Raushel, P. Taylor, K. B. Sharpless, and H. C. Kolb (2004). "In situ click chemistry: Enzyme inhibitors made to their own specifications." *J. Am. Chem. Soc.* 126(40): 12809-12818.

Marks, K. M., M. Rosinov, and G. P. Nolan (2004). "In Vivo Targeting of Organic Calcium Sensors via Genetically Selected Peptides." *Chem. Biol.* 11: 347-356.

McAlpine, M. C., H. D. Agnew, R. D. Rohde, M. Blanco, H. Ahmad, A. D. Stuparu, W. A. Goddard, and J. R. Heath (2008). "Peptide-Nanowire Hybrid Materials for Selective Sensing of Small Molecules." *J. Am. Chem. Soc.* 130(29): 9583-9589.

Mocharla V. P., B. Colasson, L. V. Lee, S. Röper, K. B. Sharpless, C.-H. Wong, and H. C. Kolb (2005). "In Situ Click Chemistry: Enzyme-Generated Inhibitors of Carbonic Anhydrase II." *Angew. Chem.* 117(1): 118-122; *Angew. Chem. Int. Ed.* 44(1): 116-120.

Panicker, R. C., X. Huang, and S. Q. Yao (2004). "Recent Advances in Peptide-Based Microarray Technologies." *Comb. Chem. High Throughput Screen.* 7(6): 547-556.

Papalia, G. A., S. Leavitt, M. A. Bynum, P. S. Katsamba, R. Wilton, H. Qiu, M. Steukers, S. Wang, L. Bindu, S. Phogat, A. M. Giannetti, T. E. Ryan, V. A. Pudlak, K. Matusiewicz, K. M. Michelson, A. Nowakowski, A. Pham-Baginski, J. Brooks, B. C. Tieman, B. D. Bruce, M. Vaughn, M. Baksh, Y. H. Cho, M. De Wit, A. Smets, J. Vandersmissen, L. Michiels, and D. G. Myszka (2006). "Comparative analysis of 10 small molecules binding to carbonic anhydrase II by different investigators using Biacore technology." *Anal. Biochem.* 359: 94-105.

Pocker, Y. and J. T. Stone (1967). "The Catalytic Versatility of Erythrocyte Carbonic Anhydrase. III. Kinetic Studies of the Enzyme-Catalyzed Hydrolysis of p-Nitrophenyl Acetate." *Biochemistry* 6(3): 668-678.

Poulin-Kerstien, A. T. And P. B. Dervan (2003). "DNA-Templated Dimerization of Hairpin Polyamides." *J. Am. Chem. Soc.* 125(51): 15811-15821.

Roice, M., I. Johannsen, and M. Meldal (2004). "High Capacity Poly(ethylene glycol) Based Amino Polymers for Peptide and Organic Synthesis." *QSAR Comb. Sci.* 23(8): 662-673.

Rohde, R. D., H. D. Agnew, W.-S. Yeo, R. C. Bailey, and J. R. Heath (2006). "A Non-Oxidative Approach toward Chemically and Electrochemically Functionalizing Si(111)." *J. Am. Chem. Soc.* 128(29): 9518-9525.

Rostovtsev V. V., L. G. Green, V. V. Fokin, and K. B. Sharpless (2002). "A Stepwise. Huisgen Cycloaddition Process: Copper(I)-Catalyzed Regioselective "Ligation" of Azides and Terminal Alkynes." *Angew. Chem.* 114(14): 2708-2711; *Angew. Chem. Int. Ed.* 41(14): 2596-2599.

Sanghvi, A. B., K. P-H Miller, A. M. Belcher, and C. E. Schmidt (2005). "Biomaterials functionalization using a novel peptide that selectively binds to a conducting polymer." *Nat. Mater.* 4: 496-502.

Sano, T. and C. R. Cantor (1990). "Expression of a Cloned Streptavidin Gene in *Escherichia coli*." *Proc. Natl. Acad. Sci. USA* 87(1): 142-146.

Saxon, E. and Bertozzi, C. R. (2000). "Cell Surface Engineering by a Modified Staudinger Reaction." *Science* 287(5460): 2007-2010.

Smith, G. P. and V. A. Petrenko (1997). "Phage display." *Chem. Rev.* 97(2): 391-410.

Svedhem, S., K. Enander, M. Karlsson, H. Sjöbom, B. Liedberg, S. Löfås, L.-G. Mårtensson, S. E. Sjöstrand, S. Svensson, U. Carlsson, and I. Lundström (2001). "Subtle Differences in Dissociation Rates of Interactions between Destabilized Human Carbonic Anhydrase II Mutants and Immobilized Benzenesulfonamide Inhibitors Probed by a Surface Plasmon Resonance Biosensor." *Anal. Biochem.* 296(2): 188-196.

Tornøe and Meldal, "Peptidotriazoles: Copper(I)-Catalyzed 1,3-Dipolar Cycloadditions on Solid-Phase" in Peptides: The Wave of the Future (Lebel and Houghten, eds., 2001), p. 263;

Tornøe et al., *J. Org. Chem.* 67(9):3057-3064 (2002); Rostovtsev, V. V. et al., 2002].

Tse, W. C. and D. L. Boger (2004). "Sequence-Selective DNA Recognition: Natural Products and Nature's Lessons." *Chem. Biol.* 11: 1607-1617.

van Hest, J. C. M., K. L. Kiick, and D. A. Tirrell (2000). "Efficient incorporation of unsaturated methionine analogues into proteins in vivo." *J. Am. Chem. Soc.* 122(7): 1282-1288.

Wang, X., L. Peng, R. Liu, S. S. Gill, and Kit S. Lam (2005). "Partial Alloc-deprotection approach for ladder synthesis of 'one-bead one-compound' combinatorial libraries." *J. Comb. Chem.* 7(2): 197-209.

Weterings, J. J., S. Khan, G. J. van der Heden, J. W. Drijfhout, C. J. M. Melief, H. S. Overkleeft, S. H. van der Burg, F. Ossendorp, G. A. van der Marel, and D. V. Filippov (2006). "Synthesis of 2-alkoxy-8-hydroxyadenylpeptides: Towards synthetic epitope-based vaccines." *Bioorg. Med. Chem. Lett.* 16(12): 3258-3261.

Whaley, S. R., D. S. English, E. L. Hu, P. F. Barbara, and A. M. Belcher (2000). "Selection of peptides with semiconductor binding specificity for directed nanocrystal assembly." *Nature* 405: 665-668.

Whiting M., J. Muldoon, Y.-C. Lin, S. M. Silverman, W. Lindstrom, A. J. Olson, H. C. Kolb, M. G. Finn, K. B. Sharpless, J. H. Elder, and V. V. Fokin (2006). "Inhibitors of HIV-1 Protease by Using In Situ Click Chemistry." *Angew. Chem.* 118(9): 1463-1467; *Angew. Chem. Int. Ed.* 45(9): 1435-1439.

Williams, K. P., X.-H. Liu, T. N. M. Schumacher, H. Y. Lin, D. A. Ausiello, P. S. Kim, and D. P. Bartel (1997). "Bioactive and nuclease-resistant L-DNA ligand of vasopressin." *Proc. Natl. Acad. Sci. USA* 94: 11285-11290.

Yang, X., S. E. Bassett, X. Li, B. A. Luxon, N. K. Herzog, R. E. Shope, J. Aronson, T. W. Prow, J. F. Leary, R. Kirby, A. D. Ellington, and D. G. Gorenstein (2002). "Construction and selection of bead-bound combinatorial oligonucleoside phosphorothioate and phosphorodithioate aptamer libraries designed for rapid PCR-based sequencing." *Nucleic Acids Res.* 30(23): e132.

Yin, H., R. I. Litvinov, G. Vilaire, H. Zhu, W. Li, G. A. Caputo, D. T. Moore, J. D. Lear, J. W. Weisel, W. F. DeGrado, J. S. Bennett (2006). "Activation of platelet αIIbβ3 by an exogenous peptide corresponding to the transmembrane domain of αIIb." *J. Biol. Chem.* 281(48): 36732-36741.

Zhang, Z. and E. Fan (2006). "Solid phase synthesis of peptidotriazoles with multiple cycles of triazole formation." *Tetrahedron Lett.* 47(5): 665-669.

What is claimed is:

1. A method of making higher-order multi-ligand capture agents, the method comprising:
   contacting a modified anchor ligand with a first plurality of candidate ligands and a molecular target, wherein the first plurality of candidate ligands comprises at least about 3200 unique ligands,
   whereby the modified anchor ligand is covalently linked to one or more of the candidate ligands in a reaction catalyzed by the molecular target, thereby forming one or more bi-ligand capture agents, wherein each of the bi-ligand capture agents comprises the modified anchor ligand and one of the candidate ligands,
   wherein the anchor ligand can bind the molecular target, wherein the modified anchor ligand comprises a first functional group, wherein the first functional group is capable of specifically reacting with a corresponding second functional group, wherein each of the candidate ligands comprises the second functional group;
   modifying one of the bi-ligand capture agents by covalently attaching a third functional group, wherein the third functional group is capable of specifically reacting with a corresponding fourth functional group, and
   contacting the modified bi-ligand capture agent with a second plurality of candidate ligands and the molecular target, wherein the second plurality of candidate ligands comprises at least about 3200 unique ligands,
   whereby the modified bi-ligand capture agent is covalently linked to one or more of the candidate ligands in a reaction catalyzed by the molecular target, thereby forming one or more higher order tri-ligand capture agents, wherein each of the higher order tri-ligand capture agents comprises the modified bi-ligand capture agent and one of the candidate ligands,
   wherein each of the candidate ligands in the second plurality of capture ligands comprises the fourth functional group, wherein the plurality of candidate ligands comprises a combinatorial library of compounds, wherein the combinatorial library of compounds comprises compounds comprising permutations of a group of subunits linked in chains; and
   wherein the dissociation constant for binding of the higher-order tri-ligand capture agent to the molecular target is smaller than the dissociation constant for binding of the bi-ligand capture agent to the molecular target, the dissociation constant for binding of the bi-ligand capture agent to the molecular target is smaller than the dissociation constant for binding of the anchor ligand to the molecular target, wherein the dissociation constant of the tri-ligand capture agent to the molecular target is at least $1 \times 10^{-6}$ and wherein the anchor ligand, the candidate ligand covalently linked to the anchor ligand and the candidate ligand covalently linked to the bi-ligand bind to the molecular target at distinct epitopes.

2. The method of claim 1, wherein prior to contacting it is not known which of the candidate ligands can bind to the molecular target.

3. The method of claim 1, wherein the chains are straight, branched, circular, or a combination.

4. The method of claim 1, wherein the group of subunits comprises amino acids, modified amino acids, or a combination.

5. The method of claim 4, wherein the group of subunits further comprises one or more small organic molecules.

6. The method of claim 4, wherein the amino acids in the group of subunits consists essentially of a subset of amino acids.

7. The method of claim 4, wherein the modified amino acids in the group of subunits consists essentially of a subset of modified amino acids.

8. The method of claim 1, wherein the first plurality of candidate ligands comprises at least about 117,649 unique ligands and wherein the second plurality of candidate ligands comprises at least about 117,649 unique ligands.

9. The method of claim 1, wherein the first plurality of candidate ligands comprises at least about 262,144 unique ligands and wherein the second plurality of candidate ligands comprises at least about 262,144 unique ligands.

10. The method of claim 1, wherein the first plurality of candidate ligands comprises at least about 2,476,099 unique ligands and wherein the second plurality of candidate ligands comprises at least about 2,476,099 unique ligands.

* * * * *

SEQUENCE LISTING

```
<160> NUMBER OF SEQ ID NOS: 3

<210> SEQ ID NO 1
<211> LENGTH: 56
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
```

```
<222> LOCATION: (1)..(1)
<223> OTHER INFORMATION: Aminohexyl modification on G residue

<400> SEQUENCE: 1
gggacaatta ctatttacaa ttacaatgct cacgtggtac gagttcgtct cccagg        56

<210> SEQ ID NO 2
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 2
taatacgact cactataggg acaattacta tttacaatta ca                        42

<210> SEQ ID NO 3
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 3
accgctgcca gaccccgatt tggcctggga gacgaactcg                           40
```